(12) United States Patent
Zhu et al.

(10) Patent No.: US 8,423,139 B2
(45) Date of Patent: *Apr. 16, 2013

(54) METHODS, DEVICES AND SYSTEMS FOR CARDIAC RHYTHM MANAGEMENT USING AN ELECTRODE ARRANGEMENT

(75) Inventors: Qingsheng Zhu, Wexford, PA (US); Daniel Felipe Ortega, Buenos Aires (AR)

(73) Assignee: Cardiac Pacemakers, Inc., St. Paul, MN (US)

( * ) Notice: Subject to any disclaimer, the term of this patent is extended or adjusted under 35 U.S.C. 154(b) by 204 days.

This patent is subject to a terminal disclaimer.

(21) Appl. No.: 12/147,376

(22) Filed: Jun. 26, 2008

(65) Prior Publication Data

US 2009/0005846 A1 Jan. 1, 2009

Related U.S. Application Data

(63) Continuation-in-part of application No. 11/300,611, filed on Dec. 13, 2005, now Pat. No. 7,512,440, and a continuation-in-part of application No. 11/300,242, filed on Dec. 13, 2005.

(60) Provisional application No. 61/020,511, filed on Jan. 11, 2008, provisional application No. 60/947,310, filed on Jun. 29, 2007, provisional application No. 60/947,308, filed on Jun. 29, 2007.

(30) Foreign Application Priority Data

Dec. 20, 2004 (AR) .............................. 20040104782

(51) Int. Cl.
*A61N 1/362* (2006.01)

(52) U.S. Cl.
USPC .......................................................... 607/9

(58) Field of Classification Search .................. 607/4, 9, 607/126, 128
See application file for complete search history.

(56) References Cited

U.S. PATENT DOCUMENTS 3,614,955 A 10/1971 Mirowski
3,804,098 A 4/1974 Friedman
(Continued)

FOREIGN PATENT DOCUMENTS

DE 2827595 A1 4/1979
DE 3712082 A1 10/1988
(Continued)

OTHER PUBLICATIONS

Alboni. *Bundle Branch Blocks Anatomically Located in the His Bundle.* Italian Cardiology Journal, vol. 10, No. 12, 1980. English translation thereof, followed by Italian publication.

(Continued)

*Primary Examiner* — Brian T Gedeon
(74) *Attorney, Agent, or Firm* — Schwegman Lundberg & Woessner, P.A.

(57) ABSTRACT

Various embodiments of the present invention are directed to systems, methods and devices for cardiac applications. One such device is directed to a catheter, and uses thereof, for capturing myocardium of a heart by delivering pacing signals to a location in the heart. The location is near a His Bundle of the heart. The catheter has a proximal end for interfacing with an electrical pacing signal source and a distal end. The distal end includes a fixation mechanism that attaches the catheter to heart tissue. First and second electrodes are also located at the distal end. Each electrode is individually addressable for providing pacing signals to the heart tissue and also arranged to physically contact the heart tissue when the fixation mechanism is attached to the heart tissue.

16 Claims, 28 Drawing Sheets

U.S. PATENT DOCUMENTS

| | | |
|---|---|---|
| 3,866,615 A | 2/1975 | Hewson |
| 3,911,928 A | 10/1975 | Lagergren |
| 3,942,536 A | 3/1976 | Mirowski et al. |
| 3,949,757 A | 4/1976 | Sabel |
| 3,995,623 A | 12/1976 | Blake et al. |
| 4,026,303 A | 5/1977 | Babotai |
| 4,030,508 A | 6/1977 | Thalen |
| 4,057,067 A | 11/1977 | Lajos |
| 4,106,512 A | 8/1978 | Bisping |
| 4,136,703 A | 1/1979 | Wittkampf |
| 4,154,247 A | 5/1979 | O'Neill |
| 4,217,913 A | 8/1980 | Dutcher |
| 4,258,725 A | 3/1981 | O'Neill |
| 4,278,093 A | 7/1981 | Lafortune et al. |
| 4,282,885 A | 8/1981 | Bisping |
| 4,289,134 A | 9/1981 | Bernstein |
| 4,289,144 A | 9/1981 | Gilman |
| 4,311,153 A | 1/1982 | Smits |
| 4,332,259 A | 6/1982 | McCorkle, Jr. |
| 4,365,639 A | 12/1982 | Goldreyer |
| 4,393,883 A | 7/1983 | Smyth et al. |
| 4,402,329 A | 9/1983 | Williams |
| 4,437,474 A | 3/1984 | Peers-Trevarton |
| 4,458,677 A | 7/1984 | McCorkle, Jr. |
| 4,458,695 A | 7/1984 | Peers-Trevarton |
| 4,463,765 A | 8/1984 | Gold |
| 4,469,104 A | 9/1984 | Peers-Trevarton |
| 4,497,326 A | 2/1985 | Curry |
| 4,540,236 A | 9/1985 | Peers-Trevarton |
| 4,543,956 A | 10/1985 | Herscovici |
| 4,549,548 A | 10/1985 | Wittkampf et al. |
| 4,559,951 A | 12/1985 | Dahl et al. |
| 4,567,901 A | 2/1986 | Harris |
| 4,570,642 A | 2/1986 | Kane et al. |
| 4,577,643 A | 3/1986 | Beranek |
| 4,589,420 A | 5/1986 | Adams et al. |
| 4,602,645 A | 7/1986 | Barrington et al. |
| 4,603,705 A | 8/1986 | Speicher et al. |
| 4,624,265 A | 11/1986 | Grassi |
| 4,624,266 A | 11/1986 | Kane |
| 4,627,439 A | 12/1986 | Harris |
| 4,630,204 A | 12/1986 | Mortara |
| 4,633,880 A | 1/1987 | Osypka et al. |
| 4,641,649 A | 2/1987 | Walinsky et al. |
| 4,643,201 A | 2/1987 | Stokes |
| 4,646,755 A | 3/1987 | Kane |
| 4,649,937 A | 3/1987 | DeHaan et al. |
| 4,649,938 A | 3/1987 | McArthur |
| 4,664,113 A | 5/1987 | Frisbie et al. |
| 4,667,686 A | 5/1987 | Peers-Travarton |
| H356 H | 11/1987 | Stokes et al. |
| 4,721,115 A | 1/1988 | Owens |
| 4,751,931 A | 6/1988 | Briller et al. |
| 4,784,161 A | 11/1988 | Skalsky et al. |
| 4,785,815 A | 11/1988 | Cohen |
| 4,799,486 A | 1/1989 | DuFault |
| 4,799,493 A | 1/1989 | DuFault |
| 4,819,647 A | 4/1989 | Byers et al. |
| 4,819,661 A | 4/1989 | Heil, Jr. et al. |
| 4,819,662 A | 4/1989 | Heil, Jr. et al. |
| 4,876,109 A | 10/1989 | Mayer et al. |
| 4,886,074 A | 12/1989 | Bisping |
| 4,892,102 A | 1/1990 | Astrinsky |
| 4,895,152 A | 1/1990 | Callaghan et al. |
| 4,922,607 A | 5/1990 | Doan et al. |
| 4,922,927 A | 5/1990 | Fine et al. |
| 4,924,881 A | 5/1990 | Brewer |
| 4,953,564 A | 9/1990 | Berthelsen |
| 4,967,766 A | 11/1990 | Bradshaw |
| 4,972,848 A | 11/1990 | DiDomenico et al. |
| 4,994,078 A | 2/1991 | Jarvik |
| 5,002,067 A | 3/1991 | Berthelsen et al. |
| 5,007,864 A | 4/1991 | Stutz, Jr. |
| 5,016,646 A | 5/1991 | Gotthardt et al. |
| 5,050,601 A | 9/1991 | Kupersmith et al. |
| 5,056,516 A | 10/1991 | Spehr |
| 5,063,932 A | 11/1991 | Dahl et al. |
| 5,076,285 A | 12/1991 | Hess et al. |
| 5,083,564 A | 1/1992 | Scherlag |
| 5,092,879 A | 3/1992 | Jarvik |
| 5,129,404 A | 7/1992 | Spehr et al. |
| 5,144,960 A | 9/1992 | Mehra et al. |
| 5,152,299 A | 10/1992 | Soukup |
| 5,174,289 A | 12/1992 | Cohen |
| 5,179,962 A | 1/1993 | Dutcher et al. |
| 5,181,511 A | 1/1993 | Nickolls et al. |
| 5,223,226 A | 6/1993 | Wittmer et al. |
| 5,242,430 A | 9/1993 | Arenas et al. |
| 5,255,693 A | 10/1993 | Dutcher et al. |
| 5,259,394 A | 11/1993 | Bens |
| 5,259,395 A | 11/1993 | Li |
| 5,267,560 A | 12/1993 | Cohen |
| 5,275,620 A | 1/1994 | Darby et al. |
| 5,282,845 A | 2/1994 | Bush et al. |
| 5,299,569 A | 4/1994 | Wernicke et al. |
| 5,300,108 A | 4/1994 | Rebell et al. |
| 5,304,219 A | 4/1994 | Chernoff et al. |
| 5,306,292 A | 4/1994 | Lindegren |
| 5,313,953 A | 5/1994 | Yomtov et al. |
| 5,320,642 A | 6/1994 | Scherlag |
| 5,324,327 A | 6/1994 | Cohen |
| 5,336,252 A | 8/1994 | Cohen |
| 5,342,414 A | 8/1994 | Mehra |
| 5,344,439 A | 9/1994 | Otten |
| 5,358,516 A | 10/1994 | Myers et al. |
| 5,366,496 A | 11/1994 | Dahl et al. |
| 5,370,665 A | 12/1994 | Hudrlik |
| 5,374,286 A | 12/1994 | Morris |
| 5,381,790 A | 1/1995 | Kanesaka |
| 5,393,929 A | 2/1995 | Yagihashi |
| 5,405,373 A | 4/1995 | Petersson et al. |
| 5,411,544 A | 5/1995 | Mar et al. |
| 5,425,755 A | 6/1995 | Doan |
| 5,433,735 A | 7/1995 | Zanakis et al. |
| 5,439,391 A | 8/1995 | McEtchin et al. |
| 5,447,533 A | 9/1995 | Vachon et al. |
| 5,447,534 A | 9/1995 | Jammet |
| 5,456,706 A | 10/1995 | Pless et al. |
| 5,456,708 A | 10/1995 | Doan et al. |
| 5,466,253 A | 11/1995 | Doan |
| 5,476,497 A | 12/1995 | Mower et al. |
| 5,476,499 A | 12/1995 | Hirschberg |
| 5,476,501 A | 12/1995 | Stewart et al. |
| 5,476,502 A | 12/1995 | Rubin |
| 5,492,119 A | 2/1996 | Abrams |
| 5,500,008 A | 3/1996 | Fain |
| 5,514,172 A | 5/1996 | Mueller |
| 5,515,848 A | 5/1996 | Corbett, III et al. |
| 5,522,874 A | 6/1996 | Gates |
| 5,524,338 A | 6/1996 | Martyniuk et al. |
| 5,527,344 A | 6/1996 | Arzbaecher et al. |
| 5,531,780 A | 7/1996 | Vachon |
| 5,545,201 A | 8/1996 | Helland et al. |
| 5,554,178 A | 9/1996 | Dahl et al. |
| 5,571,163 A | 11/1996 | Helland |
| 5,578,068 A | 11/1996 | Laske et al. |
| 5,593,405 A | 1/1997 | Osypka |
| 5,593,433 A | 1/1997 | Spehr et al. |
| 5,609,158 A | 3/1997 | Chan |
| 5,628,778 A | 5/1997 | Kruse et al. |
| 5,628,779 A | 5/1997 | Bornzin et al. |
| 5,634,829 A | 6/1997 | Kerul |
| 5,634,899 A | 6/1997 | Shapland et al. |
| 5,674,272 A | 10/1997 | Bush et al. |
| 5,674,274 A | 10/1997 | Morgan et al. |
| 5,681,013 A | 10/1997 | Rudolph |
| 5,683,447 A | 11/1997 | Bush et al. |
| 5,702,427 A | 12/1997 | Ecker et al. |
| 5,709,753 A | 1/1998 | Olson et al. |
| 5,716,390 A | 2/1998 | Li |
| 5,718,720 A | 2/1998 | Prutchi et al. |
| 5,720,099 A | 2/1998 | Parker et al. |
| 5,728,140 A | 3/1998 | Salo et al. |
| 5,733,323 A | 3/1998 | Buck et al. |
| 5,755,766 A | 5/1998 | Chastain et al. |
| 5,769,881 A | 6/1998 | Schroeppel et al. |
| 5,772,693 A | 6/1998 | Brownlee |

| | | | |
|---|---|---|---|
| 5,782,898 A | 7/1998 | Dahl et al. | |
| 5,800,464 A | 9/1998 | Kieval | |
| 5,800,465 A | 9/1998 | Thompson et al. | |
| 5,807,306 A | 9/1998 | Shapland et al. | |
| 5,810,887 A | 9/1998 | Accorti, Jr. et al. | |
| 5,814,077 A | 9/1998 | Sholder et al. | |
| 5,814,079 A | 9/1998 | Kieval | |
| 5,851,227 A | 12/1998 | Spehr | |
| 5,871,506 A | 2/1999 | Mower | |
| 5,871,529 A | 2/1999 | Bartig et al. | |
| 5,871,531 A | 2/1999 | Struble | |
| 5,876,399 A | 3/1999 | Chia et al. | |
| 5,876,431 A | 3/1999 | Spehr et al. | |
| 5,916,214 A | 6/1999 | Cosio et al. | |
| 5,925,045 A | 7/1999 | Reimels et al. | |
| 5,935,159 A | 8/1999 | Cross, Jr. et al. | |
| 5,941,868 A | 8/1999 | Kaplan | |
| 5,944,710 A | 8/1999 | Dev et al. | |
| 5,964,795 A | 10/1999 | McVenes et al. | |
| 5,972,416 A | 10/1999 | Reimels et al. | |
| 5,995,871 A | 11/1999 | Knisley | |
| 6,006,139 A | 12/1999 | Kruse et al. | |
| 6,007,476 A | 12/1999 | Wascher et al. | |
| 6,024,739 A | 2/2000 | Ponzi et al. | |
| 6,059,726 A | 5/2000 | Lee et al. | |
| 6,070,104 A | 5/2000 | Hine et al. | |
| 6,086,582 A | 7/2000 | Altman et al. | |
| 6,096,069 A | 8/2000 | Bischoff | |
| 6,123,084 A | 9/2000 | Jandak et al. | |
| 6,141,588 A | 10/2000 | Cox et al. | |
| 6,141,594 A | 10/2000 | Flynn et al. | |
| 6,161,029 A | 12/2000 | Spreigl et al. | |
| 6,165,164 A | 12/2000 | Hill et al. | |
| 6,212,434 B1 | 4/2001 | Scheiner et al. | |
| 6,219,581 B1 | 4/2001 | Schaldach et al. | |
| 6,230,061 B1 | 5/2001 | Hartung | |
| 6,236,887 B1 | 5/2001 | Ben-Haim et al. | |
| 6,254,573 B1 | 7/2001 | Haim et al. | |
| 6,256,541 B1 | 7/2001 | Heil et al. | |
| 6,267,778 B1 | 7/2001 | Cohen | |
| 6,309,370 B1 | 10/2001 | Haim et al. | |
| 6,341,235 B1 | 1/2002 | Mower | |
| 6,345,204 B1 | 2/2002 | Scheiner et al. | |
| 6,358,247 B1 | 3/2002 | Altman et al. | |
| 6,363,286 B1 | 3/2002 | Zhu et al. | |
| 6,416,510 B1 | 7/2002 | Altman et al. | |
| 6,463,334 B1 | 10/2002 | Flynn et al. | |
| 6,468,263 B1 | 10/2002 | Fischell et al. | |
| 6,471,697 B1 | 10/2002 | Lesh | |
| 6,484,057 B2 | 11/2002 | Ideker et al. | |
| 6,505,082 B1 | 1/2003 | Scheiner et al. | |
| 6,535,766 B1 | 3/2003 | Thompson et al. | |
| 6,540,725 B1 | 4/2003 | Ponzi | |
| 6,542,775 B2 | 4/2003 | Ding et al. | |
| 6,544,270 B1 | 4/2003 | Zhang | |
| 6,547,787 B1 | 4/2003 | Altman et al. | |
| 6,556,874 B2 | 4/2003 | Audoglio | |
| 6,560,489 B2 | 5/2003 | Hauck | |
| 6,575,931 B1 | 6/2003 | Ponzi | |
| 6,585,716 B2 | 7/2003 | Altman | |
| 6,606,517 B1 | 8/2003 | Park et al. | |
| 6,609,027 B2 * | 8/2003 | Kroll et al. | 607/9 |
| 6,623,473 B1 | 9/2003 | Ponzi | |
| 6,623,474 B1 | 9/2003 | Ponzi | |
| 6,643,546 B2 | 11/2003 | Mathis et al. | |
| 6,650,940 B1 | 11/2003 | Zhu et al. | |
| 6,702,744 B2 | 3/2004 | Mandrusov et al. | |
| 6,702,777 B2 | 3/2004 | Haim et al. | |
| 6,718,206 B2 | 4/2004 | Casavant | |
| 6,766,190 B2 | 7/2004 | Ferek-Petric et al. | |
| 6,768,923 B2 | 7/2004 | Ding et al. | |
| 6,801,807 B2 | 10/2004 | Abrahamson | |
| 6,804,555 B2 | 10/2004 | Warkentin | |
| 6,810,286 B2 | 10/2004 | Donovan et al. | |
| 6,855,124 B1 | 2/2005 | Gonzalez et al. | |
| 6,901,289 B2 | 5/2005 | Dahl et al. | |
| 6,905,476 B2 | 6/2005 | Ponzi | |
| 6,907,285 B2 | 6/2005 | Denker et al. | |
| 6,909,920 B2 | 6/2005 | Lokhoff et al. | |
| 6,915,169 B2 | 7/2005 | Flynn et al. | |
| 6,931,286 B2 | 8/2005 | Sigg et al. | |
| 6,937,897 B2 | 8/2005 | Min et al. | |
| 7,027,876 B2 * | 4/2006 | Casavant et al. | 607/126 |
| 7,039,462 B2 | 5/2006 | Pastore et al. | |
| 7,096,051 B1 | 8/2006 | Alder | |
| 7,113,825 B2 | 9/2006 | Pastore et al. | |
| 7,130,682 B2 | 10/2006 | Stahmann et al. | |
| 7,187,970 B2 | 3/2007 | Shemer et al. | |
| 7,245,973 B2 | 7/2007 | Liu et al. | |
| 7,257,443 B2 | 8/2007 | Pastore et al. | |
| 7,280,872 B1 | 10/2007 | Mosesov et al. | |
| 7,317,950 B2 | 1/2008 | Lee | |
| 7,319,900 B2 | 1/2008 | Kim et al. | |
| 7,359,837 B2 | 4/2008 | Drew | |
| 7,392,095 B2 | 6/2008 | Flynn et al. | |
| 7,395,042 B2 | 7/2008 | Alder | |
| 7,400,931 B2 | 7/2008 | Mandrusov et al. | |
| 7,460,914 B2 | 12/2008 | Mandrusov et al. | |
| 7,509,170 B2 | 3/2009 | Zhang et al. | |
| 7,512,440 B2 | 3/2009 | Ortega et al. | |
| 7,529,584 B2 | 5/2009 | Laske et al. | |
| 7,792,580 B2 | 9/2010 | Borowitz et al. | |
| 7,817,784 B2 | 10/2010 | Wang et al. | |
| 8,005,544 B2 | 8/2011 | Zhu et al. | |
| 8,010,191 B2 | 8/2011 | Zhu et al. | |
| 8,010,192 B2 | 8/2011 | Zhu et al. | |
| 8,014,861 B2 | 9/2011 | Zhu et al. | |
| 8,050,756 B2 | 11/2011 | Zhu et al. | |
| 8,078,287 B2 | 12/2011 | Liu et al. | |
| 8,285,376 B2 | 10/2012 | Ortega et al. | |
| 8,290,586 B2 | 10/2012 | Zhu et al. | |
| 8,326,423 B2 | 12/2012 | Zhu et al. | |
| 2001/0031986 A1 | 10/2001 | Hauck | |
| 2001/0044619 A1 | 11/2001 | Altman | |
| 2002/0010492 A1 | 1/2002 | Donovan et al. | |
| 2002/0016615 A1 | 2/2002 | Dev et al. | |
| 2002/0022863 A1 | 2/2002 | Hauck | |
| 2002/0026228 A1 | 2/2002 | Schauerte | |
| 2002/0049478 A1 | 4/2002 | Ding et al. | |
| 2002/0058981 A1 | 5/2002 | Zhu et al. | |
| 2002/0099413 A1 | 7/2002 | Mower | |
| 2002/0120318 A1 | 8/2002 | Kroll et al. | |
| 2002/0169484 A1 | 11/2002 | Mathis et al. | |
| 2002/0183720 A1 | 12/2002 | Hill et al. | |
| 2002/0193836 A1 | 12/2002 | Schmidt | |
| 2002/0198583 A1 | 12/2002 | Rock et al. | |
| 2003/0009145 A1 | 1/2003 | Struijker-Boudier | |
| 2003/0032938 A1 | 2/2003 | Altman | |
| 2003/0069625 A1 | 4/2003 | Ley et al. | |
| 2003/0078625 A1 | 4/2003 | Casavant | |
| 2003/0093104 A1 | 5/2003 | Bonner et al. | |
| 2003/0105492 A1 | 6/2003 | Ding et al. | |
| 2003/0105496 A1 | 6/2003 | Yu et al. | |
| 2003/0109914 A1 | 6/2003 | Westlund et al. | |
| 2003/0113303 A1 | 6/2003 | Schwartz | |
| 2003/0125615 A1 | 7/2003 | Schwartz | |
| 2003/0129750 A1 | 7/2003 | Schwartz | |
| 2003/0163184 A1 | 8/2003 | Scheiner et al. | |
| 2003/0171723 A1 | 9/2003 | Ponzi | |
| 2003/0195470 A1 | 10/2003 | Ponzi | |
| 2004/0006265 A1 | 1/2004 | Alhussiny | |
| 2004/0064176 A1 | 4/2004 | Min et al. | |
| 2004/0106958 A1 | 6/2004 | Mathis et al. | |
| 2004/0122484 A1 | 6/2004 | Hatlestad et al. | |
| 2004/0153127 A1 | 8/2004 | Gordon et al. | |
| 2004/0186546 A1 | 9/2004 | Mandrusov et al. | |
| 2004/0213770 A1 | 10/2004 | Seward et al. | |
| 2004/0214182 A1 | 10/2004 | Sharma et al. | |
| 2004/0215240 A1 | 10/2004 | Lovett et al. | |
| 2004/0215249 A1 | 10/2004 | Corbucci | |
| 2004/0215251 A1 | 10/2004 | Sharma et al. | |
| 2004/0260374 A1 | 12/2004 | Zhang et al. | |
| 2005/0049516 A1 | 3/2005 | Ideker | |
| 2005/0075677 A1 | 4/2005 | Ganion et al. | |
| 2005/0125041 A1 | 6/2005 | Min et al. | |
| 2005/0136385 A1 | 6/2005 | Mann et al. | |
| 2005/0137671 A1 | 6/2005 | Liu et al. | |
| 2005/0152516 A1 | 7/2005 | Wang et al. | |

| | | | |
|---|---|---|---|
| 2005/0159725 A1 | 7/2005 | Tockman et al. | |
| 2005/0203580 A1 | 9/2005 | Prentice et al. | |
| 2005/0267557 A1 | 12/2005 | Flynn et al. | |
| 2005/0277993 A1 | 12/2005 | Mower | |
| 2006/0030810 A1 | 2/2006 | Mandrusov et al. | |
| 2006/0064027 A1 | 3/2006 | Borowitz et al. | |
| 2006/0104596 A1 | 5/2006 | Askins et al. | |
| 2006/0116596 A1 | 6/2006 | Zhou et al. | |
| 2006/0136001 A1 | 6/2006 | Ortega et al. | |
| 2006/0142812 A1 | 6/2006 | Ortega et al. | |
| 2006/0224197 A1 | 10/2006 | Havel et al. | |
| 2006/0224224 A1 | 10/2006 | Muhlenberg et al. | |
| 2007/0027488 A1 | 2/2007 | Kaiser et al. | |
| 2007/0060961 A1 | 3/2007 | Echt et al. | |
| 2007/0093872 A1 | 4/2007 | Chirife et al. | |
| 2007/0093874 A1 | 4/2007 | Chirife et al. | |
| 2007/0129764 A1 | 6/2007 | Burnes | |
| 2007/0232949 A1 | 10/2007 | Saksena | |
| 2007/0233216 A1 | 10/2007 | Liu et al. | |
| 2007/0239219 A1 | 10/2007 | Salo et al. | |
| 2008/0262587 A1 | 10/2008 | Flynn et al. | |
| 2008/0319496 A1 | 12/2008 | Zhu et al. | |
| 2008/0319499 A1 | 12/2008 | Zhu et al. | |
| 2008/0319500 A1 | 12/2008 | Zhu et al. | |
| 2008/0319501 A1 | 12/2008 | Zhu et al. | |
| 2009/0005830 A1 | 1/2009 | Zhu et al. | |
| 2009/0005832 A1 | 1/2009 | Zhu et al. | |
| 2009/0054942 A1 | 2/2009 | Zhu et al. | |
| 2009/0093859 A1 | 4/2009 | Ortega et al. | |
| 2009/0093861 A1 | 4/2009 | Ortega et al. | |
| 2009/0099619 A1 | 4/2009 | Lessmeier et al. | |
| 2009/0105778 A1 | 4/2009 | Lee et al. | |
| 2009/0259272 A1 | 10/2009 | Reddy et al. | |
| 2010/0042176 A1 | 2/2010 | Snell | |
| 2010/0318147 A1 | 12/2010 | Forslund et al. | |
| 2011/0264158 A1 | 10/2011 | Dong et al. | |
| 2011/0307026 A1 | 12/2011 | Zhu et al. | |
| 2011/0319772 A1 | 12/2011 | Ingle | |
| 2011/0319956 A1 | 12/2011 | Zhu et al. | |
| 2012/0041500 A1 | 2/2012 | Zhu et al. | |
| 2012/0041503 A1 | 2/2012 | Zhu et al. | |
| 2012/0053651 A1 | 3/2012 | Zhu et al. | |
| 2012/0101539 A1 | 4/2012 | Zhu et al. | |

FOREIGN PATENT DOCUMENTS

| | | | |
|---|---|---|---|
| EP | 0042551 A1 | 12/1981 | |
| EP | 0057877 A1 | 8/1982 | |
| EP | 0282047 A2 | 9/1988 | |
| EP | 0321764 A1 | 6/1989 | |
| EP | 0452278 A2 | 10/1991 | |
| EP | 0573275 A2 | 12/1993 | |
| EP | 0591053 A1 | 4/1994 | |
| EP | 0612538 A2 | 8/1994 | |
| EP | 0620024 A1 | 10/1994 | |
| EP | 0672431 A2 | 9/1995 | |
| EP | 0709111 A2 | 5/1996 | |
| EP | 1234597 A2 | 8/2002 | |
| EP | 1830920 A1 | 9/2007 | |
| EP | 2164560 A1 | 2/2010 | |
| EP | 2164562 A1 | 3/2010 | |
| FR | 2465489 | 3/1981 | |
| FR | 2575925 A1 | 7/1986 | |
| FR | 2757773 A1 | 7/1998 | |
| GB | 2240721 | 8/1991 | |
| JP | 10052507 A | 2/1998 | |
| WO | WO-92/20401 A1 | 11/1992 | |
| WO | WO-94/22525 A1 | 10/1994 | |
| WO | WO-96/15665 A2 | 5/1996 | |
| WO | WO-97/40883 A1 | 11/1997 | |
| WO | WO-00/74773 A1 | 12/2000 | |
| WO | WO-03/035170 A1 | 5/2003 | |
| WO | WO-2005/011475 A2 | 2/2005 | |
| WO | WO-2006/068880 A1 | 6/2006 | |
| WO | WO-2008/063498 A1 | 5/2008 | |
| WO | WO-2009/006321 A2 | 1/2009 | |
| WO | WO-2009/006327 A1 | 1/2009 | |
| WO | WO-2009/006331 A1 | 1/2009 | |
| WO | WO-2009/006339 A1 | 1/2009 | |
| WO | WO-20090/06325 A1 | 1/2009 | |
| WO | WO-2009/078751 A1 | 6/2009 | |
| WO | WO-2010/042910 A1 | 4/2010 | |
| WO | WO-2010/0718492 A2 | 6/2010 | |
| WO | WO-2011/139691 A1 | 11/2011 | |
| WO | WO-2012/005985 A2 | 1/2012 | |
| WO | WO-2012125273 A2 | 9/2012 | |

OTHER PUBLICATIONS

Brochure-Product. *ATROSTIM Phrenic Nerve Stimulator*. AtroTech Oy, P.O. Box 28, FIN-33721 Tampere, Finland, 2 pgs. (Jun. 2004).

Furman et al. *A Practice of Cardiac Pacing*. Permanent Pacemaker Implementation, Chapter 5, pp. 97-127. Futura Publishing Co., Inc., Mount Kisco, NY (1986).

Lupi et al. Effects of Right Ventricular Pacing on Intra-Left Ventricular Electromechanical Activation in Patients With Native Narrow QRS. *American Journal of Cardiology*, 2006;98:219-222.

Narula, M.D. *Longitudinal Dissociation in the His Bundle. Bundle Branch Block Due to Asynchronous Conduction Within the His Bundle in Man*. Circulation, vol. 56, No. 6, Dec. 1977.

Puech et al. *Narrowing and normalization of QRS by stimulation of the His bundle in complete left bundle branch block*. Scholarly Journal of the French Cardiology Society, vol. 72, No. 8, Aug. 1979. English translation thereof, followed by French publication.

Ravazzi et al. *Improvement of Interventricular Activation Time Using Biphasic Pacing Pulses at Different Sites on Right Ventricle Sepal Wall*. Progress in Biomedical Research, pp. 248-253 (Jun. 1999).

Saksena et al. *Electrical Therapy for Cardiac Arrhythmias*. Pacemaker Implantation Techniques, Chapter 9, pp. 173, 181-183, W.B. Saunders Co., Philadelphia, PA (1990).

Sweeney et al. Adverse Effect of Ventricular Pacing on Heart Failure and Atrial Fibrillation Among Patients With Normal Baseline QRS Duration in a Clinical Trial of Pacemaker Therapy for Sinus Node Dysfunction. *Circulation*, 2003;107:2932-2937.

Sweeney et al. Heart Failure During Cardiac Pacing. *Circulation*, 2006;113:2082-2088.

Tanabe et al. *Biventricular Pacing Worsened Dyssynchrony in Heart Failure Patient With Right-Bundle Branch Block*. Int'l Journal of Cardiology, in press 2008 (doi:10.1016/j.ijcard.2008.06.063).

"U.S. Appl. No. 12/147,317, Non Final Office Action mailed Dec. 28, 2010", 7 pgs.

"U.S. Appl. No. 10/004,695, Amendment and Response filed Mar. 9, 2004 to Non-Final Office Action mailed Dec. 22, 2003", 8 pgs.

"U.S. Appl. No. 10/004,695, Non-Final Office Action mailed Dec. 22, 2003", 6 pgs.

"U.S. Appl. No. 10/004,695, Notice of Allowance mailed Apr. 13, 2004", 7 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

"U.S. Appl. No. 10/745,302, Restriction Requirement mailed Aug. 12, 2005", 7 pgs.

"U.S. Appl. No. 11/300,242, Final Office Action mailed Aug. 4, 2009", 9 pgs.

"U.S. Appl. No. 11/300,242, Non-Final Office Action mailed Mar. 27, 2008", 8 pgs.

"U.S. Appl. No. 11/300,242, Response filed Feb. 4, 2010 to Final Office Action mailed Aug. 4, 2009", 11 pgs.

"U.S. Appl. No. 11/300,242, Response filed Apr. 2, 2009 to Restriction Requirement mailed Dec. 15, 2008", 8 pgs.

"U.S. Appl. No. 11/300,242, Response filed Sep. 26, 2008 to Non-

Final Office Action mailed Mar. 27, 2008", 10 pgs.
"U.S. Appl. No. 11/300,242, Restriction Requirement mailed Dec. 15, 2008", 10 pgs.
"U.S. Appl. No. 11/300,611, Amendment After Allowance Under 37 C.F.R. § 1.312 filed Feb. 9, 2009", 9 pgs.
"U.S. Appl. No. 11/300,611, Non-Final Office Action mailed Mar. 20, 2008", 7 pgs.
"U.S. Appl. No. 11/300,611, Notice of Allowance mailed Jan. 26, 2009", 7 pgs.
"U.S. Appl. No. 11/300,611, Response filed Sep. 22, 2008 to Non-Final Office Action mailed Mar. 20, 2008", 12 pgs.
"U.S. Appl. No. 11/300,611, Response to Rule 312 Communication mailed Feb. 26, 2009", 3 pgs.
"U.S. Appl. No. 12/147,293, Response filed Feb. 8, 2011 to Restriction Requirement mailed Oct. 8, 2010", 9 pgs.
"U.S. Appl. No. 12/147,293, Restriction Requirement mailed Oct. 8, 2010", 12 pgs.
"U.S. Appl. No. 12/147,339, Notice of Allowance mailed Dec. 22, 2010", 8 pgs.
"U.S. Appl. No. 12/147,339, Response filed Oct. 20, 2010 to Restriction Requirement mailed Oct. 8, 2010", 7 pgs.
"U.S. Appl. No. 12/147,339, Restriction Requirement mailed Oct. 8, 2010", 7 pgs.
"U.S. Appl. No. 12/147,356, Restriction Requirement mailed Oct. 12, 2010", 7 pgs.
"U.S. Appl. No. 12/147,356, Notice of Allowance mailed Feb. 10, 2011", 17 pgs.
"U.S. Appl. No. 12/147,356, Response filed Nov. 10, 2010 to Restriction Requirement mailed Oct. 12, 2010", 9 pgs.
"U.S. Appl. No. 12/147,369, Non-Final Office Action mailed Sep. 10, 2010", 10 pgs.
"U.S. Appl. No. 12/147,369, Response filed Feb. 10, 2011 to Non Final Office Action mailed Sep. 10, 2010", 7 pgs.
"U.S. Appl. No. 12/147,425, Non-Final Office Action mailed Sep. 15, 2010", 10 pgs.
"U.S. Appl. No. 12/147,425, Response filed Feb. 15, 2011 to Non-Final Office Action mailed Sep. 15, 2010", 8 pgs.
"Australian Application Serial No. 2005319498, First Examiner Report mailed May 27, 2010", 3 pgs.
"European Application Serial No. 05849548.2, Communication and Supplementary Partial European Search Report mailed Feb. 29, 2008", 8 pgs.
"European Application Serial No. 05849548.2, Communication mailed Jun. 9, 2009", 3 pgs.
"European Application Serial No. 05849548.2, Office Action mailed Dec. 20, 2010", 4 pgs.
"European Application Serial No. 05849548.2, Response filed Dec. 16, 2009 to Communication mailed Jun. 9, 2009", 10 pgs.
"European Application Serial No. 08772198.1, Office Action mailed Sep. 13, 2010", 6 pgs.
"European Application Serial No. 08781107, Response filed Sep. 22, 2010 to Invitation Rule 63(1)", 11 pgs.
"European Application Serial No. 08781107.1, Invitation Pursuant to Rule 63(1) EPC mailed Jul. 13, 2010", 3 pgs.
"European Application Serial No. 08781107.1, Communication dated Feb. 9, 2010", 2 pgs.
"European Application Serial No. 08781107.1, Extended European Search Report mailed Nov. 25, 2010", 6 pgs.
"European Application Serial No. 08781107.1, Response filed Mar. 5, 2010 to Communication dated Feb. 9, 2010", 2 pgs.
"European Application Serial No. 08796045.6, European Search Report mailed Sep. 21, 2010", 6 pgs.
"International Application Serial No. PCT/US05/45044, International Search Report mailed May 2, 2006", 1 pg.
"International Application Serial No. PCT/US05/45044, Written Opinion mailed May 2, 2006", 3 pgs.
"International Application Serial No. PCT/US08/68618, International Search Report mailed Nov. 26, 2008", 2 pgs.
"International Application Serial No. PCT/US08/68618, Written Opinion mailed Nov. 26, 2008", 6 pgs.
"International Application Serial No. PCT/US08/68627, International Search Report mailed Sep. 10, 2008", 1 pg.
"International Application Serial No. PCT/US08/68627, Written Opinion mailed Sep. 10, 2008", 4 pgs.
"International Application Serial No. PCT/US08/68630, International Search Report mailed Sep. 10, 2008", 1 pg.
"International Application Serial No. PCT/US08/68630, Written Opinion mailed Sep. 10, 2008", 4 pgs.
"International Application Serial No. PCT/US08/68632, International Search Report mailed Sep. 11, 2008", 2 pgs.
"International Application Serial No. PCT/US08/68632, Written Opinion mailed Sep. 11, 2008", 4 pgs.
"International Application Serial No. PCT/US08/68647, International Search Report mailed Sep. 22, 2008", 2 pgs.
"International Application Serial No. PCT/US08/68647, Written Opinion mailed Sep. 22, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2009/060293, Invitation to Pay Additional Fee mailed Dec. 18, 2009", 5 pgs.
"International Application Serial No. PCT/US2009/060293, International Search Report mailed Mar. 10, 2010", 6 pgs.
"International Application Serial No. PCT/US2009/060293, Written Opinion mailed Mar. 10, 2010", 10 pgs.
"Japanese Application Serial No. 2007-548289, Office Action mailed Nov. 24, 2010", (w/ English Translation), 7 pgs.
Barba-Pichardo, R., et al., "Permanent His-Bundle Pacing in Patients With Infra-Hisian trioventricular Block", *Rev Esp Cardiol.* 59(6), (Mar. 9, 2006), 553-558.
Bonanno, C., et al., "Effect on QRS Duration and Feasibility of Septal and Multisite Right entricular Pacing", *Cardiostimolazione*, 14(3), (Abstract Only), (Sep. 1996), p. 195.
Buckingham, Thomas A., et al., "Acute Hemodynamic Effects of Atrioventricular Pacing at Differing Sites in the Right Ventricle Individually and Simultaneously", *PACE*, 20[Pt I], (Apr. 1997), 909-915.
Cantu, F., et al., "Validation of Criteria for Selective His Bundle and Para-Hisian Permanent Pacin•", *PACE*, vol. 29, Dec. 2006 , 1326-1333.
Cantu, Francesco, et al., "A Methodical Approach to Validate Selective His Bundle and para-Hisian Permanent Pacing", [abstract] *Oasis*, (2006), 1 pg.
Catanzariti, D., et al., "Permanent His Bundle Pacing Does Not Induce Ventricular Dyssynchrony. An Echocardiographic Intrapatient Study of Comparison with Conventional Pacing", [abstract] *Oasis*, (2006), 1 pg.
Chudzik, Michal, "Ventricular Endocardial Right Bifocal Stimulation in Treatment of Severe Dilated Cardiomyopathy Heart Failure in Patients with Unsuccessful Biventricular Pacemaker Implantation", [abstract CP07] *Europace Supplements*, vol. 7, (May 2005), 1 pg.
Deshmukh, P., et al., "Permanent, Direct His-Bundle Pacing: A Novel Approach to Cardiac Pacing in Patients With Normal His-Purkinje Activation", *Circulation*, 101(8), (Feb. 29, 2000), 869-877.
Deshmukh, P. M., et al., "Direct His-Bundle Pacing: Present and Future", *PACE*, vol. 27, Part II, Jun. 2004 , 862-870.
El-Sherif, N., et al., "Normalization of Bundle Branch Block Patterns by Distal His Bundle Pacing: Clinical and Experimental Evidence of Longitudinal Dissociation in the Pathologic His Bundle", *Circulation*, 57(3), (Mar. 1978), 473-483.
Golia, P., et al., "Multisite Pacing of Right Ventricle in Heart Failure: Echocardiographic Evaluation", [Abstract] *Cardiostimolazione*, vol. 14 No. 3, (Sep. 1996), 5 pgs.
Grosfeld, M. J.W., et al., "Testing a New Mechanism for Left Interventricular Septal Pacing: The Transseptal Route", *Europace*, vol. 4, (Oct. 2002), 439-444.
Hummel, J. D., et al., "Augmentation of Cardiac Output by Anodal Pacing", [abstract] Circulation, 90(No. 4, Part 2, (Oct. 1994), p. 1-69.
Kavanagh, K. M., et al., "Monophasic Versus Biphasic Cardiac Stimulation: Mechanism of Decreased Energy Requirements", *PACE*, vol. 13, No. 10, (Oct. 1990), 10 pgs.

Kutarski, A., et al., "Factors Influencing Differences of RVA & RVOT Pacing Hemodynamic Effects", [abstract CP05] *Europace Supplements*, vol. 7, (May 2005), p. 288.

Kutarski, A., et al., "Right Ventricular Outflow Tract and Dual Site Right Ventricular Pacing—The Comparison With Apex Pacing", [Abstract CP08] *Europace Supplements*, vol. 7, (May 2005), p. 288.

Lazarus, A., et al., "Reduction in Energy Pacing Thresholds by Overlapping Biphasic Stimulation Versus Conventional Bipolar Pacing", *PACE*, vol. 21, (Nov. 1998), 6 pgs.

Manolis, Antonis S., "The Deleterious Consequences of Right Ventricular Apical Pacing: Time to Seek Alternate Site Pacing", *PACE*, vol. 29, (Mar. 2006), 298-315.

Mond, Harry G., et al., "The Right Ventricular Outflow Tract: The Road to Septal Pacing", *PACE*, vol. 30, (Apr. 2007), 482-491.

Morina-Vazquez, P., et al., "Cardiac Resynchronization Through Selective His Bundle Pacing in a Patient with the So-Called InfraHis Atrioventricular Block", *PACE*, vol. 28, (Jul. 2005), 726-729.

Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", *Journal of the American Colleqe of Cardiology*, 47(10), (May 16, 2006), 1938-1945.

Padeletti, Luigi, et al., "Physiologic Pacing: New Modalities and Pacing Sites", *PACE*, vol. 29, Supplement 2, (Dec. 2006), S73-S77.

Pastore, G., et al., "Different Degree of Ventricular Dyssyncrony Induced by Right Apical, Hissian and Para Hissian Ventricular Pacing", [abstract] *Oasis*, (2006), 1 pg.

Pastore, Gianni, et al., "Direct His-Bundle Pacing Preserves the Normal Left Activation Sequence: An Acute Echocardioqraphic Study", [abstract] *Oasis*, (2006), 1 pg.

Reddy, G. S., "Bundle of His Stimulation System", U.S. Appl. No. 61/045,168, filed Apr. 15, 2008, 37 pgs.

Scheinman, M. M., et al., "Long-Term His-Bundle Pacing and Cardiac Function", *Circulation*, 101(8), (2000), 836-837.

Schoenfeld, M. H., "Alternative Site Pacing to Promote Cardiac Synchrony: Has Conventional Pacing Become Unconventional?", *Journal of the American College of Cardiology*, 47(10), (2006), 1946-1948.

Sotobata, I., et al., "Population distribution of Frank-vectorcardiographic measurements of healthy Japanese men", *Jasanese Circulation Journal*, 39(8), (1975), 895-903.

Thakral, A, et al., "Effects of anodel vs. cathodal pacing on the mechanical performance of the isolated rabbit heart", *J. Appl Physiol.*, 89(3), (Sep. 2000), 1159-1164.

Tse, Hung-Fat, et al., "Selection of Permanent Ventricular Pacing Site: How Far Should We Go?", *Journal of the American College of Cardiology*, 48(8), (Sep. 26, 2006),.

Van Gelder, B. M., et al., "Hemodynamic Effect of RV Apex vs RV Septum Pacing in a Monoventricular and Biventricular Configuration in Patients with Heart Failure", [abstract CP06] *Europace Supplements*, vol. 7, (May 2005), p. 288.

Victor, F., et al., "A Randomized Comparison of Permanent Septal Versus Apical Right Ventricular Pacing: Short-Term Results", *Journal of Cardiovascular Electrophysiology*, vol. 17(3), (Mar. 2006), 238-242.

Winckels, S. K. G., et al., "High-Septal Pacing Reduces Ventricular Electrical Remodeling and Proarrhythmia in Chronic Atrioventricular Block Dogs", *Journal of the American College of Cardiology*, 50(9), (Aug. 28, 2007), 906-913.

Zanon, F., et al., "A Feasible Approach for Direct His-Bundle Pacing Using a New Steerable Catheter to Facilitate Precise Lead Placement", *Journal of Cardiovascular Electrophysiology*, 17(1), (Jan. 2006), 29-33.

Zanon, F., et al., "A New Technique for Direct His-Bundle Pacing: Acute and Mid-Term Electrical Data Results", [abstract] *Oasis*, (2006), 1 pg.

Zanon, F., et al., "Direct His Bundle Pacing Preserves Coronary Perfusion Compared With Right Ventricular Apical Pacing: A Prospective, Cross-Over Mid-Term Study", *Europace*, vol. 10, (2008), 580-587.

Zhang, Y., et al., "His Electrogram Alternans Reveal Dual-Wavefront Inputs Into and Longitudinal Dissociation Within the Bundle of His", *Circulation*, 104(7), (2001), 832-838.

"U.S. Appl. No. 11/300,242, Non Final Office Action mailed May 12, 2011", 9 pgs.

"U.S. Appl. No. 12/147,293, Notice of Allowance mailed Apr. 8, 2011", 12 pgs.

"U.S. Appl. No. 12/147,317, Examiner Interview Summary mailed Mar. 15, 2011", 3 pgs.

"U.S. Appl. No. 12/147,317, Response filed Jun. 27, 2011 to Non Final Office Action mailed Dec. 28, 2010", 11 pgs.

"U.S. Appl. No. 12/147,339, Notice of Allowance mailed Mar. 30, 2011", 9 pgs.

"U.S. Appl. No. 12/147,356, Notice of Allowance mailed Jun. 30, 2011", 15 pgs.

"U.S. Appl. No. 12/147,369, Notice of Allowance mailed Apr. 21, 2011", 7 pgs.

"U.S. Appl. No. 12/147,425, Notice of Allowance mailed Apr. 19, 2011", 8 pgs.

"U.S. Appl. No. 12/249,454, Non Final Office Action mailed Apr. 6, 2011", 8 pgs.

"U.S. Appl. No. 12/249,479, Non Final Office Action mailed Apr. 5, 2011", 11 pgs.

"U.S. Appl. No. 12/249,508, Restriction Requirement mailed Jun. 30, 2011", 6 pgs.

"U.S. Appl. No. 12/412,608, Non Final Office Action mailed May 26, 2011", 8 pgs.

"European Application Serial No. 05849548.2, Response filed Jun. 29, 2011 to Non Final Office Action mailed Dec. 20, 2010", 9.

"European Application Serial No. 08772198.1, Response filed Mar. 31, 2011 to Communication mailed Sep. 30, 2010", 11 pgs.

"European Application Serial No. 08781107.1, Response filed Jun. 14, 2011 to Communication mailed Dec. 14, 2010", 10 pgs.

"European Application Serial No. 08796045.6, Response filed Apr. 15, 2011 to Communication dated Oct. 8, 2010", 10 pgs.

"Japanese Application Serial No. 2007-548289, Final Office Action dated Aug. 2, 2011", 3.

"Japanese Application Serial No. 2007-548289, Response filed May 20, 2011 to Office Action mailed Nov. 24, 2010", 9 pgs.

"U.S. Appl. No. 11/300,242, Notice of Allowance mailed Jan. 24, 2012", 5 pgs.

"U.S. Appl. No. 11/300,242, Notice of Allowance mailed May 8, 2012", 6 pgs.

"U.S. Appl. No. 11/300,242, Response filed Sep. 12, 2011 to Non Final Office Action mailed May 12, 2011", 8 pgs.

"U.S. Appl. No. 12/147,317 , Response filed Apr. 11, 2012 to Final Office Action mailed Oct. 12, 2011", 8 pgs.

"U.S. Appl. No. 12/147,317, Final Office Action mailed Oct. 12, 2011", 6 pgs.

"U.S. Appl. No. 12/249,454, Examiner Interview Summary mailed Feb. 22, 2012", 3 pgs.

"U.S. Appl. No. 12/249,454, Final Office Action mailed Nov. 23, 2011", 8 pgs.

"U.S. Appl. No. 12/249,454, Response filed Apr. 2, 2012 to Final Office Action mailed Nov. 23, 2011", 12 pgs.

"U.S. Appl. No. 12/249,454, Response filed Aug. 30, 2011 to Non Final Office Action mailed Apr. 6, 2011", 14 pgs.

"U.S. Appl. No. 12/249,479, Final Office Action mailed Dec. 2, 2011", 8 pgs.

"U.S. Appl. No. 12/249,479, Response filed Apr. 2, 2012 to Final Office Action mailed Dec. 2, 2011", 9 pgs.

"U.S. Appl. No. 12/249,479, Response filed Aug. 30, 2011 to Non Final Office Action mailed Apr. 5, 2011", 12 pgs.

"U.S. Appl. No. 12/249,508, Notice of Allowance mailed Feb. 14, 2012", 7 pgs.

"U.S. Appl. No. 12/249,508, Notice of Allowance mailed Jun. 12, 2012", 7 pgs.

"U.S. Appl. No. 12/249,508, Notice of Allowance mailed Oct. 5, 2011", 9 pgs.

"U.S. Appl. No. 12/249,508, Response filed Aug. 30, 2011 to Restriction Requirement mailed Jun. 30, 2011", 8 pgs.

"U.S. Appl. No. 12/412,608, Final Office Action mailed Nov. 21, 2011", 6 pgs.

"U.S. Appl. No. 12/412,608, Notice of Allowance mailed Jun. 6, 2012", 7 pgs.

"U.S. Appl. No. 12/412,608, Response filed Apr. 18, 2012 to Final Office Action mailed Nov. 21, 2011", 7 pgs.
"U.S. Appl. No. 12/412,608, Response filed Sep. 26, 2011 to Non Final Office Action mailed May 26, 2011", 9 pgs.
"Australian Application Serial No. 2005319498, Response filed Feb. 21, 2011 to First Examiner Report mailed May 27, 2010", 11 pgs.
"Coating Process for Composite Implants" *Medical Materials Update*, vol. 1, No. 12, (Jan. 1995), 3 pgs.
"European Application Serial No. 08796045.6, Office Action mailed Jan. 4, 2012", 4 pgs
"European Application Serial No. 08796045.6, Response filed May 14, 2012 to Office Action mailed Jan. 4, 2012", 8 pgs.
"Implant Attaches to Bone by Chemical Bond", *Medical Materials Update*, vol. 4, No. 7, (Aug. 1997), 2 pgs.
"International Application Serial No. PCT/US2009/060293, International Preliminary Report on Patentability mailed Apr. 12, 2011", 10 pgs.
"International Application Serial No. PCT/US2009/088859, International Search Report mailed Jul. 5, 2010", 7 pgs.
"International Application Serial No. PCT/US2009/068859, Invitation to Pay Additional Fee mailed Apr. 15, 2010", 6 pgs.
"International Application Serial No. PCT/US2009/068859, Written Opinion mailed Jul. 5, 2010", 12 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.
"Japanese Application Serial No. 2007-548289, Office Action mailed Mar. 6, 2012", (w/ English Translation), 3 pgs.
"Japanese Application Serial No. 2007-548289, Response filed Jun. 4, 2012 to Office Action mailed Mar. 8, 2012", 3 pgs.
"Japanese Application Serial No. 2007-548289, Response filed Oct. 26, 2011 to Office Action mailed Aug. 3, 2011", (w/ English Translation of Amended Claims), 10 pgs.
"Victrex's PEEK Used for Dialysis Machines", *Medical Material's Update*, vol. 3, No. 3, (Apr. 1996), pp. 1-2.
Al-Khadra, A., et al., "The Role of Electroporation in Defibrillation", *Circulation Research*, 87(9), (Oct. 2000), 797-804.
Arcot-Krishnamurthy, S., et al., "Timing for His-Bundle Pacing", U.S. Appl. No. 13/277,617, filed Oct. 20, 2011, 40 pgs.
Avitall, B., et al., "Iontophoretic Transmyocardial Drug Delivery. A Novel Approach to Antiarrhythmic Drug Therapy", *Circulation*, 85(4), (1992), 1582-1593.
Barton A. J., et al., "Bacterial Adhesion to Orthopedic Implant Polymers", *J. Biomed. Mat. Res.*, 30(3), Mar. 1996), 403-410.
Chiu, L., et al., "Method for One-Click Deployment and or Configuration of Real-Time Software System Modifications", Provisional U.S. Appl. No. 60/558,921, filed Arp. 2, 2004, 8 pgs.
Dong, Y., et al., "His-Bundle Capture Verification and Monitoring", Provisional U.S. Appl. No. 61/328,248, filed Apr. 27, 2010, 40 pgs.
Flynn, David M, et al "Extendable and Retractable Lead Having a Snap-Fit Terminal Connector", U.S. Appl. No. 11/173,664, filed Jul. 1, 2005, 53 pgs.
Genc. S., et al., "Methodology for Locking Feature Selection in Integral Snap-Fit Assembly", *Proceedincs of DETC '97, 1997 ASME Engineering Technical Conferences*, (Sep. 1997), 1-11.
Ha, S. W., et al., "Plasma-Sprayed Hydroxylapatite Coating on Carbon Fibre Reinforced Thermoplastic Composite Materials", *J. Mater. Sci. Mater. Med.*, vol. 6, No. 6-7, (1994), pp. 481-484.
Ingle, Frank, et al., "Lead Motion Sensing Via Cable Microphonics", Provisional U.S. Appl. No. 61/359,430, filed Jun. 29, 2010, 52 pgs.
Jockisch, K. A., et al., "Biological Response to Chopped-Carbon-Fiber-Reinforced Peek", *J. Biomed. Mater. Res.*, vol. 26, No. 2, (1992), 133-146.
Kanno, S., et al., "Establishment of a simple and practical procedure applicable to therapeutic angiogenesis", *Circulation*, 99(20), (May 25, 1999), 2682-2687
Kaye, D. M., et al., "Frequency-dependent activation of a constitutive nitric oxide synthase and regulation of contractile function in adult rat ventricular myocytes", *Circulation Research*, 78(2) (Feb. 1996), 217-224.
Knapp, C. P, et al., "Snap Fit Terminal Connector", U.S. Appl. No. 09/184,226, filed Nov. 2, 1998, 39 pgs.
Labhasetwar, V., et al., "Iontophoresis for Modulation of Cardiac Drug Delivery in Dogs", *Proc. Natl. Acad. Sci. USA* 92(7), (Mar. 28, 1995), 2612-2616.

Lin, T. W., et al., "Glass Peek Composite Promotes Proliferation and Osteocalcin of Human Osteoblastic Cells", *J. Biomed. Mater. Res.*, vol. 36, No. 2, (1997), 137-144.
MacNair, R., et al., "The Response of Primary Rat and Human Osteoblasts and an Immortalized Rat Osteoblast Cell Line to Orthopaedic Materials: Comparative Sensitivity of Several Toxicity Indices", *J. Mater. Sci, Mater. Med.*, vol. 8, No. 2, (1997), 105-111.
Mansourati, J., et al "Left ventricular-based pacing in patients with chronic heart failure: comparison of acute hemodynamic benefits according to underlying heart disease", *Eur J. Heart Fail.*, 2(2), (Jun. 2000), 195-199.
Meyer, M. R., et al., "Long-Term Durability of the Interface in FRP Composites After Exposure to Simulated Physiologic Saline Environments", *J. Biomed. Mater. Res.*, 28(10), (1994), 1221-1231.
Morrison, C., at al., "In Vitro Biocompatibility Testing of Polymers for Orthopaedic Implants Using Cultured Fibroblasts and Osteoblasts", *Biomaterials*, vol. 16, No. 13, (1995), pp. 987-992.
Qu, J, et al., "HCN2 overexpression in newborn and adult ventricular myocytes: distinct effects on gating and excitability", *Circ. Res.*, vol. 89(1), (Jul. 6, 2001), e8-e14.
Qu, J, et al., "Sympathetic innervation alters activations of pacemaker current (If) in rat ventricle", *J. Physiol*, 526 Pt 3. (Aug. 1, 2000), 561-569.
Shi, W, et al., "Distribution and prevalence of hyperpolarization-activated cation channel (HCN) mRNA expression in cardiac tissues", *Cir. Res.*, vol. 85(1), (Jul. 9, 1999), e1-e6.
Soyer, J., et al., "Experimental Characterisation of a Carbon/PEEK Hip Prothesis in Fatigue", *Chirurgie*, 121, (1996), 658-663.
Takatsuki, et al., "Clinical Implications of "pure" Hisian pacing in addition to para-Hisian pacing for the diagnosis of supraventricular tachycardia", *Heart Rhythm* 3 (12), (Dec. 8, 2006), 1412-1418.
Wang, S. C.-J., et al., "Improved Method and System for Managing Voice Prompt Recordings Prior to Deployment", Provisional U.S. Appl. No. 60/532,271, filed Dec. 23, 2003, 12 pgs.
Wenz, L. M., et al., "In Vitro Biocompatibiiity of Polyetheretherketone and Polysulfone Composites", *J. Biomed. Mater. Res.*, vol. 26, No. 2, (1990), 207-215.
Yu, H., et al., "MinK-related peptide 1: A beta subunit for the HCN ion channel subunit family enhances expression and speeds activation", *Circ. Res.*, 88(12). (Jun. 22, 2001), e84-e87.
Zhu Q., et al., "Methods, Devices and Systems for Cardiac Pacing Therapies Using Intrinsic Activity", Provisional U.S. Appl. No. 61/139,117, filed Dec. 19, 2008, 22 pgs.
U.S. Appl. No. 13/223,919, filed Sep. 1, 2011, Systems, Devices and Methods Relating to Endocardial Pacing for Resynchronization.
U.S. Appl. No. 13/217,776, filed Aug. 25, 2011, Systems, Devices and Methods for Monitoring Efficiency of Pacing.
U.S. Appl. No. 13/282,163, filed Oct. 26, 2011, Circuit-Based Devices and Methods for Pulse Control of Endocardial Pacing in Cardiac Rhythm Management.
U.S. Appl. No. 13/216,969, filed Aug. 24, 2011, Endocardial Pacing Relating to Conduction Abnormalities.
U.S. Appl. No. 13/139,951, filed Jan. 6, 2012, Devices, Methods, and Systems Including Cardiac Pacing.
U.S. Appl. No. 13/094,416, filed Apr. 26, 2011, His-Bundle Capture Verification and Monitoring.
U.S. Appl. No. 13/404,814, filed Feb. 24, 2012, His Capture Verification Using Electro-Mechanical Delay.
"U.S. Appl. No. 11/300,242, Notice of Allowance mailed Aug. 24, 2012", 7 pgs.
"U.S. Appl. No. 12/147,317, Notice of Allowance mailed Jul. 2, 2012", 7 pgs.
"U.S. Appl. No. 12/249,454, Non Final Office Action mailed Sep. 4, 2012", 8 pgs.
"U.S. Appl. No. 12/249,479, Non Final Office Action mailed Sep. 4, 2012", 7 pgs.
"International Application No. PCT/US2011/033944, International Preliminary Report on Patentability mailed Nov. 8, 2012", 9 pgs.
"Japanese Application Serial No. 2007-548289, Office Action mailed Nov. 6, 2012", With English Translation, 3 pgs.
U.S. Appl. No. 13/645,464, filed Oct. 4, 2012, Ventricular Pacing.
U.S. Appl. No. 13/650,444, filed Oct. 12, 2012, Methods, Devices and Systems for Single-Chamber Pacing using a Dual-Chamber Pacing Device.
US 6,875,206, 04/2005, Ponzi (withdrawn)

* cited by examiner

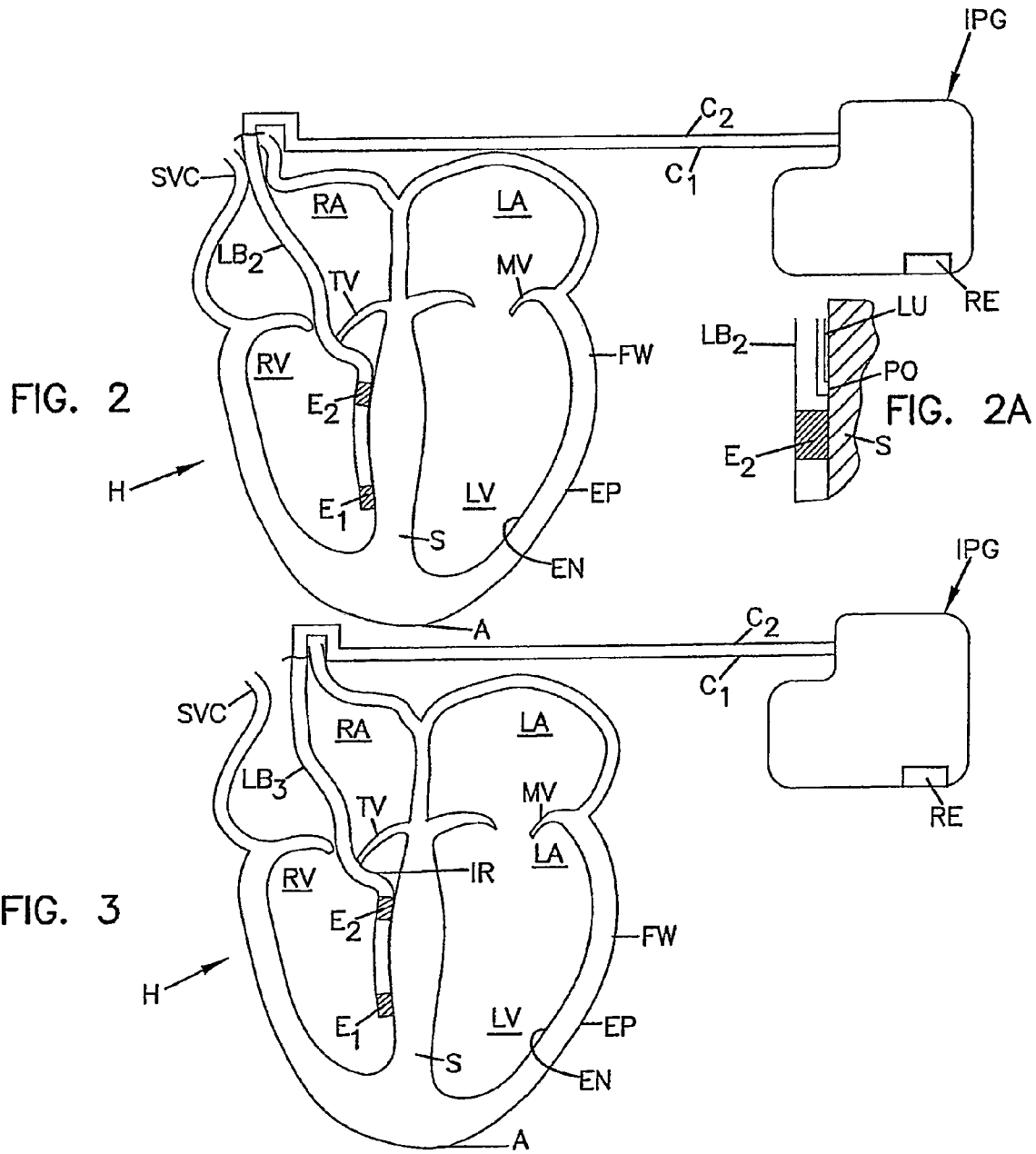

FIG. 17
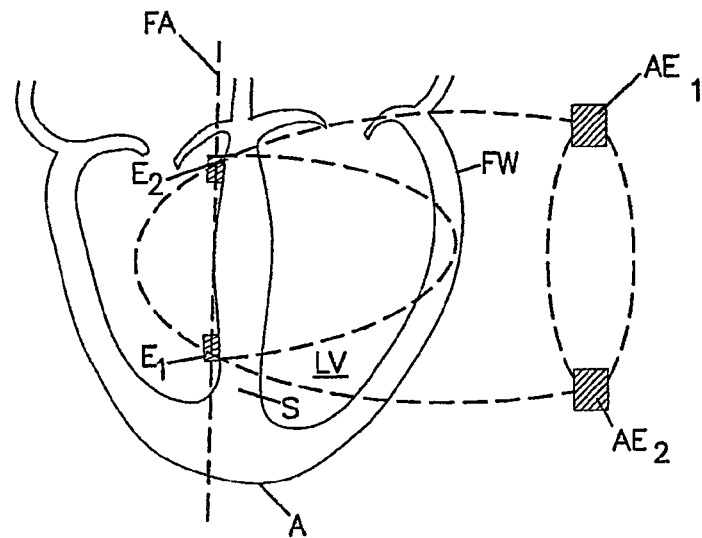
FIG. 18
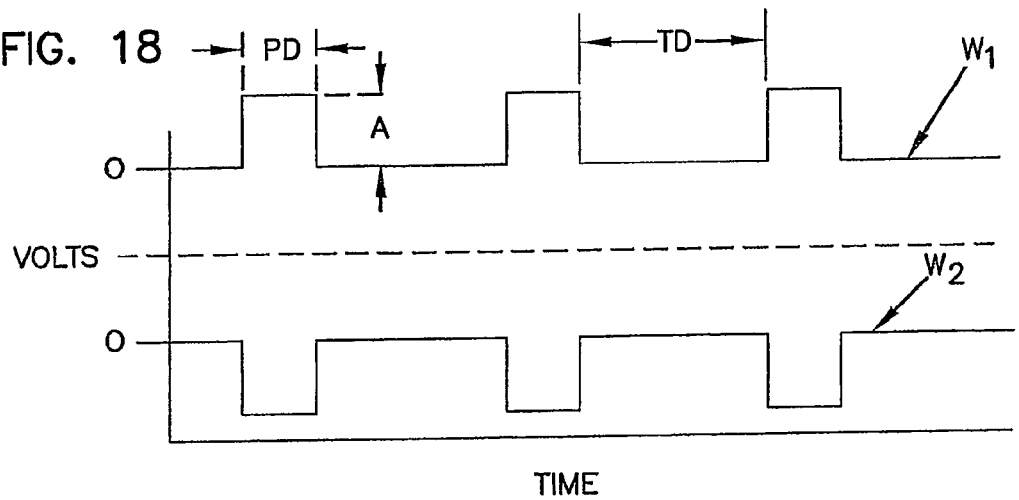
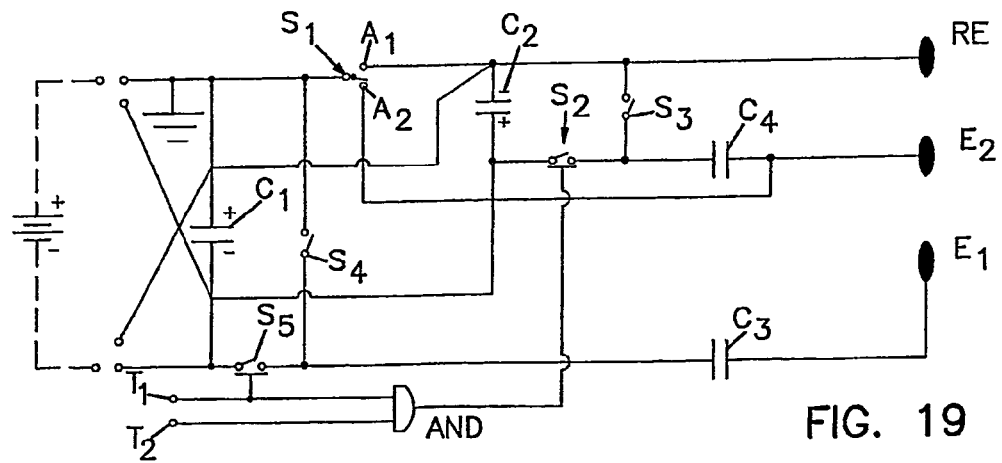
FIG. 19

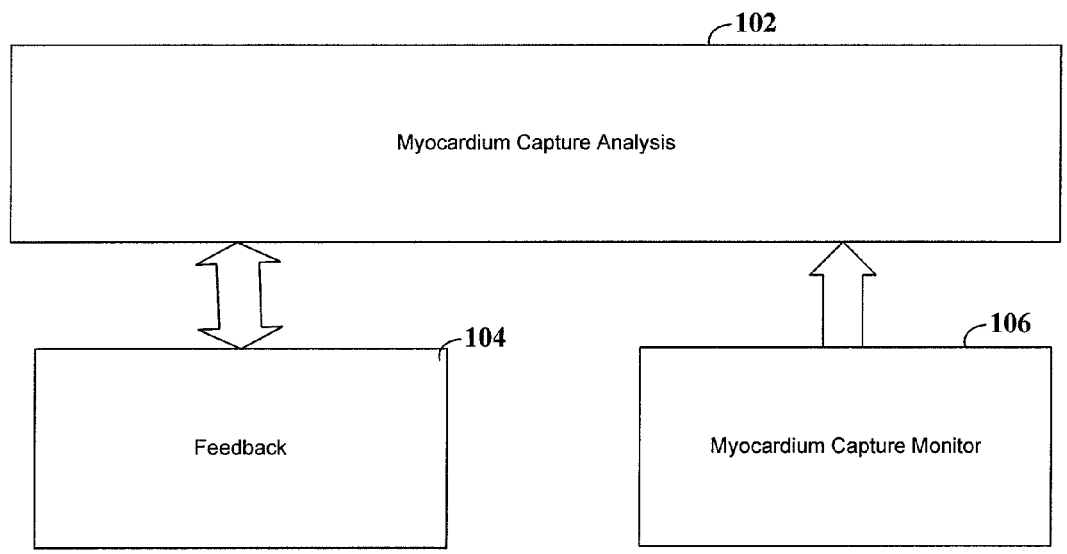
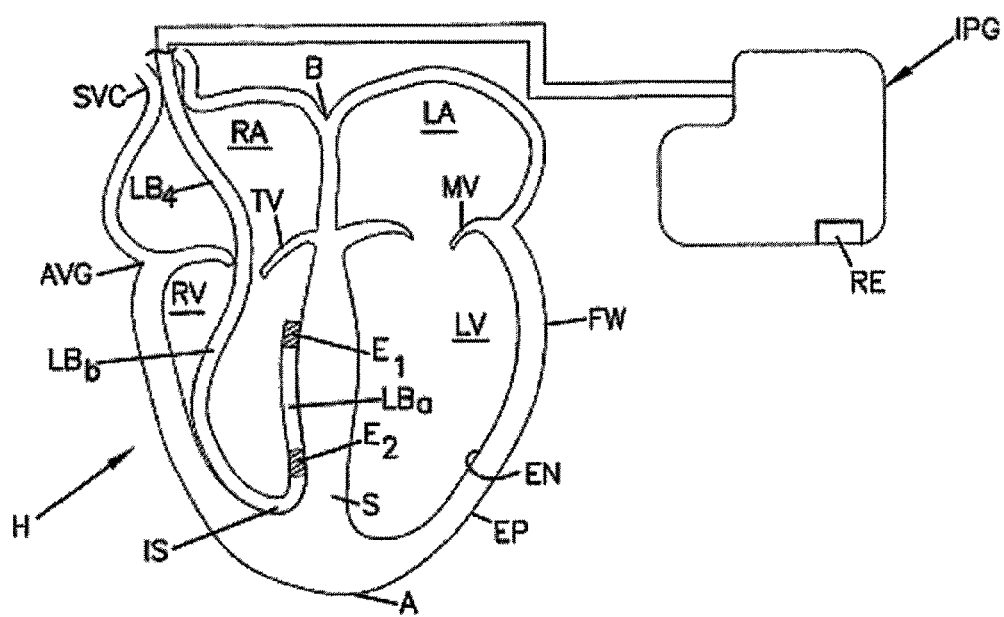
FIG. 21

FIG. 23A  FIG. 23B  FIG. 23C
 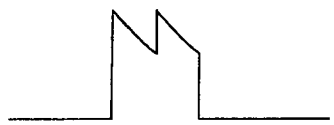 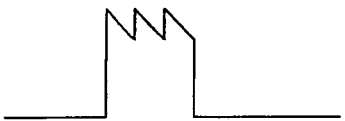
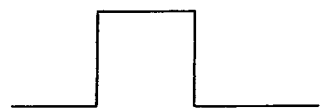
FIG. 23D Tridimensional Anatomical Scheme of the Union of the AV Node, the Para-Hisian and Hisian Regions

METHODS, DEVICES AND SYSTEMS FOR CARDIAC RHYTHM MANAGEMENT USING AN ELECTRODE ARRANGEMENT

RELATED PATENT DOCUMENTS

This patent document claims the benefit, under 35 U.S.C. §119(e), of U.S. Provisional Patent Applications concurrently filed on Jun. 29, 2007, to Qingsheng Zhu and identified by the following Ser. Nos.: 60/947,308 (Endocardial Pacing For Resynchronization), and 60/947,310 (Directable Sheath Arrangement For Ventricular Resynchronization), and of U.S. Provisional Patent Application identified by Ser. No. 61/020,511 (A Cardiac Stimulation Catheter With Two Contacting Electrodes To The Cardiac Tissue And Its Connections To The Stimulator) filed on Jan. 11, 2008 to Qingsheng Zhu et al. This patent document is also a continuation-in-part of and claims priority under 35 U.S.C. §120 both to U.S. patent application Ser. No. 11/300,611, now U.S. Pat. No. 7,512,440, filed Dec. 13, 2005 (Ventricular Pacing) to Daniel Felipe Ortega et aL and to U.S. patent application Ser. No. 11/300,242, filed Dec. 13, 2005 (Pacemaker Which Reestablishes Or Keeps The Physiological Electric Conduction Of The Heart And A Method Of Application) to Daniel Felipe Ortega et al., which in turn claim priority to Argentine Patent Application Ser. No. 20040104782, filed Dec. 20, 2004 (A New Pacemaker Which Reestablishes Or Keeps The Physiological Electric Conduction Of The Heart And A Method Of Application), to Daniel Felipe Ortega et al. Each of these patents documents is incorporated by reference in their entirety.

FIELD OF THE INVENTION

This invention generally relates to systems, devices and methods relating to cardiac monitoring and treatments such as ventricular pacing. More particular aspects of this invention concern use of an catheter-like electrode arrangement for improving heart function while pacing of a patient's left and right ventricles by one or more electrodes residing in the patient's right ventricle.

BACKGROUND

Pacemakers are perhaps the most well known devices that provide chronic electrical stimulus, such as cardiac rhythm management. Pacemakers have been implanted for medical therapy. Other examples of cardiac stimulators include implantable cardiac defibrillators (ICDs) and implantable devices capable of performing pacing and defibrillating functions. Such implantable devices provide electrical stimulation to selected portions of the heart in order to treat disorders of cardiac rhythm. An implantable pacemaker paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some pacing devices synchronize pacing pulses delivered to different areas of the heart in order to coordinate the contractions. Coordinated contractions allow the heart to pump efficiently while providing sufficient cardiac output. Clinical data has shown that cardiac resynchronization, achieved through synchronized biventricular pacing, results in a significant improvement in cardiac function. Cardiac resynchronization therapy improves cardiac function in heart failure patients. Heart failure patients have reduced autonomic balance, which is associated with LV (left-ventrical) dysfunction and increased mortality.

Commonly treated conditions relate to the heart beating too fast or too slow. When the heart beats too slow, a condition referred to as bradycardia, pacing can be used to increase the intrinsic heart rate. When the heart beats too fast, a condition referred to as tachycardia, pacing can be used to reduce the intrinsic heart rate by, for example, inhibiting electrical signals used to generate a contraction of the heart.

When pacing for bradycardia, percutaneously placed pacing electrodes are commonly positioned in the right-side chambers (right atrium or right ventricle) of the heart. Access to such chambers is readily available through the superior vena cavity, the right atrium and then into the right ventricle. Electrode placement in the left ventricle is normally avoided, where access is not as direct as in right ventricle placement. Moreover, emboli risk in the left ventricle is greater than in the right ventricle. Emboli which might develop in the left ventricle by reason of the electrode placement have direct access to the brain via the aorta from the left ventricle. This presents a significant risk of stroke. Pacing of both the right atrium and right ventricle was developed. Such dual chamber pacing resulted in better hemodynamic output than right ventricle-only pacing. In addition to treating bradycardia, dual chamber pacing maintained synchrony between the chambers.

Recent clinical evidence suggests that conventional ventricular pacing from the right ventricle creates asynchronous contraction of the left and right ventricles, thereby resulting in inefficient mechanical contraction and reduced hemodynamic performance. Long term right ventricular pacing has even been found to be associated with an increased risk of developing or worsening heart failure.

SUMMARY

The present invention is directed to use of a steerable device and method for overcoming the above-mentioned challenges and others. The present invention is exemplified in a variety of implementations and applications, many of which involve tools and methods helpful, or particularly suited, for certain cardiac conditions advantaged by ventricular pacing, as exemplified by ventricular pacing of the right and left ventricles from a lead in the right ventricle and as may be used, among other applications, to facilitate mechanically and/or electrically synchronous contractions for resynchronization.

Some aspects of the present invention, presented herein as mere examples and without limitation, are useful for pacing and/or mapping by delivering pulses to a cardiac site to improve heart function. According to certain aspects of the present invention, an electrode arrangement is adapted for positioning one or more electrodes along the septum of the right ventricle of the heart.

Certain aspects involve pacing and/or mapping by delivering pulses to a cardiac site useful for improving heart function as measured, e.g., by QRS width, fractionation, late LV activation timing, mechanical synchronicity of free wall and septal wall, effective throughput/pressure, or a combination thereof. In one embodiment, a catheter arrangement includes a fixation mechanism to attach the catheter arrangement to heart tissue, individually-addressable (i.e., capable of providing distinct signals) electrodes for providing pacing signals to the heart tissue, and an elongated structure that supports the fixation mechanism and the electrodes. The elongated structure is used to direct an end thereof to a target region in the right ventricle, and deliver an electrical pacing signal to different portions within the target region of the heart when the fixation mechanism is operative to attach to heart tissue and also when the fixation mechanism is not attaching the catheter arrangement to heart tissue.

An aspect of the present invention is directed to a catheter, and uses thereof, for capturing myocardium of a heart by delivering pacing signals to a location in the heart. The location is near a His Bundle of the Heart. The catheter has a proximal end for interfacing with an electrical pacing signal source and a distal end. The distal end includes a fixation mechanism that attaches the catheter to heart tissue and first and second electrodes. Each electrode is individually addressable for providing pacing signals to the heart tissue and also arranged to physically contact the heart tissue when the fixation mechanism is attached to the heart tissue.

Consistent with embodiments of the present invention, a method is implemented for delivering pacing signals to a heart using a catheter having electrodes on a distal end of the catheter. Within the right ventricle, the electrodes are placed in physical contact with the septal wall near a His Bundle of the heart. The placement is accomplished by attaching the catheter to heart tissue at a location so as to provide increased heart function when pacing. A pacing signal is provided via the electrodes. The signal is sufficient to capture myocardium of the heart.

Aspects of the present invention is directed to an arrangement for use in capturing myocardium of a heart. Capture can be obtained by delivering pacing signals to a target region in a right ventricle. In some instances the target region is near the septum of the heart and distal from an apex of the right ventricle. The arrangement has a catheter like structure with a fixation mechanism to attach the catheter arrangement to heart tissue. Individually-addressable electrodes provide pacing signals to the heart tissue and are arranged to directly contact heart tissue when the fixation mechanism is attached to heart tissue. An elongated structure supports the fixation mechanism and the individually-addressable electrodes. The structure directs an end of the elongated structure to the target region in the right ventricle delivers an electrical pacing signal to different portions within the target region of the heart via the individually-addressable electrodes. In one mode in which the fixation mechanism attaches the catheter arrangement to heart tissue while delivering pacing signals. In another mode the fixation mechanism does not attach the catheter arrangement to heart tissue while delivering pacing signals.

In another specific embodiment, the electrodes are used to capture the myocardium for re-synchronization of the left and right ventricles by providing first and second signal components having opposite polarity on respective electrodes. Placement of the electrodes is accomplished by adjusting the electrode placement, testing and monitoring the effectiveness of the placement and selecting the electrode placement in response to the results of the monitoring.

Aspects of the present invention are also directed to specialized electrodes and other features for improving delivery of pacing signals to heart tissue. In a specific instance, the electrodes are arranged to improve the contact area between the electrode and the heart tissue. For example, the electrodes can include one or more conductive portions that are porous, raised and/or nanostructures, and reasonable combinations thereof.

In a more specific embodiment a directable sheath is used in combination with feedback regarding the effectiveness of the capture of the myocardium corresponding to the current position of the one or more electrodes.

In one embodiment, a hollow sheath with at least one electrode at the distal end is used to allow mapping and pacing inside the heart. The inner diameter of the sheath is larger than the diameters of the pacing lead and may have an active fixation mechanism. A homeostasis valve is built into the sheath to stop the blood outflow while allowing easy passing through of a pacing lead. A certain curvature is built into the distal end that would allow easy and stable contact with the endocardium, especially for the right ventricular septum region.

In another embodiment, the hollow sheath contains a directable guide wire, which can be manipulated through a mechanical thumb wheel apparatus to change the sheath curvature.

In yet another embodiment, an inner sheath is movably disposed within an outer sheath. At least a distal end portion of the inner sheath has stiffness greater than that of at least a distal end portion of the outer sheath. The distal end portion of the outer sheath includes a deflectable distal end and at least one electrode at the distal end. The method further involves advancing the inner sheath through the outer sheath toward the deflectable distal end of the outer sheath, and longitudinally displacing the distal end portion of the inner sheath relative to the deflectable distal end of the outer sheath to alter a shape of the deflectable distal end.

In other embodiments, the distal electrode(s) sheath can be connected to an external stimulator described for locating a suitable stimulation site for resynchronizing the left ventricle. Once located, an active fixation pacing lead can be inserted inside the sheath and attached to the septal myocardium.

In specific applications and embodiments, this heart function is measured by QRS width, fractionation, late LV activation timing, mechanical synchronicity of free wall and septal wall, effective throughput/pressure, and by any combination thereof.

Other specific applications and aspects, which can be implemented alone or in combination, include: determining a pacing (voltage) threshold, beyond the capture threshold, to improve heart function; delivering pulses of opposite polarity to achieve such heart-function improvement; bi-ventricular pacing from a lead in the right ventricle for such improved heart function; delivering pulses of opposite polarity at a site near the His bundle; electrode-based His-pacing, without penetrating the myocardium; generating and/or delivering multiple pacing profiles, e.g., by iterating through different pacing profiles, including a pacing profile that delivers pulses of opposite polarity and another pacing profile; delivering a pacing profile to generate a synchronous contraction of the septal wall and free wall of the LV from a RV (right-ventricle) pacing location; and treating one or more of distal LBBB (left bundle branch block) and/or diffuse LBBB by pacing at a site near the His bundle.

The skilled artisan will appreciate that the His bundle is also known as the atrioventricular (AV) bundle and previously characterized as an area of heart muscle cells that provide electrical conduction for transmitting the electrical impulses from an area near the AV node (located between the atria and the ventricles). In connection with implementations of the present invention, it has been discovered that certain cells in and around the His bundle can be manipulated to respond to certain electrical stimulus in unexpected ways. Some aspects and implementations of the present invention facilitate modulation of the His bundle to improve the heart condition in unexpected ways.

Implementations of the present invention take a wide variety of forms, e.g., ranging from devices, systems, methods of using and manufacturing such devices and systems, to computer-accessible data (computer executable instructions and other input and output data) useful for implementing such methods, devices and systems. Many of these implementations involve such tools and steps relating to the above-listed aspects.

As specific examples of other such implementations, the present invention can be implemented in the form of methods, devices and arrangements of devices for monitoring cardiac operation and modifying cardiac operation, e.g., for cardiac treatment. In one such specific example embodiment, one or more of the above aspects involves placement of an electrode arrangement (including at least one electrode) in a RV of the heart for capturing the myocardium for re-synchronization of the left and right ventricles. This is achieved by providing first and second signal components having opposite polarity on respective electrodes. The contraction of the heart is monitored and used in determining the position of the electrodes. In more specific embodiments, the electrode arrangement is located in the sweet spot (locus) for achieving resynchronization, in the septal part of the RV endocardium. Anodal pacing of one of the electrodes can be used with respect to a reference voltage in the body of the patient to achieve resynchronization or a synchronous contraction during pacing of the heart. Polarities may be switched as appropriate (e.g., once every few hours) to avoid anodal block (the rise of stimulation thresholds that occurs after continuous anodal stimulation at the anodal electrode).

In other specific examples, implementations involve pacing from the right ventricle to treat LBBB, diffuse-distal block characterized by large QRS width (e.g., QRS>120 ms) and fractionated ECG (electrocardiograph or electrocardiogram) signals. Consistent therewith, a specific method involves the use of a pacing profile having opposite-polarity pulses (relative to body common) delivered for a cardiac capture (defined as the presence of contractions in the heart in direct response to electrical stimulation signals from an external source). In various contexts, such a pacing profile is referred to herein as an "Xstim" pacing profile or simply as Xstim.

One such Xstim pacing profile includes the use of two electrodes that are oppositely charged with respect to a reference electrode. In various implementations, the electrodes are spatially disparate. The pulses can be provided, relative to one another, in phase, out of phase, offset and overlapping, offset not overlapping with no delay between pulses, offset not overlapping with a delay between pulses or biphasic with a single electrode near the His bundle.

In yet other specific examples, implementations involve devices and methods for pacing and/or mapping at a location near the bundle of His in the right ventricle. As indicated above, the location is characterized by one or more of improvement in QRS width, improvement in fractionation or movement of late activated LV location forward in the QRS. In one instance, the pacing is delivered with a single pacing lead and both ventricles are captured. In some instances, the pacing can use an Xstim pacing profile.

According to yet other embodiments, the present invention involves pacing at a location that is determined as follows. An intrinsic or baseline ECG reading is taken. A pacing lead is placed in the RV near the bundle of His. A pacing signal is delivered to the pacing lead. In a specific instance, the pacing signal is an Xstim pacing profile. A pacing ECG signal is taken. Comparisons are made between one or more of the QRS width, fractionated QRS and the timing of a late activated region of LV relative to the QRS. The position of the probe is changed and the pacing and comparison steps are repeated as necessary. The lead can then be fixed at the appropriate location.

In other embodiments, the present invention involves selection of a pacing profile and placing a lead in the RV at or near the His bundle to deliver a plurality of pacing profiles. Heart function is recorded (e.g., using an ECG), and a suitable pacing profile is then selected for treatment.

According to another embodiment, pacing devices and methods of using such devices involve a catheter that delivers a lead that has two electrodes. In certain implementations thereof, the catheter is adapted to contact near the His bundle. A pacing profile (with two opposite voltages, referenced to body common) is delivered to the electrodes. The electrodes are individually addressable and spatially disparate. In a specific instance, one electrode is located at or near the distal tip of the lead and the other is located between the distal tip and the proximal end of the lead. Some embodiments allow for the use of more than two electrodes. Also, one or more electrodes may be used to sense heart function.

According to another embodiment, a catheter is adapted and used to facilitate adjustment of the location along the septal wall of the right ventricle. The catheter is designed for delivering a pacing profile and for subsequent adjustment of a delivery site for the pacing profile. This embodiment can be useful for a pace-sense-adjust procedure which, in some instances, is iterated until a location is determined for achieving the improved heart function.

As previously indicated, the above-discussed aspects and examples and not to be treated as limiting the scope or teachings of the disclosure herein. The skilled artisan would appreciate that, partly based on the various discoveries identified herein, the present invention can be embodied in many ways including but not limited to the above the above-discussed aspects and examples.

BRIEF DESCRIPTION OF THE DRAWINGS

The present invention may be more completely understood in consideration of a detailed discussion of various example embodiments, described in accordance with the present invention, as presented hereinafter in connection with the following figures, each of which is consistent with the present invention:

FIG. 2 is the view of FIG. 1 showing electrodes in contact with a septal wall;

FIG. 2A is a cross-sectional view of an electrode lead showing a mechanism for attachment of an electrode to a septal wall;

FIG. 3 is the view of FIG. 1 showing an electrode lead formed, in part, from shape memory alloys for urging electrodes against a septal wall;

FIG. 17 is the view of FIG. 15 with a reference electrode replaced by two polarized electrodes;

FIG. 18 is a graphical representation of pulsed waveforms to be applied by first and second electrodes of the various embodiments;

FIG. 19 is an electrical schematic for a portion of a pacing output desired in a pulse generator with programmable pacing configurations;

FIG. 21 is a system for determining optimal placement of the electrodes;

FIGS. 23A, 23B, 23C and 23D depict a graphical representation of pulse to be applied by the electrodes of the various embodiments;

Figure 1:
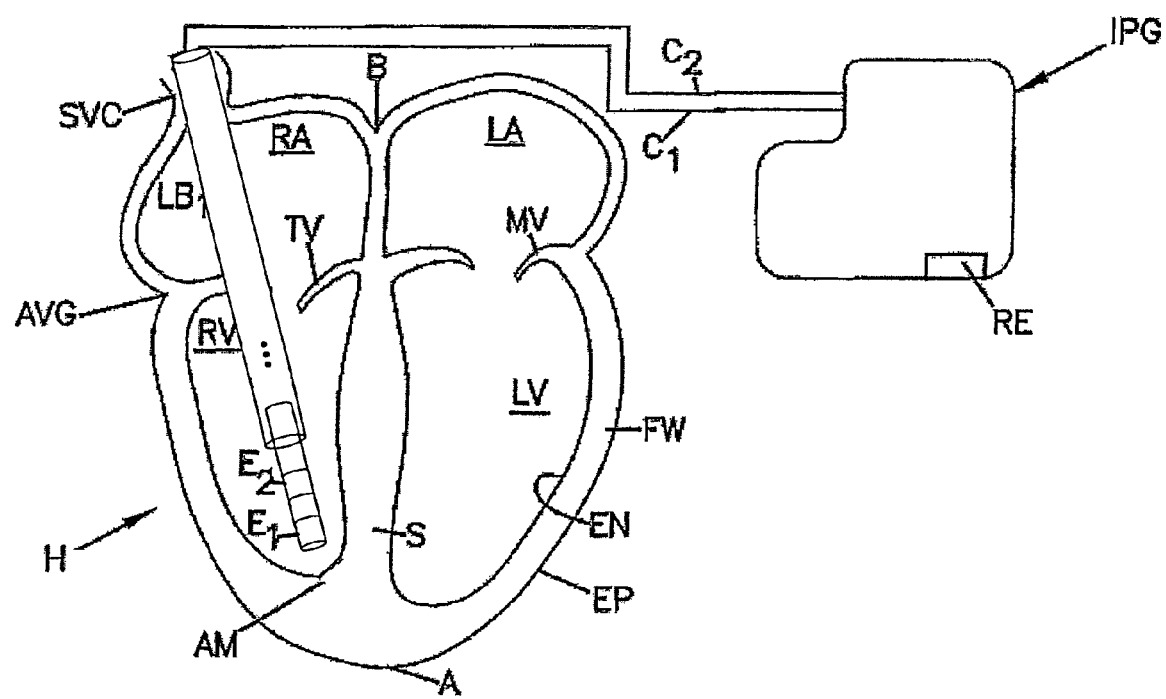
FIG. 1 is a schematic cross-sectional view of the heart showing relevant anatomical features and schematically showing a catheter with pacing electrodes in the right ventricle and a subcutaneously placed implantable pulse generator.

While the invention is amenable to various modifications and alternative forms, various embodiments have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for approaches to pacing of the right and left ventricles from a lead in the right ventricle. In certain implementations, the invention is used to facilitate mechanically and/or electrically synchronous contractions for resynchronization (possibly due to conduction abnormalities such as LBBB) where the left ventricle has regained its ability to rapidly contract and/or to synchronize contractions of cardiac muscle of the septum and respective free wall(s). While the present invention is not necessarily limited to such applications, various aspects of the invention may be appreciated through a discussion of various examples using this context.

Consistent with specific embodiments and various discoveries realized in connection with the present invention, heart function can be improved by pacing and/or mapping by delivering pulses to a cardiac site, where the heart function is indicated or measured, e.g., by QRS width, fractionation, late LV activation timing, mechanical synchronicity of free wall and septal wall, effective throughput/pressure, and/or by any combination thereof. Certain methods and specific aspects consistent with such embodiments of the present invention concern directing a catheter-type device for delivering pulses to a cardiac site where the improved heart function involves: determining a pacing (voltage) threshold, beyond the capture threshold, to improve heart function; delivering pulses of opposite polarity to achieve such heart-function improvement; bi-ventricular pacing from a lead in the right ventricle for such improved heart function; delivering pulses of opposite polarity at a site near the His bundle; electrode-based His-pacing, without penetrating the myocardium; generating and/or delivering multiple pacing profiles, e.g., by iterating through different pacing profiles, including a pacing profile that delivers pulses of opposite polarity and another pacing profile; delivering a pacing profile to generate a synchronous contraction of the septal wall and free wall of the LV from a RV (right-ventricle) pacing location; and treating one or more of distal LBBB (left bundle branch block) and/or diffuse LBBB by pacing at a site near the His bundle.

Various embodiments of the present invention include stimulation catheters, systems and methods that employ two or three electrodes. In specific embodiments of the present invention, the most distal two electrodes are located at the tip of the catheter. An optional third electrode can be located in a number of places, such as on the lead body some distance from the first pair or even located between the pairs.

As a specific example of an unexpected result, it has been discovered that His bundle pacing and/or para-Hisian pacing can be used to treat patients exhibiting a variety of cardiac abnormalities previously thought to be unsuitable for His bundle pacing (e.g., large QRS complexes due to distal left bundle blocks or diffuse left bundle blocks). It has also been discovered that implantation complexities (e.g., duration and/or invasiveness) can be beneficially affected by the use of specific devices, systems and placement methods.

According to an example embodiment of the present invention, a specialized stimulation profile is used to capture a synchronous contraction of the left and right ventricles. The stimulation profile is provided to a lead in the right ventricle. The lead placement and stimulation profile are selected in response to sensed heart function during the pacing. In particular, the lead placement and stimulation profile are determined based upon more than whether the placement/profile results in capture (e.g., QRS width or late activation site timing). In certain instances, this can result in pacing voltages/profiles not otherwise believed to be desirable (e.g., voltages derived from criteria other than the capture threshold and/or His bundle pacing without penetrating the surrounding (fibrous) tissue with a pacing lead).

The understanding of various implementations of the present invention can be facilitated with a discussion of existing pacing, implantation and related procedures and devices. While a substantial number of differences exist between various embodiments of the present invention and such existing pacing, the present invention does not exclude implementations that include aspects of existing pacing. Quite to the contrary, aspects of the present invention are particularly useful for implementing in conjunction with existing pacing methods and devices. Accordingly, a number of embodiments of the present invention provide the flexibility to be useful when combined with existing implementations, some of which are discussed hereafter.

Combined pacing of the right ventricle and right atrium has been performed by advancing two electrode leads through the superior vena cava into the right atrium. The first of these terminated at one or more electrodes which were attached to the endocardium of the atrium. The second lead (also having one or more electrodes) was advanced into the right ventricle with the electrode attached to the endocardium of the right ventricle.

Such dual chamber pacing was not without complications. The use of two leads resulted in a doubling of volume of the vasculature (e.g., the superior vena cava and jugular vein) occupied by such leads. Further, attachment of an electrode to the atrial wall was unreliable.

The problems of the dual chamber pacing led to the development of so-called "single pass" leads. Such leads have both the atrial and ventricle electrodes on a common lead.

An example of a single pass lead, for pacing both the right ventricle and right atrium, is taught in U.S. Pat. No. 6,230,061 B1 to Hartung issued May 8, 2001. The lead of the '061 patent is described as a floating lead in that the lead and electrodes are not attached to the walls of the heart. In one embodiment of the '061 patent (FIG. 4A), two electrodes in the right atrium pace the right atrium. In a second embodiment (FIG. 4B), an electrode resides in the right ventricle to add right ventricular pacing. As will be described, the '061 patent describes an oppositely polarized electrode (which may be exposed on a subcutaneously placed implantable pulse generator).

It is believed that the design of the '061 patent has not enjoyed great commercial success. This is believed to be due, at least in part, to the separate development of smaller profile leads and more reliable atrial attachment techniques. Both of these developments address the problems of dual chamber pacing otherwise addressed by the '061 patent.

When treating for tachycardia (fast heart rate), electrical pulses are used to disrupt a contraction of the heart. This may be effective at reducing the heart rate by disrupting the abnormally fast pulses generated by cardiac dysfunction tissue.

Congestive heart failure (CHF) patients suffer from low left ventricular output. CHF is an extremely serious and progressive disease. While drug treatments exist, they may delay but do not stop or reverse the disease.

CHF patients face a progression of a debilitating condition which drastically alters lifestyle and will ultimately be fatal in the absence of heart transplant. Unfortunately, many patients do not qualify for such transplants and the available number of donor hearts is inadequate to treat those who do qualify.

Many CHF patients have low left ventricular output due to a mismatch between contractile forces produced by muscles of the left and right ventricles' free wall (the external wall of the left and right ventricles) and the opposing septum (the wall dividing the right and left ventricles). Ideally, the free wall and septum contract in synchrony during systole to urge blood through the aortic valve. When out of synchrony, the septal wall may be contracting while the free wall is relaxed. Instead of urging blood flow, at least a portion of the contractile energy of the septum is wasted.

The mismatch of free wall and septal contractility is believed to be due to disorders in the electrical conduction systems of the heart. This conduction system includes the A-V node (heart tissue between the atria and the ventricles that conducts contractile impulses from the atria to the ventricles), the bundle of His and the Purkinje fibers.

Located at the upper end of the septum, the sinus node creates the synchronized neurally-mediated signal for cardiac pacing. These signals are conducted by the specialized fibers comprising the A-V node and the bundle of His (extending along the length of the septum) and further conducted to the muscle of the heart through the Purkinje fibers. The Purkinje fibers originate in the septum and extend through the apex of the heart and to the exterior walls of the heart including into and up the free wall of the left and right ventricles.

In a healthy heart, the signal flow from the A-V node to the free wall of the left and right ventricles is rapid to ensure the free wall and septum contract in synchrony. For example, a stimulating signal may flow to the free wall in about 70-90 milliseconds. In patients with conduction abnormalities, this timing may be significantly delayed (to 150 milliseconds or more) resulting in asynchronous contraction.

In some patients, the conduction path through the Purkinje fibers may be blocked. The location of the block may be highly localized (as in the case of so-called "left bundle branch block" or LBBB) or may include an enlarged area of dysfunctional tissue (which can result from infarction). In such cases, all or a portion of the free wall of the left and/or right ventricles is flaccid while the septum is contracting. In addition to contributing to asynchronous contraction, the contraction force of the free wall is weakened.

To address asynchronous contraction, CHF patients can be treated with cardiac pacing of the left ventricle. Such pacing includes applying a stimulus to the septal muscles in synchrony with stimulation applied to the muscles of the free wall of the left ventricle. While infracted tissue will not respond to such stimulus, non-infracted tissue will contract thereby heightening the output of the left ventricle by re-synchronizing the contraction. Accordingly, treatment of CHF is often directed re-synchronization of the myocardium, whereas other ventricular pacing solutions, such as tachycardia and bradycardia, treat heart rate issues.

The prior art has developed various techniques for accomplishing left ventricle stimulation. For various reasons the techniques may not be ideal. For example, such pacing may result in wide QRS complexes or emboli formation. Thus, endocardial-positioned electrodes in the left ventricle are avoided. However, electrodes can be placed on the epicardial surface of the heart through surgical placement. The epicardial electrodes are positioned on the free wall of the left ventricle and are paced in synchrony with electrodes placed near the septum in the right ventricle.

Since epicardial electrodes require a surgical placement, the patient is subjected to two procedures: percutaneous placement of right ventricle electrodes (normally performed in a catheter lab by an electrophysiologist); and surgical placement of epicardial electrodes on the left ventricle (normally placed by a cardiac surgeon in a surgical suite). Such dual procedures are a burden on medical resources.

Percutaneous procedures have been developed for placement of an electrode to stimulate the free wall of the left ventricle. In such a procedure, an electrode lead is advanced through the coronary sinus. Part of the venous system, the coronary sinus extends from the right atrium and wraps around the heart on or near the epicardial surface and partially overlies the left ventricle free wall. In this percutaneous procedure, the electrode remains positioned in the coronary sinus overlying the left ventricle free wall with the lead passing through the coronary sinus and through the right atrium to the implantable pulse generator.

Unfortunately, a coronary sinus electrode is frequently less than optimal. The portion of the free wall most directly influenced by the electrode is the tissue directly underlying the coronary vein at the location of the electrode. For many patients, this may not be the location of the free wall that benefits the most from a stimulating therapy. Accordingly, the resulting therapy is sub-optimal. Also, some patients may have an extremely small-diameter coronary sinus or the coronary sinus may have such a tortuous shape that percutaneous positioning of an electrode within the coronary sinus is impossible or very difficult. Not uncommonly, advancing a lead from the right atrium into the coronary sinus is extremely time-consuming. Even if successful, such a procedure consumes significant health care resources (including precious catheter lab time). Finally, there are now up to three leads passing through and occupying the space of the superior vena cava (i.e., leads for the electrodes in the right ventricle, right atrium and the coronary sinus). U.S. patent application Publ. No. 2005/0125041 published Jun. 9, 2005 shows (in FIG. 1 thereof) three leads passing through a superior vena cava with one lead residing in the right atrium, one in the right ventricle and one passing through the coronary sinus to the left ventricle.

Attempts at pacing the left ventricle by pacing stimulation in the right ventricle have been suggested. U.S. Pat. No. 6,643,546 B2 to Mathis et al. dated Nov. 4, 2003 describes a lead with an array of electrodes along its length. The lead is placed in the right atrium and extended through the right ventricle, along the septal wall, and into the pulmonary artery. The concept requires that multiple electrodes from the array be pulsed simultaneously at significantly high voltages to produce an adequate electrical field to stimulate the LV septum. The current output from the pulse generator and battery will be very high due to the multiplicity of electrodes and high pacing voltages. Such high output will cause a clinically unacceptable product lifespan and may facilitate electrode corrosion and/or dissolution issues. Since a large number of electrodes and supporting electronics are needed to implement such a therapy delivery mechanism, it is not known yet whether it is practically feasible, not to mention that it is very complicated both in terms of device design/manufacturing as well as clinical practice. No published reports known to this date have demonstrated the functional as well as clinical benefits for this multiple electrode stimulation approach in the right ventricle.

As will be described with reference to one embodiment, the present invention is directed to a left ventricle pacing system and method which does not require epicardial pacing electrodes or pacing electrodes in a coronary sinus or a coronary vein. As will be described, the present invention includes electrodes in the right ventricle near the septal wall. These electrodes create a pulsed electrical field which stimulates both the septum and at least a portion of the free wall of the left and right ventricles. The present invention achieves these objectives without requiring excessive energy demands or power consumption.

Generally, the aspects of the present invention are directed to a method and apparatus for providing right-ventricle stimulation to re-synchronize a contraction of the musculature of the septum and free wall of the left and right ventricles to create coordinated contraction of the septum and free wall. Careful placement of the stimulating electrodes in the right ventricle is used to produce synchronous contractions of the left and right ventricles. In a particular instance, the right ventricle may be captured along with re-synchronization of the left and right ventricles from a single stimulus point or while maintaining the synchrony of the activation and contraction of the left and right ventricles (in the case that the patient required pacing and did not have an asynchronous contraction without pacing). Using various embodiments of the present invention, patients that have an asynchronous contraction of the heart (either the left or the right ventricles or both) can be resynchronized.

In another instance, pacing for patients having bradycardia, tachycardia or other rhythm management, may be improved by improving upon the asynchronous contraction that often occurs due to the electrical impulse artificially introduced that is not propagating through the normal conduction system of the heart (His-Purkinje system).

Consistent with embodiments and applications of the present invention, an electrode is carefully placed at the His bundle site ("His Pacing") by screwing in the electrode to get into or beside the bundle itself or by positioning the electrode at a site where the bundle gets to the endocardial surface (denoted supra as EN). Previous His-pacing efforts (to maintain synchronous contractions that would be otherwise lost due to conventional RV pacing for rate support) have been very burdensome largely because finding this very small region in the right ventricle has been very difficult, and the effort is generally time-consuming, expensive and extremely complex even with modern tools and imaging techniques. Further complicating such procedures is the lack of knowledge regarding the long-term stability of placing a lead in this location. Pacing the distal segment of the His bundle has also been shown to remove left bundle block (LBBB) in patients with a proximal lesion of the bundle. His pacing, however, is currently contraindicated in patients with a distal lesion of the His bundle or with an intraventricular conduction defect (IVCD), in patients with diffuse peripheral block (at the distal His or diffuse in the Pukinje fibers), and in patients with advanced HF (NYHA class II to IV) and conduction defects. Accordingly, His pacing is used only in a very small subset (<0.01%) of the patients that require ventricular pacing for either Sick Sinus Syndrome, AV block or other Bradyarrhythmia indications by an extremely small group of physicians.

It has also been discovered that correct placement of the stimulating electrodes along the septum can sometimes allow for re-synchronization of contractions of left-ventricle myocardium using relatively low voltages and may also result in improved QRS width, reduced fractionation, and/or improved timing of a late-activation site in the LV. It has also been discovered that the region in the septum where this effect takes place is larger and easier to find when particular methods are used. One such method includes the use of a waveform herein referred to as a Xstim waveform, where two pulses of opposite polarity are applied. The Xstim waveform, generally speaking, is the application of the two pulses of opposite polarity at the same time, or nearly the same time, such that both pulses are associated with the same capture (beat) of the heart.

In many patients the pacing region is located near the location where the His bundle passes close to the endocardial surface of the right ventricle. But in patients with more diffuse block and heart failure, it may move down in the septum towards the apex of the right ventricle. It has also been discovered that careful selection of the waveform may allow for effective pacing using lower voltages, thereby simplifying the design of the output circuits in the pacemaker and the delivery electrodes. It has further been discovered that the desired pacing effect can also be achieved by a single pulse of sufficient amplitude, usually much higher than the amplitude required by the Xstim waveform, and therefore presenting a much higher risk of diaphragmatic and/or phrenic nerve stimulation. It has further been discovered that the amplitude required to achieve the effect is more often lower when that pulse is of anodal nature versus a negative pulse (referenced to the body).

In one embodiment, each electrode may be selectively and independently used to stimulate a synchronous contraction. The voltages for each electrode are varied to determine the voltage threshold necessary to produce ventricular capture. In various implementations, discussed in more detail hereafter, the voltage threshold can be determined using criteria other than (or in addition to) whether ventricular capture is produced (e.g., improved heart function). Low average stimulation voltage and current may be obtained by selecting the electrode that has the lowest effect threshold (effect refers to resynchronization effect or to maintaining synchrony of the contraction during pacing effect).

In connection with the various drawing figures and relevant discussions, the following disclosures are incorporated herein by reference in their entirety: U.S. Pat. No. 6,230,061 B1 to Hartung issued May 8, 2001, for details of a cardiac pacemaker with localization of the stimulating pulses and U.S. Pat. No. 6,907,285 to Denker, et al., dated Jun. 14, 2004, for details of a wireless defibrillation system; U.S. patent application Publ. No. 2004/0153127 published Aug. 5, 2004 for details related to the use of a microstimulator in the proximity of at least one anatomical structure to produce muscular contractions; U.S. Pat. No. 6,643,546 B2 to Mathis et al. dated Nov. 4, 2003, for details related to the treatment of congestive heart failure.

As mentioned above, aspects of the present invention are directed to improving heart function as indicated by one or more of several measurable characteristics. The discussion and illustrations presented in connection with FIGS. 21-50 provide examples and related results for one or more of these and other aspects of the present invention. These aspects can be implemented in various combinations. To fully appreciate some of these aspects and the related discoveries, the following discussion of FIGS. 1-20 presents related discussion as well as various features that are optional to other embodiments, such as those illustrated and discussed in connection with FIGS. 21-50.

The present invention may be practiced with currently commercially available electrode leads and can also be enhanced with specially designed leads. FIG. 1 illustrates the invention in practice with one such lead. As is the conventional usage for referencing relative direction, the terms "left" and "right" are used herein with reference to the patient's perspective. The terms "upper" and "lower" and similar terms such as "up" or "down" are used with reference to the base B of the heart being high and the apex A of the heart H being a lower end.

In connection with various embodiment of the present invention, FIG. 1 illustrates approaches for pacing of the right and left ventricles from a lead in the right ventricle in a manner consistent with the above discussed aspects. As one such example, with Xstim pacing profiles being delivered on electrodes $E_1$ and $E_2$, heart function can be improved by pacing and/or mapping to delivering such pulses to a cardiac site. Such pacing/mapping can also be used to determine a pacing (voltage) threshold, beyond the capture threshold, to improve the heart's function. Such an approach can also be used to provide bi-ventricular pacing from a lead in the right ventricle for such improved heart function.

In FIG. 1, a patient's heart H is schematically shown in cross-section. The heart H includes the upper chambers of the right atrium RA and left atrium LA. The lower chambers are the right ventricle RV and left ventricle LV. Of the various venous vessels opening into the right atrium RA, only the superior vena cava SVC is shown. Also, of the various heart valves, only the mitral valve MV (separating the left atrium LA from the left ventricle LV) and the tricuspid valve TV (separating the right atrium RA from the right ventricle RV) are shown. The septum S separates the right and left ventricles RV, LV and the free wall FW of the left ventricle LV is separately labeled. The surface of the heart wall tissue opposing the chambers is the endocardium and is labeled as EN. The exterior surface of the heart is the epicardium and is labeled EP. Not shown are coronary vessels of the heart or the pericardium surrounding the heart H.

As a specific embodiment, FIG. 1 includes an electrode lead in an embodiment where signals are delivered via a dual (inner and outer) sheath catheter and shown as having a lead body $LB_1$ and exposed electrodes $E_1$ and $E_2$. The first electrode $E_1$ is positioned near the distal tip of the lead body $LB_1$. The second electrode $E_2$ is positioned more proximally on the lead body $LB_1$. At the distal end, an attachment mechanism AM (such as a passive fixation design with tines or an active fixation design with a metallic helix) is shown for securing the first electrode $E_1$ to the musculature of the heart H. The spacing of electrodes $E_1$, $E_2$ could be greater or smaller than that of convention pacing electrodes permitting positioning of the first electrode $E_1$ at the apex of the right ventricle RV and the second electrode $E_2$ in the right ventricle RV near the tricuspid valve TV. It is noted that conventional leads with convention spacing have been used with the first or distal electrode attached to the septum (e.g., by a helix attachment HA as shown in FIG. 7A).

According to various embodiments of the present invention, the position of electrodes $E_1$ and $E_2$ is determined by monitoring and analyzing the effectiveness of the pacing. In one example, an electrocardiogram (ECG) is used to monitor the cardiac waveform. The electrode position may be incrementally adjusted and the feedback from the ECG can be compared for each position. In a specific example, the QRS width is used in such a comparison. Another parameter that may be considered includes the angle of the vectocardiogram. For example, the analysis of the vectocardiogram may be viewed in terms of normalization of the vectocardiogram. For further information on vectorcardiographic measurements and normalization, reference can be made to, Sotobata I, Okumura M, Ishikawa H, Yamauchi K.; *Population distribution of Frank-vectorcardiographic measurements of healthy Japanese men*. Jpn Circ J. 1975 August; 39(8):895-903, which is fully incorporated herein by reference. In another example, the efficiency of the contraction can be ascertained by monitoring the synchrony of the contraction using two-dimensional echocardiography. In still another example, the efficiency of the contraction can be ascertained by monitoring the coronary sinus electrogram to determine the time delay that the activation wave front has between the pacing stimuli (or the resulting QRS complex) until a left ventricular activation is detected at the coronary sinus or any other (late activation) structure of the left ventricle. This may be accomplished using an electrophysiology-style catheter or any other catheter with one or more electrodes close to its tip. In one instance, the goal is to minimize the time delay.

In one embodiment, the lead body $LB_1$ is flexible and includes a bio-compatible, electrically insulating coating surrounding first and second conductors $C_1$, $C_2$ separately connected to the first and second electrodes $E_1$, $E_2$. In the various Figures, the lead bodies are broken at a line at the SVC to reveal the internal conductors $C_1$, $C_2$ extending to an implantable pulse generator IPG. In fact, the conductors $C_1$, $C_2$ are contained within the material of the lead body $LB_1$ along their length. The term "implantable pulse generator IPG" is intended to include pacemakers, implantable converter defibrillators (ICD) and cardiac resynchronization therapies (CRT), all known in the art.

The proximal end of the lead body terminates at a pin connector (not shown) as is customary. The pin connector has exposed electrical contacts uniquely connected to each of the conductors $C_1$, $C_2$. The pin connector may be connected to the pulse generator IPG so as to be releasable and with the exposed contacts making electrical connection with unique contacts of the circuitry of the pulse generator IPG.

It will be appreciated that the prior art contains numerous examples of cardiac leads for placement in a chamber of the heart where the leads have, as described above, two or more electrodes spaced along a length of the lead, attachment mechanisms such as passive or active fixation and conductors and connector pins as described. The current invention is not limited to pacing leads only, but rather is equally deployable with prior art ICD leads where it is customary to contain at least two electrodes in the RV. Such leads are selected of biocompatible material and treated (such as sterilized) for chronic placement in the patient.

The implantable pulse generator IPG is a small metallic container sealed for implantation in the patient and protecting internal circuitry. Commonly, such pulse generators are placed subcutaneously (e.g. in a dissected space between the skin and muscle layers of the patient). For cardiac pacing, such pulse generators are positioned in the upper chest on either the left or right front side of the patient near a shoulder. However, placement need not be so restricted and such pulse generators could be placed in any convenient location selected by the physician.

Pulse generators contain internal circuitry for creating electrical impulses which are applied to the electrodes after the lead is connected to the pulse generator. Also, such circuitry may include sensing and amplification circuitry so that electrodes $E_1$, $E_2$ may be used as sensing electrodes to sense and have the IPG report on the patient's electrophysiology.

The lead may be introduced to the vasculature through a small incision and advanced through the vasculature and into the right atrium RA and right ventricle to the position shown in FIG. 1. Such advancement typically occurs in an electrophysiology lab where the advancement of the lead can be visualized through fluoroscopy.

The pulse generator contains a battery as a power supply. With subcutaneous placement, replacement of a battery is possible. However, improvements in battery designs have resulted in longer-lasting batteries with the benefit of reducing the frequency of battery replacement. Alternatively, such batteries may be rechargeable in situ.

The pulse generator circuitry controls the parameters of the signals coupled to the electrodes $E_1$, $E_2$. These parameters can include pulse amplitude, timing, and pulse duration by way of example. The internal circuitry further includes circuit logic permitting reprogramming of the pulse generator to permit a physician to alter pacing parameters to suit the need of a particular patient. Such programming can be affected by inputting programming instructions to the pulse generator via wireless transmission from an external programmer. Pulse generators commonly include an exposed contact on the exterior of the generator housing. Such pulse generators may also be partially covered with an insulator, such as silicone, with a window formed in the insulator to expose a portion of the metallic housing which functions as a return electrode in so-called unipolar pacing. In bipolar pacing, the window is not necessary. Most commonly, the electrode is connected by the circuitry of the housing to an electrical ground.

While an implantable pulse generator is described in one embodiment, the pulse generator may be external and coupled to the electrodes by percutaneous leads or wireless transmission. For example, a control of an implanted electrode is known for phrenic nerve stimulation and is described more fully in a product brochure, "ATROSTIM PHRENIC NERVE STIMULATOR", AtroTech Oy, P.O. Box 28, FIN-33721, Tampere, Finland (June 2004). The Atrostim device sends signals from an external controller to an implanted antenna.

External pacing devices are typically used for providing temporary pacing therapy. Aspects of the current invention are also believed to have advantages for this application as critically-ill patients requiring emergency, temporary pacing may also suffer further from asynchronous cardiac contraction associated with conventional RV pacing. If desired, an external unit can be used to test a patient's suitability for the treatment. Patients who benefit from the therapy can then receive an implantable pulse generator for longer-term use.

FIG. 2 illustrates a lead body $LB_2$ in the right ventricle RV with the electrodes $E_1$, $E_2$ directly placed on the septal wall S and held in place against the septal wall through any suitable means. For example, FIG. 2A illustrates one embodiment for attachment of an electrode against the septal wall. The lead body $LB_2$ is shown as having an internal lumen LU with a port PO near an electrode (e.g., electrode $E_2$). Any suitable attachment mechanism (such as a pigtail guide wire or an injected bio-adhesive) can be passed through the lumen LU and port PO to fix the electrode $E_2$ in abutment against the septal wall S. Further, a guide catheter could also be used in moving the implantable lead to assist in the mapping of the optimal location of the septum.

FIG. 3 illustrates the electrodes $E_1$, $E_2$ against the septal wall S but without requiring an attachment mechanism. Instead, an intermediate region (IR) of the lead body $LB_3$ is formed of shaped memory material (such as nitinol) to assume an S-shaped configuration and urge the electrodes $E_1$, $E_2$ against the septal wall S.

Figure 4:
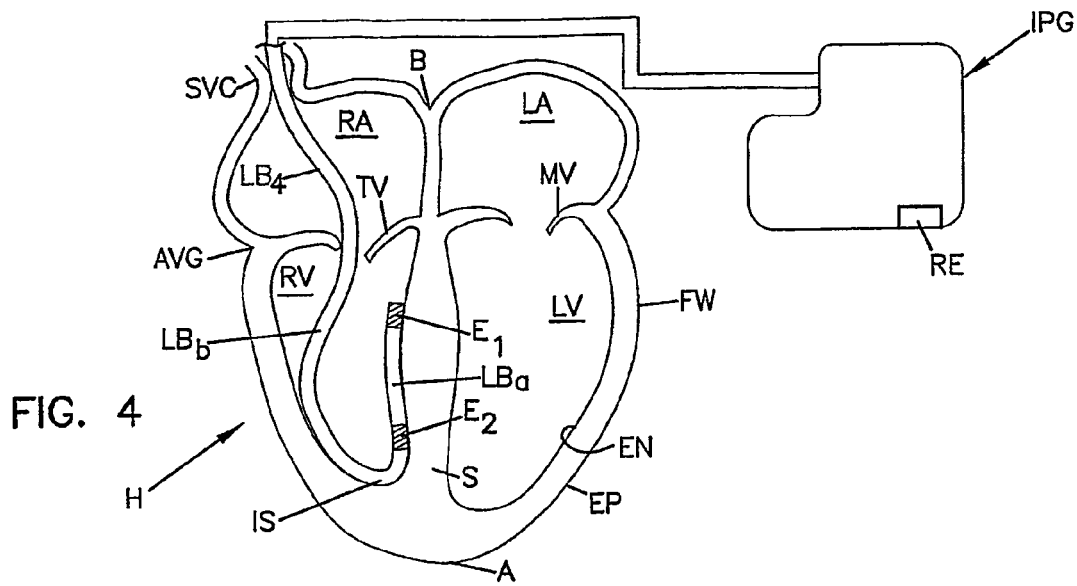
FIG. 4 is the view of FIG. 1 showing a further embodiment of an electrode lead for urging electrodes against a septal wall.

In FIG. 4, the lead body $LB_4$ has two components $LB_a$, $LB_b$ joined by an intermediate section IS which may be formed of any elastomeric material (such as a shaped memory material).

The intermediate section (IS) is biased to urge the two components $LB_a$, $LB_b$ into collinear alignment. With the intermediate section IS placed against the apex of the right ventricle (RV), the bias of the intermediate section IS urges the electrodes $E_1$, $E_2$ against the septal wall S.

Figure 5:
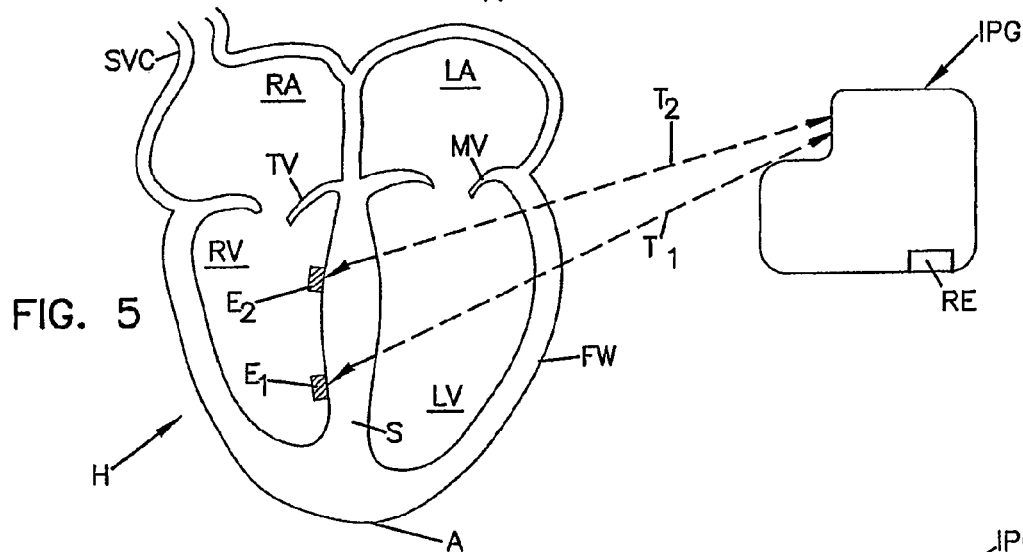
FIG. 5 is the view of FIG. 1 showing electrodes on a septal wall and energized by wireless transmission.
Figure 6:
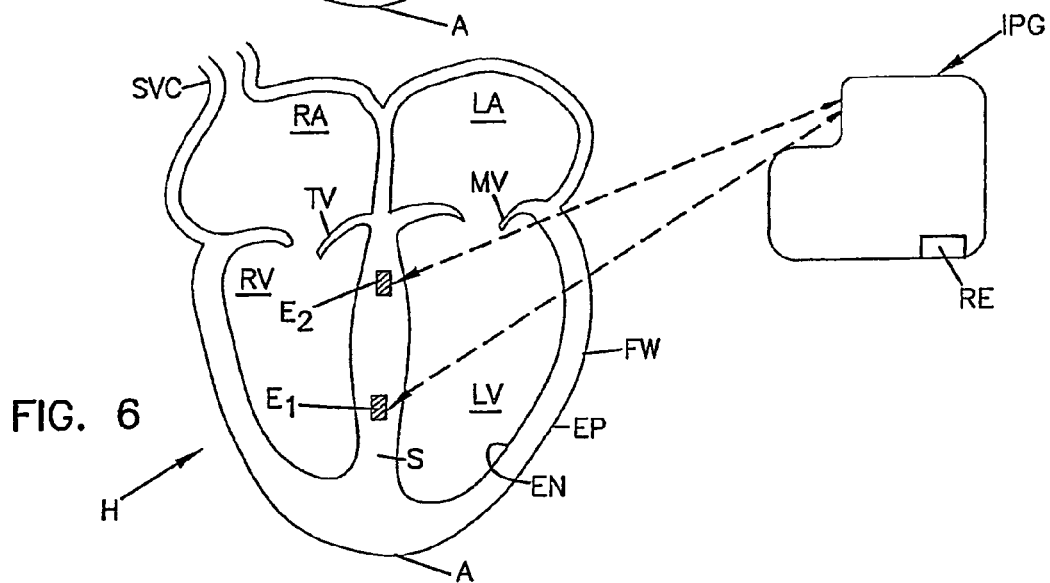
FIG. 6 is the view of FIG. 5 showing electrodes embedded within the septal wall.

FIG. 5 illustrates the electrodes $E_1$, $E_2$ individually placed on the septal wall S and not retained on a lead body. In such an embodiment, the electrodes $E_1$, $E_2$ may be energized in a pacing waveform by wireless transmission signals $T_1$, $T_2$ from the implantable pulse generator (IPG). Wireless transmission from a controller to an electrode is shown in U.S. Pat. No. 6,907,285 to Denker, et al., dated Jun. 14, 2004. Alternatively, the electrodes $E_1$, $E_2$ may be directly imbedded as microstimulators into the tissue of the septal wall S as illustrated in FIG. 6. Microstimulators for implantation into human tissue are shown in U.S. patent application Publ. No. 2004/0153127 published Aug. 5, 2004.

In a context similar to that discussed above, FIGS. 1-20 illustrate aspects of the present invention similar to that discussed above in connection with FIG. 1 where certain of these figures show common characteristics. FIGS. 1, 7B and 8 illustrate example leads and the associated electrical fields with both electrodes residing within the right ventricle with the distal electrode secured to the apex of the right ventricle, with FIG. 8 showing the ventricles RV, LV and a portion of the lead body $LB_1$. While such bipolar leads are acceptable for use with the present invention, a wider spacing between electrodes $E_1$, $E_2$ can increase the field but can sacrifice some sensing capability. This trade-off can be mitigated by use of a three-electrode lead in the right ventricle RV. Such a lead would have a tip electrode and two ring electrodes, one located near the tip in the RV apex and one in the high part of the atrium, near the tricuspid valve. The sensing is performed between the tip and closer electrode. This will provide good so-called "near field" sensing and avoid so-called "far field" sensing of the atrium or skeletal muscles activity. The pacing could be between the ring electrodes to the return electrode located distally to the heart (as will be described). One could also combine the tip and nearest ring as one electrode to the return electrode and the other ring electrode to the return electrode at the opposite polarity. In a particular embodiment, a ring with a width of 4 mm is separated by a distance of 4 mm from a tip with a width of 4 mm.

Another characteristic is the pulse generator IPG which is common to FIGS. 1-7b. The pulse generator IPG generates a first and a second pulsed waveform $W_1$, $W_2$ applied, respectively, to the first and second electrodes $E_1$, $E_2$. FIG. 18 shows such waveforms $W_1$, $W_2$ of depicting signals generated by this illustrated IPG. By way of example, and not intended to be limiting, the pulse duration (PD) is between about 0.1 to 2.0 milliseconds, the amplitude A may be 0.1 Volts to 10 or 20 Volts and the time delay TD between pulses is a targeting heart rate (e.g., 50 to 200 beats per minute).

The arrangements shown in FIGS. 1-18B show examples of electrode placements (e.g., electrode $E_1$) at various positions along or near the septal wall. In FIG. 7A, for example, the first electrode $E_1$ is attached to the mid- or upper-septum.

The reference electrode RE, used in some but not all such embodiments of the present invention, is on the housing of the IPG and positioned subcutaneously near the right or left shoulder. The re-direction of the field may also be useful in decreasing defibrillation thresholds for arrangement similar to that shown in FIG. 7B. In FIG. 7B large segmented (for flexibility) electrodes $E_2$, $E_3$ are shown in the superior vena cava SVC near the atrium RA and in the right ventricle to serve as shocking electrodes to defibrillate a patient.

Figure 8:
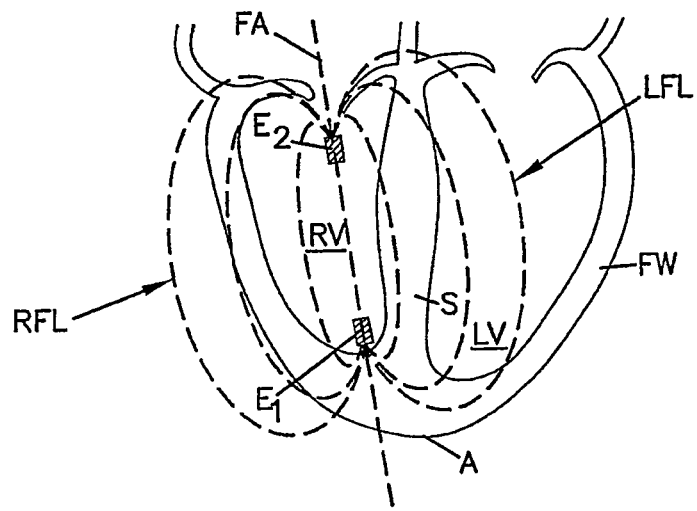
FIG. 8 is a view, taken in cross-section, of right and left ventricles of a heart showing the electrodes of FIG. 1 (without showing the lead body) energized to create electromagnetic fields.
Figure 9:
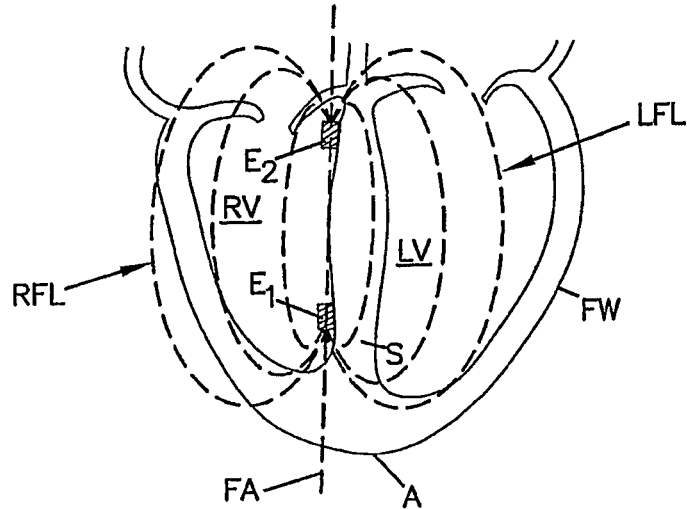
FIG. 9 is the view of FIG. 8 showing the field shifted toward the left ventricle in response to repositioning of leads.

Another characteristic relating to the above-discussed aspects for improved heart function concerns placement of the electrodes to effectively stimulate the septal wall. As an illustrated example of such placement, FIG. 9 shows field lines useful for such stimulation and resulting from movement of the electrodes $E_1$, $E_2$ from the interior of the right ventricle RV (FIGS. 1 and 8) to the septal wall S. Such movement shifts the field lines toward both the septal wall S and the free wall FW of the left ventricle LV.

Certain of the embodiments that use a reference electrode RE in combination with the electrodes $E_1$, $E_2$ in the right ventricle, provide effective pacing of the left and right ventricles LV. Although the physics and physiology of the mechanism of action are not fully understood, it may be that the reference electrode RE distorts the electromagnetic field otherwise created between the right ventricle electrodes $E_1$, $E_2$ to urge an intensity of the electromagnetic field deeper into the septal wall S of the left ventricle LV. This may be due to creation of a third high current density spot (or spots) away from the two electrodes in the wall and towards the reference electrode at the point where the current flows between the electrode $E_1$ and the reference electrode RE and between the electrode $E_2$ and the reference electrode RE while coinciding in space and time. This is illustrated, for example, in FIG. 10. Assuming such a phenomenon occurs, it may facilitate the activation of the surviving conduction fibers in the Left Bundle Branch and Right Bundle Branch of His and Purkinje fibers and create a more rapid and uniform activation of the left and right ventricles that follows a similar pattern to the normal activation present in patients without conduction defects.

The reference electrode may be physically attached to the housing of the implantable pulse generator IPG (and thereby having a neutral charge). Such an electrode RE is shown in FIGS. 1-7B. It will be appreciated that the reference electrode RE can be connected to the implantable pulse generator IPG by a conductor. The reference electrode could be another common electrode that exists in the conventional pacing or ICD system, such as an electrode in the atrium or a defibrillation coil electrode situated in the SVC, RA or RV.

Figure 10:
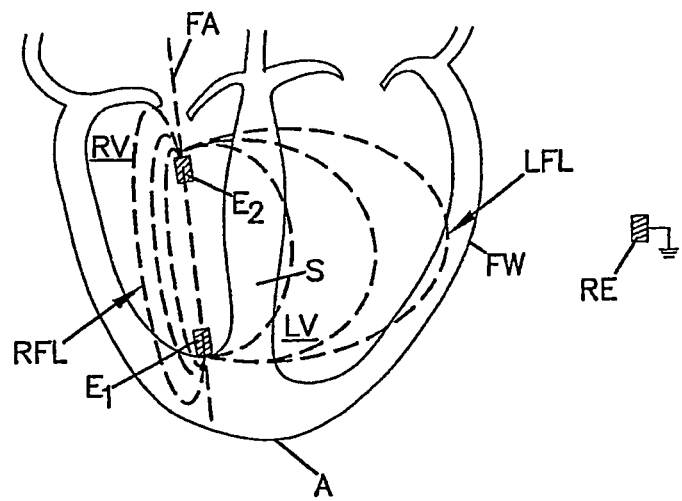
FIG. 10 is the view of FIG. 8 showing the field distorted toward a free wall of the left ventricle by influence of an external reference electrode.
Figure 11:
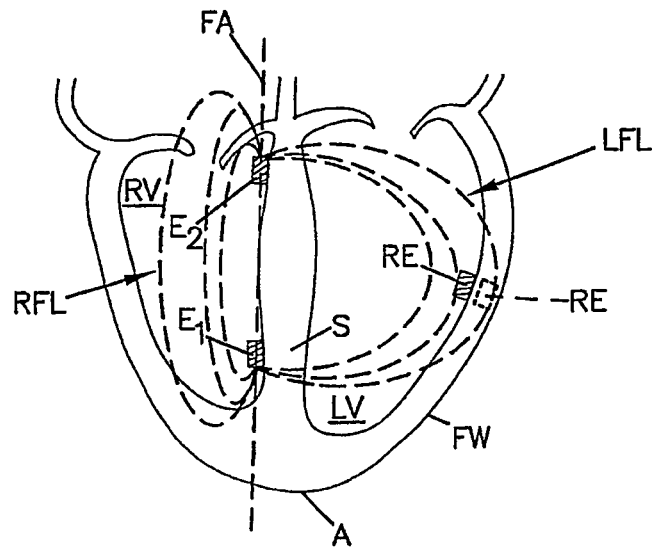
FIG. 11 is the view of FIG. 9 with a reference electrode placed within the left ventricle.
Figure 12:
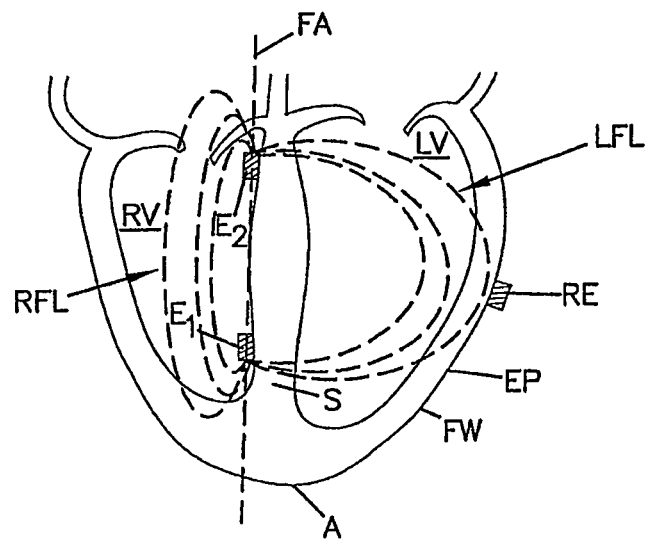
FIG. 12 is the view of FIG. 14 with an external electrode placed on the epicardial surface of the heart.

As shown in FIG. 10, the consequence of the reference electrode RE may have a deforming effect on the electromagnetic field generated between the first and second electrodes $E_1$, $E_2$. This is illustrated in FIG. 10 by distorting the left field lines LFL toward the septal wall S and free wall FW of the left ventricle LV. Also, the right field lined (RFL) are compressed toward the axis FA to alter the field from the symmetric presentation of FIGS. 8 and 9 to the asymmetric presentation of FIG. 10 with the field biased toward the septal wall S and the free wall FW of the left ventricle LV.

It has also been found that within energy levels associated with available implantable pulse generators (in some instances up to 10 or 20 volts), effective activation of the left and right ventricles LV can be achieved with appropriate placement of the pacing leads.

Chronic pacing with an anodal electrode is believed to create an exit (anodal) block, meaning that the capture thresholds of the cardiac tissue may go beyond the voltage range of the pulse generator. When this happens the beneficial effect of the stimulation is lost. Since capture is often lost, the patient's life may be placed at risk by such an event.

According to one embodiment of the present invention, the polarity of the charged pulses seen at electrodes $E_1$ and $E_2$ may be alternated. This can be particularly useful for avoidance of anodal blocking (gradual rising of the threshold voltage necessary to capture and re-synchronize the myocardium). Such polarity swapping may be implemented using a suitable periodicity. In a particular example, the polarity of the electrodes is switched after several hours of operation. In another example, this polarity is alternated beat by beat, so that the net charge delivered to the tissue over two beats would be zero. The frequency of alternation could be varied in a very wide range and still accomplish the goal of balancing the charge delivered, to allow for the net charge delivered on average to be near zero. This can be useful for avoiding the issue of anodal block and minimizing the risk of electrode dissolution and/or corrosion.

It has been discovered that in some instances proper placement of the lead along the septum produces unexpectedly small QRS widths. Moreover, proper placement may also result in lower voltage thresholds. The optimal lead location can be determined with the assistance of the surface ECG parameters (e.g., QRS width and/or activation vectors).

Figure 13:
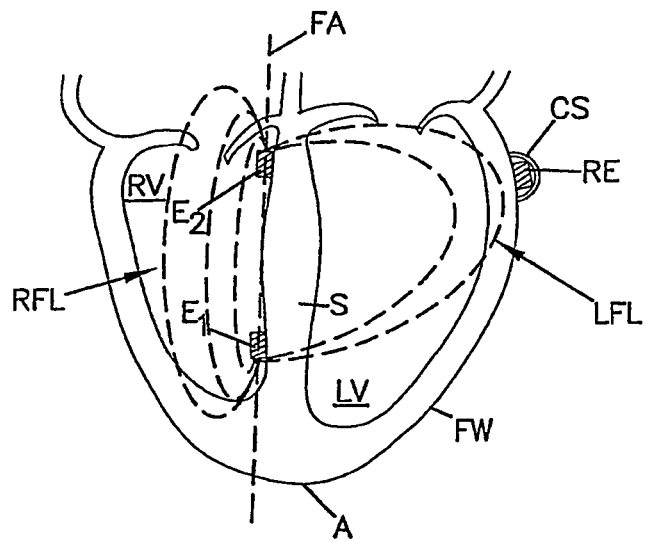
FIG. 13 is a view with an external electrode placed within a coronary sinus.

The positioning of the reference electrode RE may be directly on the housing of the implantable pulse generator IPG or may be separate from the internal pulse generator as previously mentioned. In one instance, the reference electrode RE can be placed in the left ventricle (FIG. 11) (or in the tissue of the free wall FW as shown in phantom lines in FIG. 11), on the epicardial surface EP (FIG. 12) or in the coronary sinus CS (FIG. 13).

Positioning the reference electrode RE relative to the heart can affect the distortion of the field in the area of the left ventricle free wall FW subject to pacing. Particularly for a subcutaneously placed reference electrode (which is preferred to minimize the invasive nature of the procedure), the electrical conduction path from the right ventricle RV to the reference electrode will vary considerably between patients.

Figure 15:
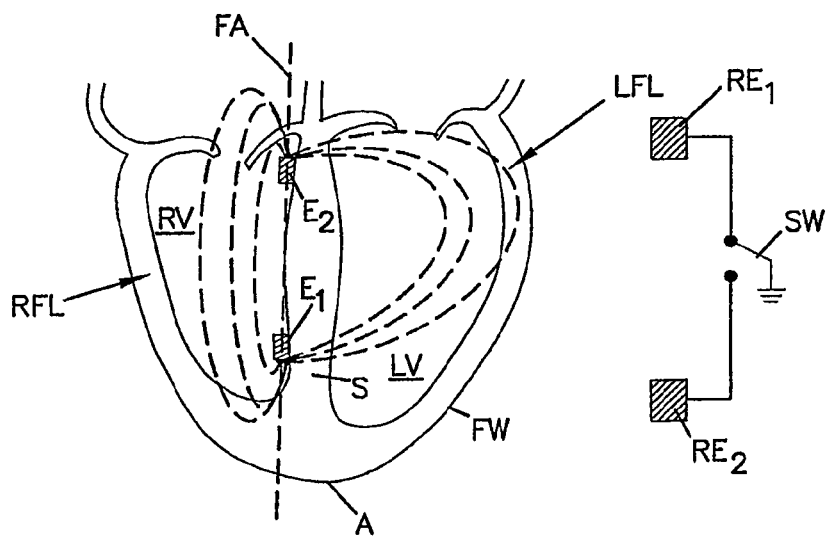
FIG. 15 shows a field distorted towards an upper end of the free wall in response to a reference electrode in a first position.
Figure 16:
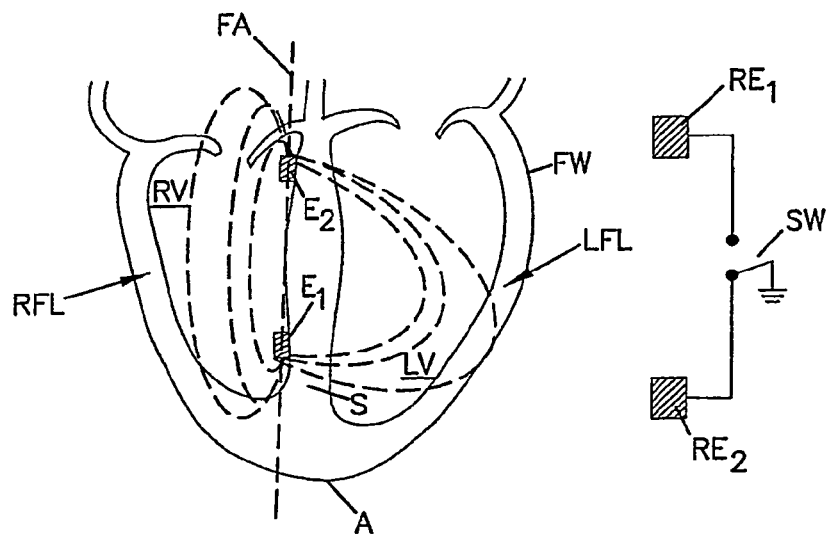
FIG. 16 is the view of FIG. 15 with a reference electrode switched to a second position.

Also, the direction of field distortion may alter the region of the left ventricle LV subject to pacing. For example, FIG. 15 illustrates the reference electrode $RE_1$ placed high relative to the heart, resulting in a distortion of the field toward the upper end of the left ventricle septum and free wall FW. FIG. 16 illustrates placement of a reference electrode $RE_2$ lower relative to the heart and to deflect the intensity of the field toward the lower end of the left ventricle septum and free wall FW.

While the reference electrode could be a single electrode, multiple electrodes could be provided for subcutaneous placement and each connected by a switch circuitry SW of the implantable pulse generator as illustrated in FIGS. 15 and 16. The patient's response can be noted with each of the several reference electrodes $RE_1$, $RE_2$ separately connected to the ground or housing of the implantable pulse generator. The patient can then be treated with the electrode showing the most effectiveness for the particular patient. Further, over time, a patient's response may change and the implantable pulse generator can be reprogrammed to select any one of the other reference electrodes as the switched electrode.

Figure 7:
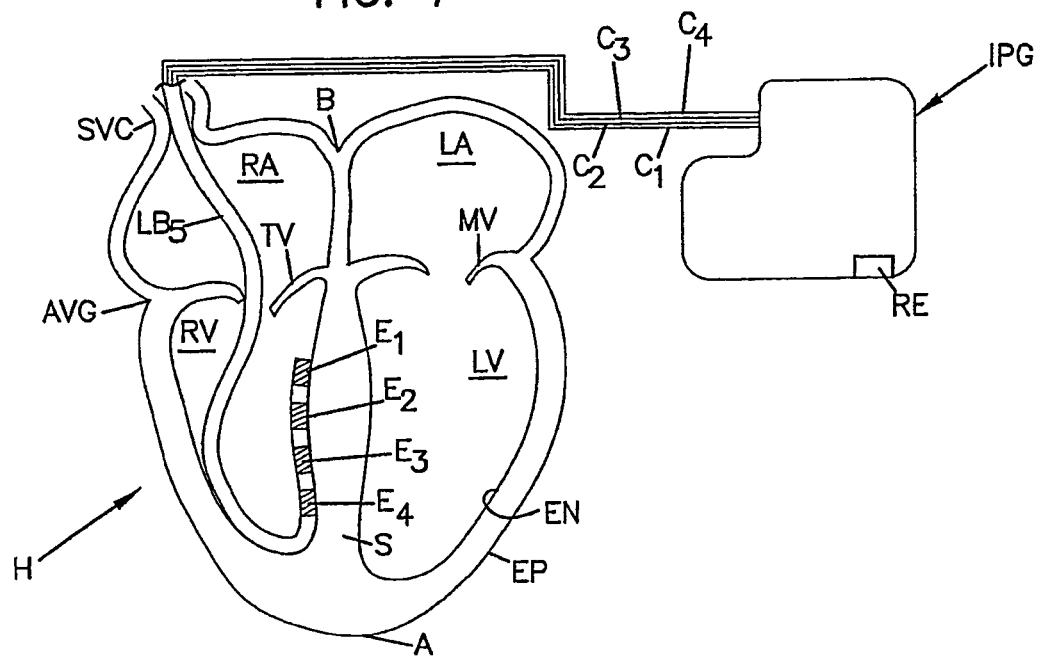
FIG. 7 is the view of FIG. 4 showing the lead of FIG. 4 with multiple electrodes urged against the septal wall.
Figure 7A:
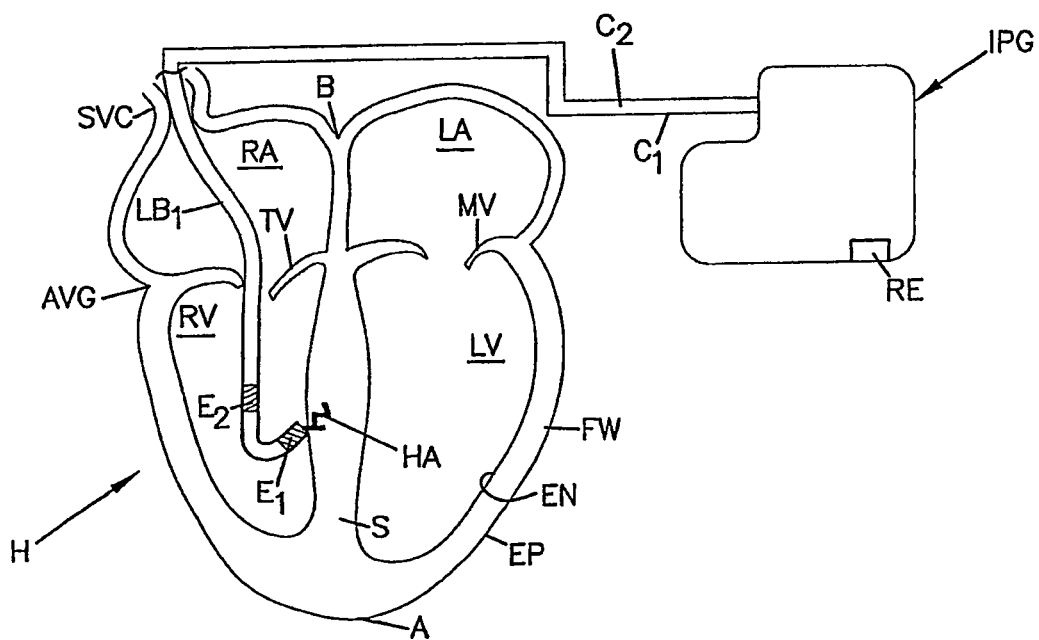
FIG. 7A is the view of FIG. 1 showing a conventional active fixation lead with a helix for attachment of the tip electrode to a septal wall.
Figure 7B:
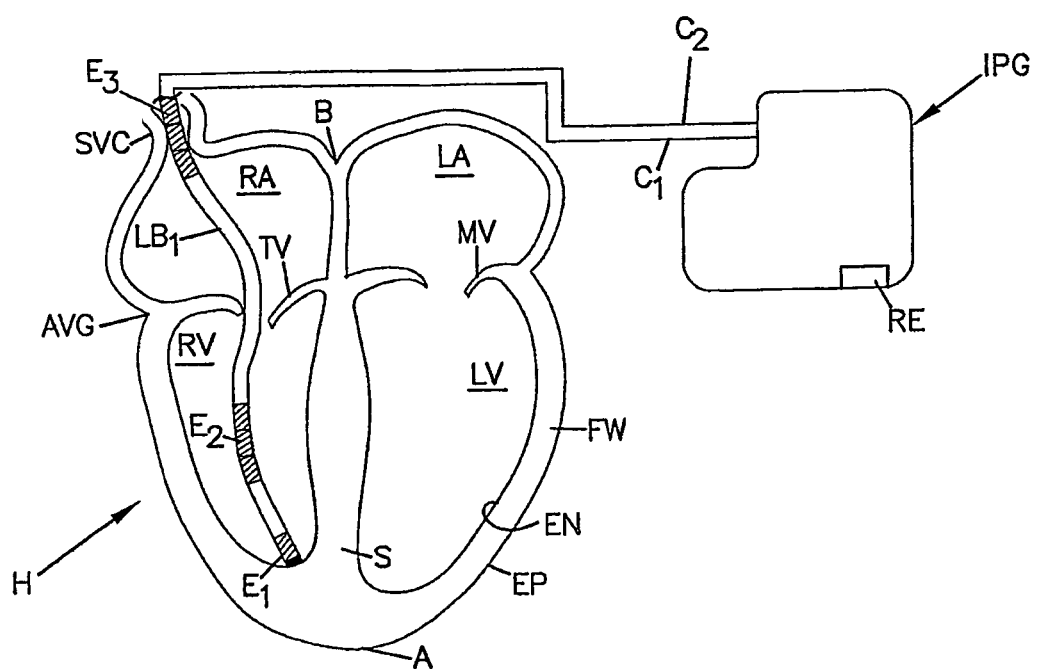
FIG. 7B is the view of FIG. 1 showing a shocking electrode.

In addition, the catheter $LB_5$ within the right ventricle can have multiple electrodes along its length (as shown in FIG. 7). Individual pairs of these electrodes $E_1$-$E_4$ can be switched on or off over time so that the appropriate pair of electrodes within the right ventricle is selected for optimized left ventricular pacing.

Figure 14:
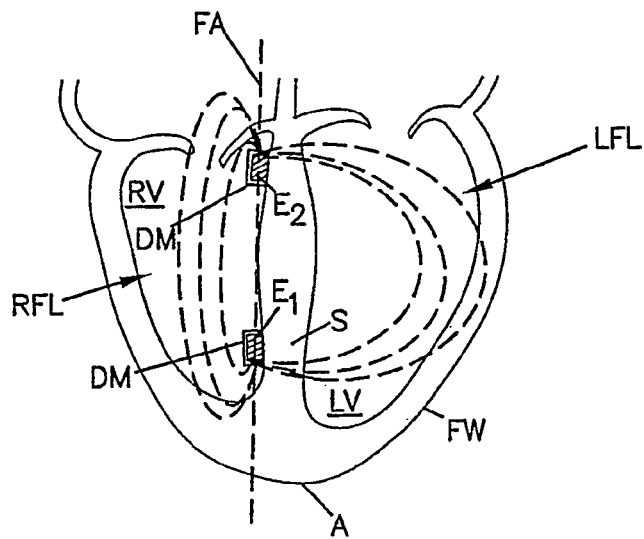
FIG. 14 is the view of FIG. 9 with fields distorted to be biased toward the left ventricle by the addition of dielectric material on a side of the electrodes of FIG. 9.

FIG. 14 illustrates how the field can also be distorted by dielectric material DM placed on a side of the electrodes $E_1$, $E_2$ opposite the septal wall S. The dielectric material DM result in a distortion of the electrical field biasing the left field lines LFL toward the septal wall S and the free wall FW. Of course, this configuration will work even better with a reference electrode which will enhance the benefit.

While positioning of the electrodes $E_1$, $E_2$ within the volume of the right ventricle RV is effective in combination with a reference electrode RE (FIG. 10), movement of the electrodes $E_1$, $E_2$ directly against the septal wall S may further enhance the therapeutic benefit of the present invention for reasons described above. Various techniques for movement of the electrodes $E_1$, $E_2$ against the septal wall S are disclosed.

In various embodiments, the reference electrode is grounded to the housing of the implantable pulse generator. FIG. 17 illustrates an alternative embodiment where the reference electrode includes two active electrodes $AE_1$, $AE_2$ external to the heart. The active electrodes $AE_1$, $AE_2$ are paced with pulsed waveforms which are polar opposites of the waveforms on electrodes $E_1$, $E_2$. This creates dual uni-polar field in addition to the left field lines LFL previously described.

In the Figure, the amplitude of the waveforms from FIG. 18 (or other waveforms as described) is shown in phantom lines as the battery voltage applied to the four poles on the left of FIG. 19 to charge the two pacing capacitors $C_1$ and $C_2$. Details of the charging circuitry as well as other controlling circuitry for pacing and sensing are omitted for ease of illustration. In one instance only capacitor $C_1$ is charged for the pacing output, whereas $C_2$ is not charged. Capacitor $C_3$ and $C_4$ are optionally implemented for coupling the pacing output to the patient. For ease of illustration and explanation, the output waveform from FIG. 18 with the same amplitude and simultaneous timing is assumed for the design schematic in FIG. 19. A switch $S_1$ permits selection between unipolar pacing and pacing Xstim or similar pacing (by contact with switch pole $A_1$) or bi-polar pacing (by contact with switch pole $A_2$). Selection between bi-polar pacing or Xstim pacing is made by applying a digital signal with the timing information as shown in FIG. 18 to either $T_1$ or $T_1$ and $T_2$, namely to either toggle the switch $S_5$ or $S_2$ and $S_5$ simultaneously. An AND gate is used to allow the close of the switch $S_2$ only for pacing according to Xstim. Switches $S_3$ and $S_4$ permit re-neutralization of the pacing charges at the patient-electrode interface.

As is customary with implantable pulse generators, the device may be programmable to achieve either conventional bipolar or unipolar stimulation or to achieve the Xstim stimulation through an external programmer or controlled automatically by the device. The selection can be based on user preference or be driven by physiological factors such as widths of the patient's QRS complex or the conduction interval between the stimulus to a far away region in the heart. In addition, switching between the Xstim pacing and other pacing can also be determined by the percentage of pacing with a preference for a higher percentage with the pacing of the present invention. Further, the switching from a first type of pacing to the Xstim pacing can be used when there exists an exit block or the pacing electrode is located in infarcted myocardium when first type pacing does not capture (effect the depolarization of) the myocardium at the high output level. The automatic determination can be effected through the deployment of any automatic capture detection technology including, but not limited to, electrical sensing of the heart. Additionally, wireless network-enabled switching function for therapy optimization can also be implemented with the present invention. In such cases, certain patient physiologic data are gathered by the implantable device and sent to a remote server/monitor through a wireless communication network.

In connection with other embodiments and related to the waveforms shown in FIG. 18, the stimulus voltage is consistent with discharge of an RC circuit as shown by FIG. 23A. This may be accomplished by connecting the electrode(s) to the anode (and/or cathode) of a charged capacitor.

According to another embodiment of the present invention, the stimulus voltage is consistent with the discharge of two sets of two capacitors in succession, as shown by FIG. 23B.

This may be accomplished by connecting the electrode(s) to the anode (and/or cathode) of a first charged capacitor and then to a second charged capacitor. This embodiment may be useful for reducing the voltage swing of the pulse, thereby altering the delivery of energy during the active stimulation period and potentially minimizing the voltage required to achieve the desired effect. In a particular instance, a first set of capacitors could be connected to electrode $E_1$ and a second set could be connected to electrode $E_2$. The voltages provided to the electrodes could be of opposite polarity as in the standard Xstim waveform or could be alternated as described above to make the net charge delivered to the electrodes equal to zero.

Other embodiments may allow for the use of two sets of three or more capacitors as shown by FIG. 23C. Moreover, various voltage-regulation techniques may be used to provide a constant voltage, or square waveform, as shown by FIG. 23D. This may be useful to provide a more constant delivery of voltage during the active stimulation period. In some instances, such waveforms may allow the reduction of voltage thresholds required to achieve the desired effect. According to one embodiment of the invention, one of these groups of three or more capacitors could be connected to electrode $E_1$ and the other group of three capacitors could be connected to electrode $E_2$. The two groups may be charged to opposite polarities, as in the standard Xstim waveform. Alternatively, the groups may alternate between electrodes $E_1$ and $E_2$, as described above, resulting in the net charge delivered to the stimulus point by the electrodes equal to zero.

Furthermore, in a less expensive device, using a single capacitor element (or multiple capacitors arranged in parallel), a single set of two capacitors independently addressable or set of three or more capacitors each independently addressable, the same effect could be achieved by using an anodal pulse delivered through the capacitive discharge of one, two or three or more capacitors to one of the electrodes with a larger amplitude voltage. This anodal pulse will be alternatively connected to one of the stimulating electrodes in one beat and to the next electrode on the next beat. In still another device the alternating frequency could be lower. For example, the anodal capacitive discharge could be alternatively connected to electrode $E_1$ and then to $E_2$ every 2 to 10,000 beats. If the alternating charges are equally distributed, the net charge delivered may be kept very close to zero. During the implantation of such a device the physician may place an intraventricular pacing lead in a preferred location (locus) that maintains the effect (using one of the previously-described methods, making each electrode alternatively the anode) when either of the electrodes is the anodal electrode.

The pulse width of the various embodiments may be varied according to the desired treatment and/or in accordance with the response of the particular patient. Example pulse widths may range from 0.05 ms to 5.0 ms.

According to certain example embodiments of the present invention, resynchronization is achieved by presenting a pulsing signal (waveform) to a sweet spot (e.g., locus in the septal part of the RV endocardium) and, every so often, modulating the signal such as by changing its polarity. In such embodiments where both an anode and cathode are used to present the pulsing signal, one manner of modulating the signal is by reversing the polarities of the signal relative to the anode and cathode. Where the pulsing signal is presented by an electrode and a reference voltage (e.g., a node at the can and/or at the body under treatment), the signal can be modulated in a similar manner by adding and/or skipping pulses.

As discussed infra, the power consumption of the pacing device can be an important consideration. While not bounded by theory, it is believed that different pacing profiles can be particularly advantageous to controlling pacing power. For example, during times that the pulses applied to each electrode overlap, the effective voltage seen between the electrodes is believed to be equal to that sum of their amplitudes.

Figure 22:
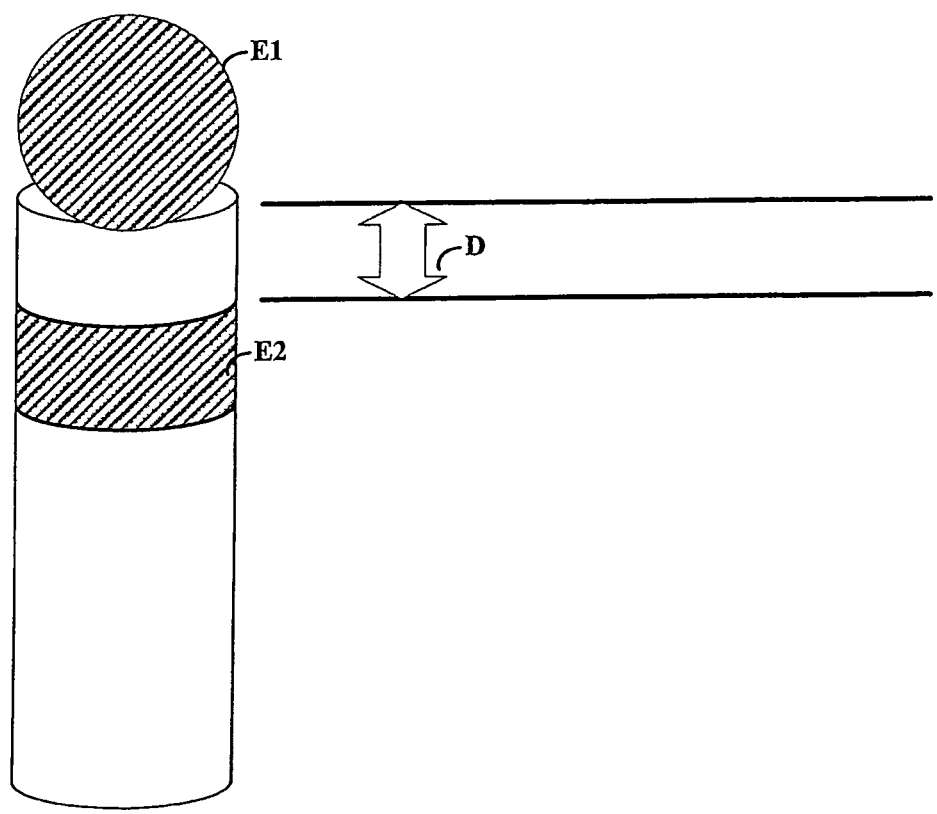
FIG. 22 is a view showing the spacing of two electrodes.

In another embodiment, the pulses shown by the figures are applied to the ring and tip electrodes, such as those illustrated in FIG. 22. The polarity of the voltages, as relative to each other and/or a reference voltage, may be alternated periodically (e.g., beat by beat or every N pulses). As discussed above, such alternating may be particularly useful for mitigating anodal blocking. Moreover, alternating of pulses may also mitigate corrosion of the electrodes.

Referring back to FIG. 18, such pulses are shown as square waveforms but, in practice, can be any of various geometries. With reference to FIG. 18 and the earlier figures, the first electrode $E_1$ has positively charged pulses only. The second electrode $E_2$ has negatively charged pulses timed to coincide with the positively charged pulses of the positive electrode $E_1$. While direct current (DC) pulses are preferred, the electrodes $E_1$, $E_2$ could be energized with alternating current pulses with the signals to the electrodes $E_1$, $E_2$ out of phase such that the positive pulses on the first electrode $E_1$ coincide with negative pulses on the second electrode $E_2$ and negative pulses on the first electrode $E_1$ coincide with positive pulses on the second electrode $E_2$.

With the electrodes $E_1$, $E_2$ charged with opposite pulses, it is Applicants' current understanding that an electrical field is created between the electrodes $E_1$, $E_2$ with a field axis FA (FIG. 8) extending in a line between the electrodes $E_1$, $E_2$. In the absence of distorting influences (such as external magnetic fields, external electrodes or non-homogenous conductivity due to variances in conductivity of blood, tissue bone, etc.), the field is symmetrical about the field axis FA and is represented by field lines illustrated in the drawings as left field lines LFL to the left of the axis FA (with left being from the patient's perspective) and right field lines RFL. The field lines represent the intensity of the electrical field. The intensity diminishes rapidly as a function of the distance from the field axis FA.

As discussed above in connection with various embodiments including the electrodes $E_1$, $E_2$, in order for the fields generated by the electrodes $E_1$, $E_2$ to have a significant influence on both the septal walls and the free wall FW of the left ventricle LV, a voltage potential across the electrodes is set at a substantially high level. However, such high voltages are not practical in a pacing electrode and are more normally associated with defibrillating treatments. Also, such voltages may cause phrenic nerve and/or diaphragmatic stimulation and may also cause a significant drain on a battery that would require impractical frequency of battery replacement.

Figure 18A:
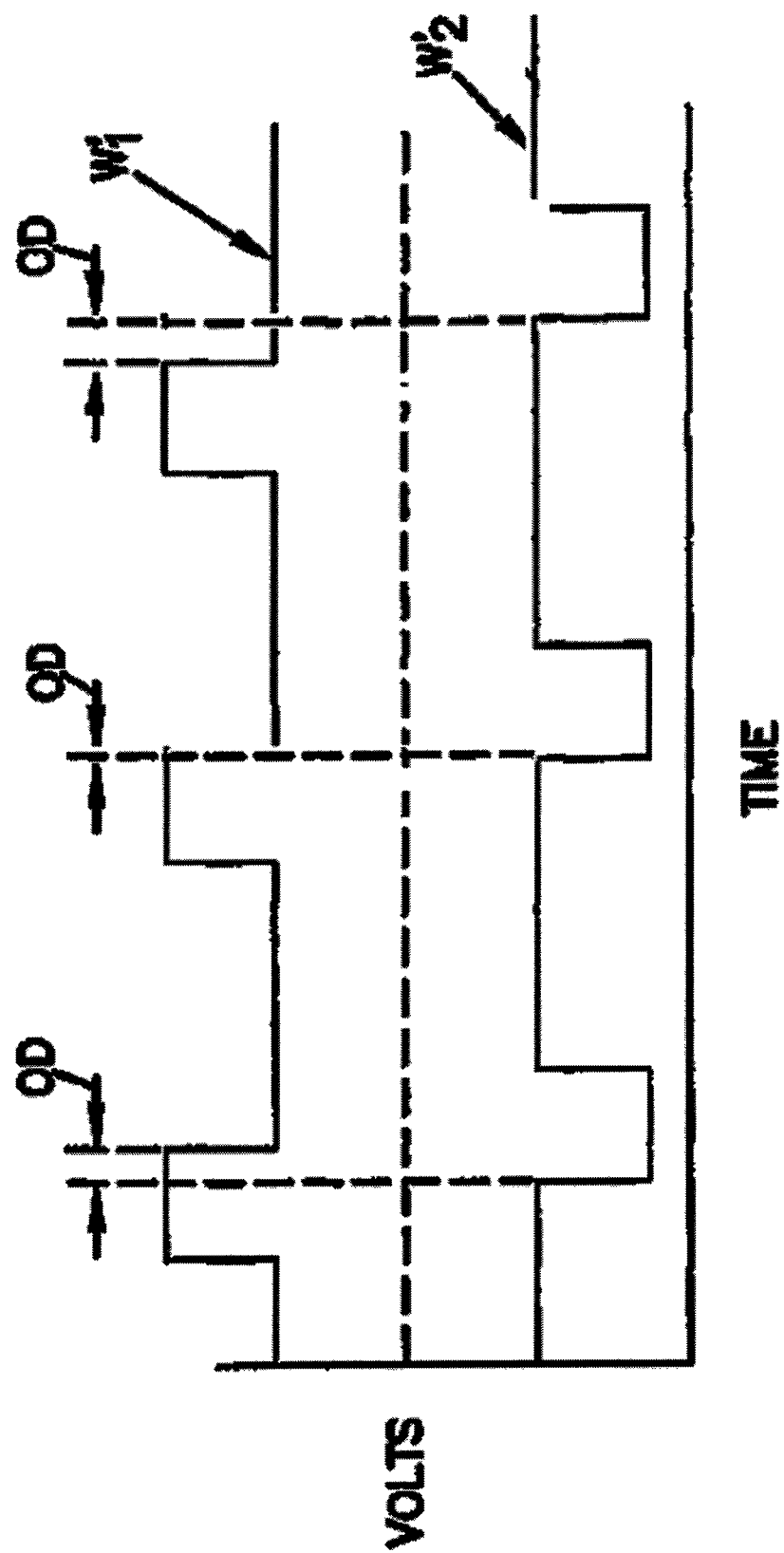
FIG. 18A is a view similar to that of FIG. 18 showing alternative waveforms.
Figure 18B:
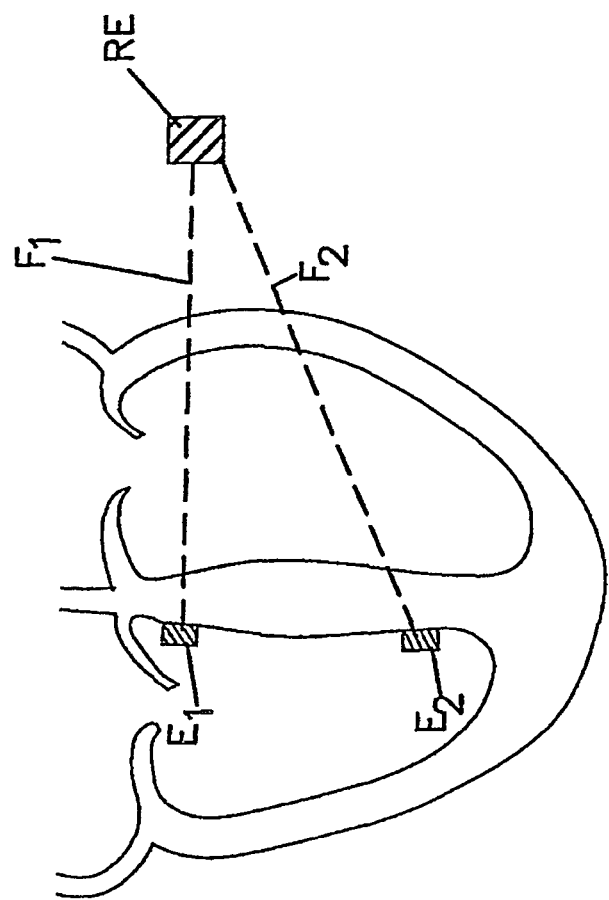
FIG. 18B is a view similar to that of FIG. 18 and showing two electrodes creating two separate fields to a reference electrode.

FIG. 18 illustrates an example waveform with electrodes $E_1$, $E_2$ being simultaneously pulsed with opposite polarity. FIG. 18A illustrates waveforms $W_1'$, $W_2'$ of similar structure to the waveforms of FIG. 18 but out of phase. The first set of pulse illustrated in waveforms $W_1'$, $W_2'$ present a partial overlap duration OD (OD is a positive value). The second set of pulses are further out of phase such that the beginning of one pulse coincides with the end of another pulse (OD=0). The third set of pulses includes pulses that are out of phase such that the leading edge of one pulse occurs after the end of the first pulse of the set (OD has a negative value). With FIG. 18A at least a portion of time includes a monopolar pacing from individual ones of the electrodes $E_1$, $E_2$ to the reference electrode RE. This pacing creates out of phase monopolar fields $F_1$, $F_2$ as illustrated in FIG. 18B. Values of OD can range from the entire pulse length (e.g., around two milliseconds) to a negative value of several milliseconds (e.g., around negative two milliseconds). Although not explicitly shown in FIG. 18A, either of the negative or positive pulses can lead the other pulse, respectively. Also, while the amplitudes of the two waveforms are shown to be equal, they need not be equal in practice nor do they necessary need be implemented as strict square waves. For non-square wave pulses or pulses with relatively slow fall or rise times, the OD can be calculated accordingly. In one example, the OD may be calculated from beginning or end of the rise/fall of each pulse, respectively. In another example, the OD may be calculated from when each pulse reaches a certain voltage level, respectively, or once the pulse has maintained a certain voltage level for a period of time.

FIG. 19 illustrates a representative circuit in schematic format for a portion of a cardiac stimulation pulse generator that is capable of providing pacing output for either the conventional waveforms or Xstim waveforms as herein. The circuit of FIG. 19 could be for an implantable pacemaker or any external stimulation system for diagnostic or therapeutic use.

The stimulation device has three output terminals that are connected to three electrodes $E_1$, $E_2$, RE in the body. Electrodes $E_1$, $E_2$ are positioned in the right ventricle RV with it being preferred that at least one of these electrodes be in direct contact with the septum S.

The reference electrode RE is an indifferent electrode which can be connected electronically to the housing of the implantable pulse generator IPG. The reference electrode RE may be an electrode directly on the implantable pulse generator or any other electrode for placement inside or outside of the heart as described above.

The present invention can also be extended to the defibrillation therapy where high-energy pulses with various waveforms are delivered through electrode systems to treat tachycardia and fibrillation (both atrium and ventricle). The present invention is believed to be able to achieve a lower defibrillation threshold due to better distribution of the electrical field, causing higher voltage gradient at least in certain parts of the heart compared to that by the conventional defibrillation configuration as seen in FIG. 7B. Additionally, the present invention can be used to perform anti-tachy pacing where faster than conventional pacing pulse sequences are used to stop certain tachyarrhythmia. Aspects consistent with present invention are believed to provide wider coverage of the electrical field and the capability of capturing special conduction systems in the heart (both atrium and ventricle).

In a particular embodiment, the electrodes $E_1$ and $E_2$ are positioned proximate to one another as shown in FIG. 22. This can be particularly useful for localizing the region in which the electrical stimulus (using one of the configurations described before) can achieve the desired synchronization or resynchronization effect. For example, the electrodes may have a width of around 4 mm and may be positioned within a distance D of about 5 mm from one another. In another example, the electrodes may be positioned within a distance D of about 2 mm or less.

The selective placement may be modified for a particular dysfunction and/or for a particular patient. For instance, the electrodes may be positioned near the His bundle. Locating the electrodes near the His bundle may advantageously allow for capture of both the right and left ventricle. Moreover, resynchronization of the left (or right) ventricle may be possible even for cases of LBBB (or RBBB).

FIG. 21 shows a system for selectively placing the electrodes. In a specific embodiment the lead discussed in connection with FIG. 22 may be used. The lead position is adjusted through various methods via conceptual block 104.

If desired, the lead position may be monitored and location information may be provided to myocardium capture analysis block 102. Myocardium capture monitor block 106 monitors the effectiveness of the current lead position in capturing and re-synchronizing a contraction of the myocardium of the left and right ventricles. The monitor information is provided to myocardium capture analysis block 102, which processes the received information for the purposes of positioning the electrodes.

In a specific example, monitor block 106 uses ECG measurements to monitor myocardium capture and re-synchronization. Analysis block 102 may analyze various factors of the far field measurements including, but not limited to, the QRS width (e.g. determined from a vectocardiogram). The ECG measurements may be supplied from a number of different inputs including, but not limited to, defibrillation coils, the can of the implantable device, an electrode of a pacing or sensing lead or an external ECG (or similar) device.

In another example, monitor block 106 may measure the amount of blood flow resulting from a contraction of the myocardium.

The system of FIG. 21 may also be used to adjust other re-synchronization parameters. For instance, the voltage levels and waveforms may be adjusted according to feedback from monitor block 106 and analysis from analysis block 102. In particular it has been discovered that careful placement may allow for low voltages to be applied to the electrodes. In one embodiment, the pacing impedance of the lead and electrodes is low to allow for effective delivery of the pacing voltage. This may be useful for reducing the power consumption of the device and for reducing the voltages necessary to deliver the stimulus. By proceeding in this manner, (e.g., using low impedance and maintaining low voltage), phrenic nerve stimulation or diaphragmatic stimulation, both highly undesirable side effects of high pacing, may be avoided.

In a particular embodiment, the lead has a screw with a short screw relative to screws used to reach the left ventricle or the His bundle. This allows for fixation of the lead until encapsulation and helps reduce mechanical problems associated with such attachments. In one instance, the screw may be made from a non-conductive material, thereby electrically isolating the attachment point. In another instance, the screw may be otherwise electrically isolated from the electrodes for delivering the pacing voltage even where the screw is made from a conductive material.

In another embodiment, a hook is used as the attachment mechanism. Yet another embodiment includes the use of a T-bar as the attachment mechanism.

Due to these and other aspects, one of skill in the art would recognize that the use of the reference electrode, as discussed herein, may be optionally implemented to provide effective re-synchronization. In one such instance, the reference electrode is used to provide a reference voltage derived from the in vivo voltage at a particular location. This reference may be used to reference the voltage provided at the stimulus location to the particular location. For example, the reference location may be taken at the can location or from a reference electrode located near the stimulus location. In another instance, no reference electrode is used.

It has been discovered that selective placement of the electrodes may provide a number of unexpected advantages. More specifically, selective placement of the electrodes along the septum appears to provide re-synchronization of the left and right ventricles even for cases of LBBB where the lesion of the bundle would not be considered proximal. Furthermore, in many instances a large improvement has been seen in the level of synchrony in patients with LBBB and also in patients with moderate or advance HF and conductions defects including LBBB, RBBB and IVCD. For instance, locating the electrodes near an optimal location on the septum has been shown to produce smaller than expected QRS widths. Moreover, the threshold voltages necessary to capture the myocardium of the left and right ventricles or to produce the smaller than expected QRS widths (or indications of improved heart function) may be relatively small.

Figure 24:
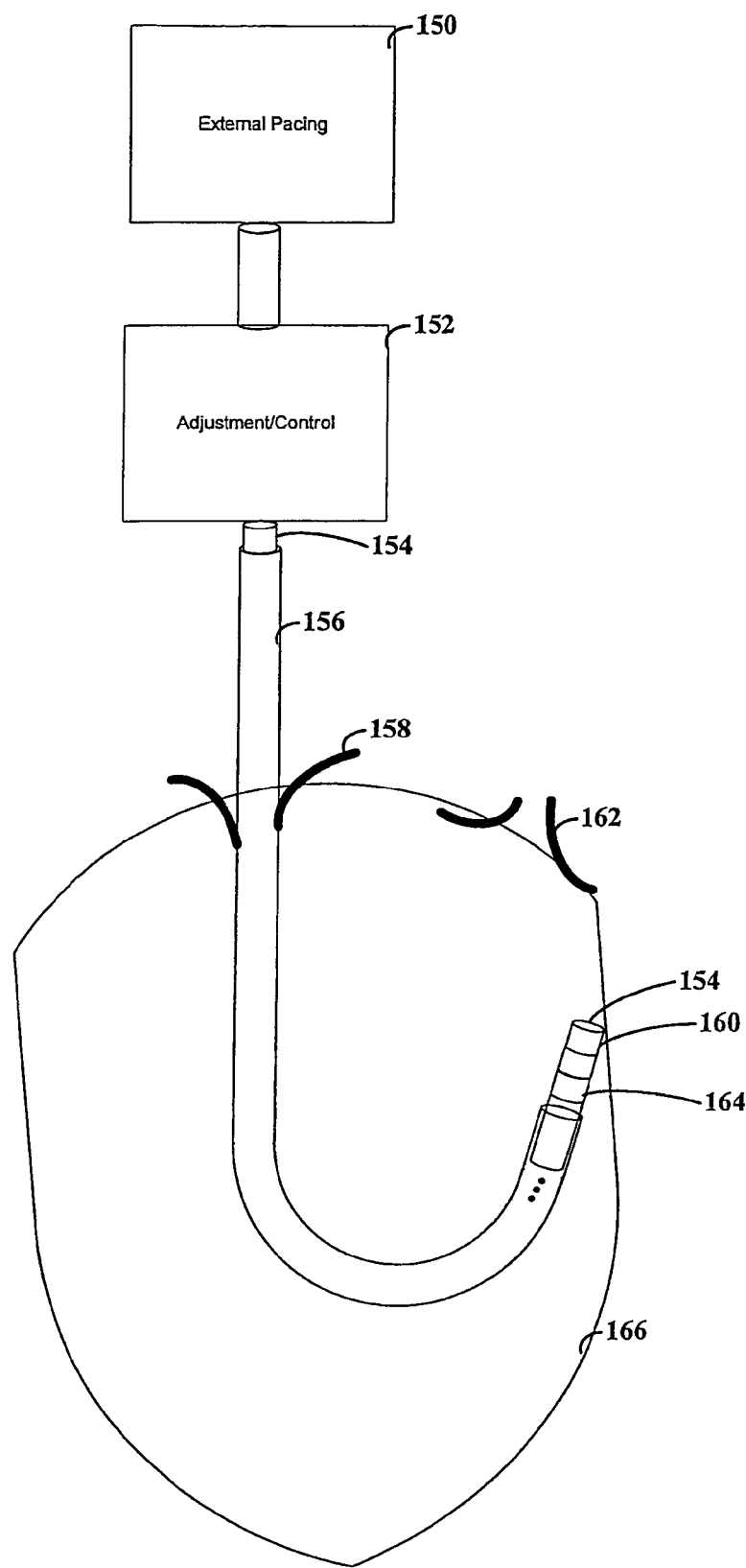
FIG. 24 is diagram of a directable/adjustable catheter-type device useful for delivering certain pulsed waveforms.

FIG. 24 shows an example of a sheath for use within the right ventricle 166 of the heart. The outer sheath 156 is designed to be inserted through the mitral valve 158 and into ventricle 166. Outer sheath 156 may include a J-type bend as shown in the figure. In various applications, this advantageously facilitates the placement of electrodes 160, 164 near the septum and/or the tricuspid valve 162. In one embodiment, one or more of the outer and an inner sheath 154 may arranged to allow directional control of the sheath position (e.g., by allowing for the adjustment of their curvature).

In a specific embodiment, inner sheath 154 is located within outer sheath 156. Inner sheath 154 may be adjusted, relative to outer sheath 156, using adjustment mechanism 152. In one instance, the adjustment mechanism 152 includes an adjustable track wheel or another similar mechanism. Additionally, inner sheath 154 may contain a pacing lead and/or a guide wire for additional stability. The adjustment of inner sheath 154 may be accomplished through a number of different techniques. According to one such technique, the inner sheath is allowed freedom to advance through the outer sheath and to move along the septum. In another example technique, the inner sheath may be arranged to direct the lead placement (e.g., by allowing for the adjustment of its curvature). The inner sheath and/or the outer sheath may have an electrode at their tip to use for pace mapping the locus for Xstim (following procedures discussed herein). Thus, facilitating the insertion of the chronic pacing lead. The inner and out sheaths may be peelable so that the pacemaker lead is kept in place while the sheaths are removed.

External pacing device 150 provides electrical pulses to the electrodes 160, 164. The positioning of the electrodes 160, 164 may be adjusted and the effectiveness of each position may be monitored. Various examples of suitable monitoring techniques are discussed in more detail herein. In some variations, the adjustment mechanism includes a number of fixed settings that can be reproduced. This allows for easily retrievable positioning of the electrodes 160, 164 as correlated to the effectiveness of each position. For example, the inner sheath may be advanced along positional settings 1 through 10 and corresponding monitoring input may be used to determine which setting is preferred. The inner sheath may then be set to the preferred setting after a comparison between the results corresponding to each of the tested settings.

In one embodiment, each electrode may be selectively and independently used to stimulate a synchronous contraction. The voltages for each electrode are varied to determine voltage threshold necessary to produce ventricular capture or to produce improved heart function. Low average stimulation voltage and current may be obtained by selecting the electrode that has the lowest effect threshold (effect refers to resynchronization effect or to maintaining synchrony of the contraction during pacing effect).

In one embodiment, the outer and inner sheaths may then be removed. A number of techniques may be used for such a removal. Using one such technique a guide wire is advanced through the sheaths and is used to hold the pacing lead in place while the sheaths are removed. In another technique, the sheaths are constructed with a slit that allows for their removal from the pacing lead without significant force being applied to the pacing lead.

In one embodiment, the inner sheath may function as a temporary pacing device connected to an external pacing source. The external pacing source may advantageously be equipped with additional processing and display capabilities (relative to an implantable device, which is often limited due to battery life and physical size constraints) to assist in locating the proper placement location. The inner and outer sheaths may be removed once the pacing lead is attached. The pacing lead may also be connected to an implantable device.

In a specific instance, the external device operates to provide a variety of different voltage waveforms and/or stimulus timings to the stimulus location. Feedback from an ECG or other device may be used to identify the preferred waveforms. The implantable device may then be uploaded with corresponding information for use in providing stimulus. In one such instance, the pacemaker may include a wireless port that allows an external interface to monitor and/or adjust the pacing functions. In this manner, the external device need not provide the stimulus through the external sheath. Instead, the implantable device may deliver the same set of stimulus using the wireless interface.

In another instance, the outer sheath may be designed with a removable interface that is compatible with both the external pacing device and the implantable pacing device. This allows for the use of the external pacing device during placement of the electrode(s) and use of the same outer sheath with the implantable pacing. This may be particularly useful for reducing the size of the sheath, the cost of the device or for simplifying the procedure by avoiding the step of removing the outer sheath.

In connection with the various drawing figures and relevant discussions, the following disclosures are incorporated herein by reference in their entirety: U.S. Pat. No. 6,230,061 B1 to Hartung issued May 8, 2001, for details of a cardiac pacemaker with localization of the stimulating pulses and U.S. Pat. No. 6,907,285 to Denker, et al., dated Jun. 14, 2004, for details of a wireless defibrillation system; U.S. patent application Publ. No. 2004/0153127 published Aug. 5, 2004 for details related to the use of a microstimulator in the proximity of at least one anatomical structure to produce muscular contractions; U.S. Pat. No. 6,643,546 B2 to Mathis et al. dated Nov. 4, 2003, for details related to the treatment of congestive heart failure.

Figure 24A:
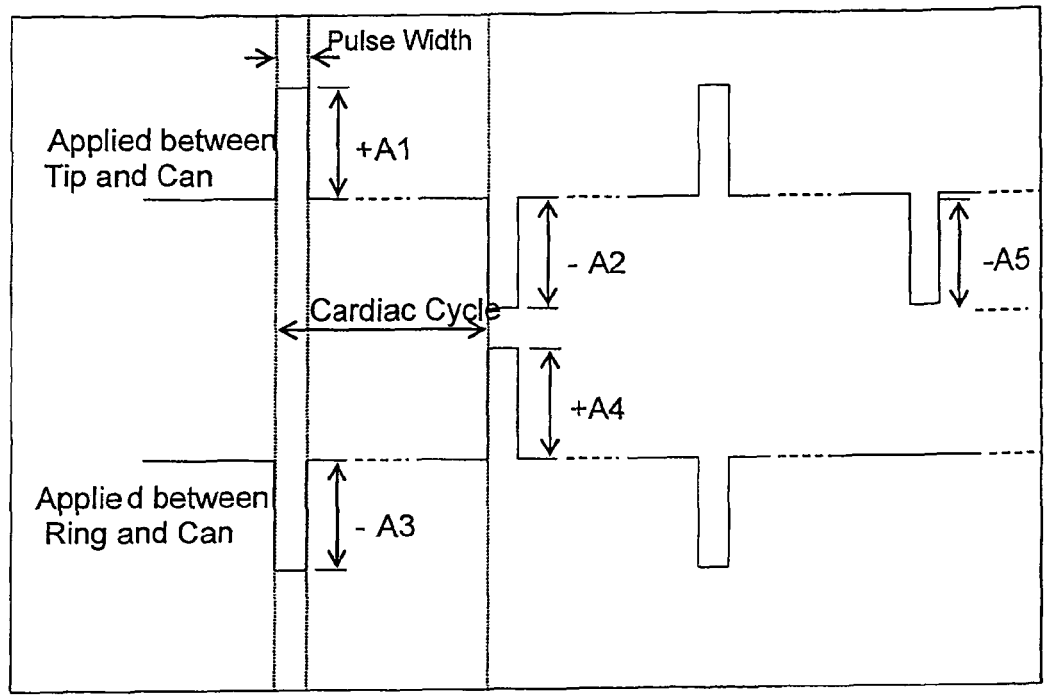
FIGS. 24A, 24B, 24C and 24D depict a graphical representation of pulsed waveforms to be applied by the electrodes of the various embodiments.
Figure 24B:
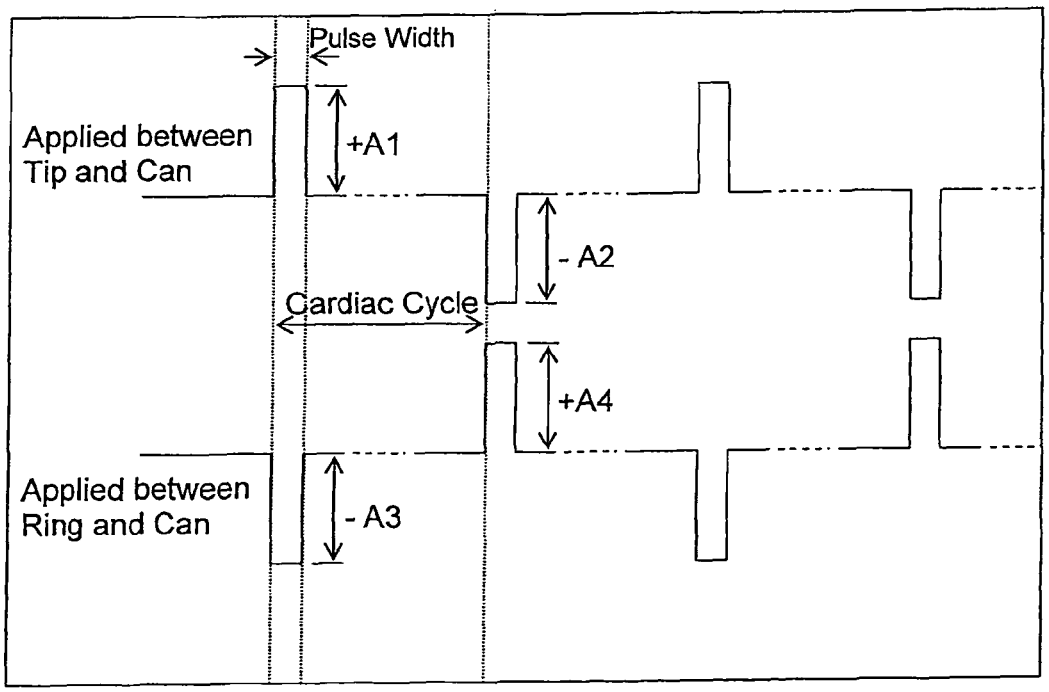
Figure 24C:
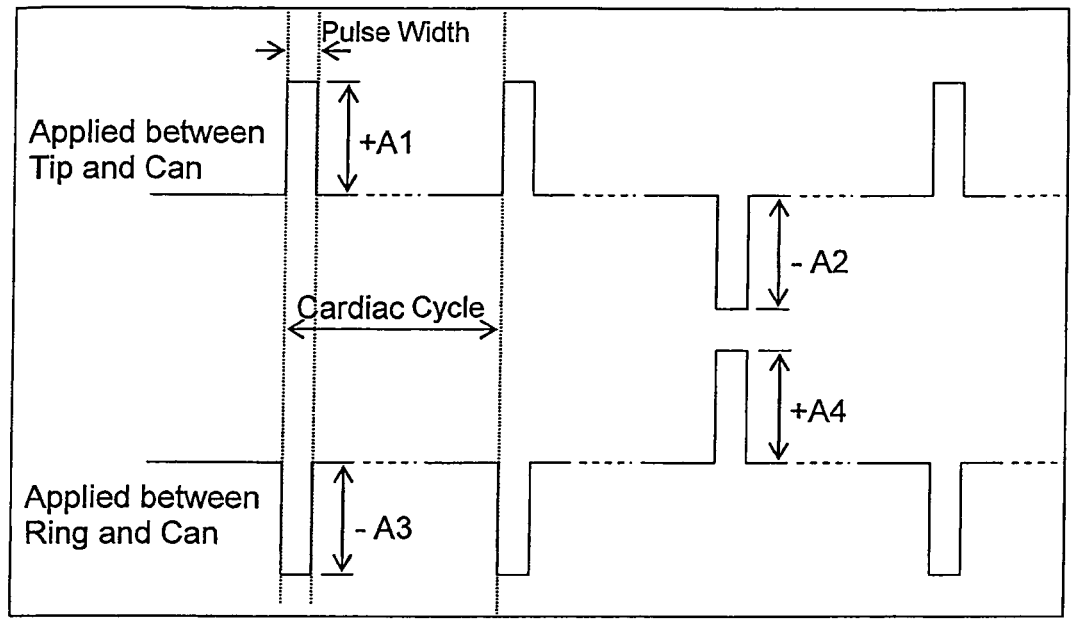
Figure 24D:
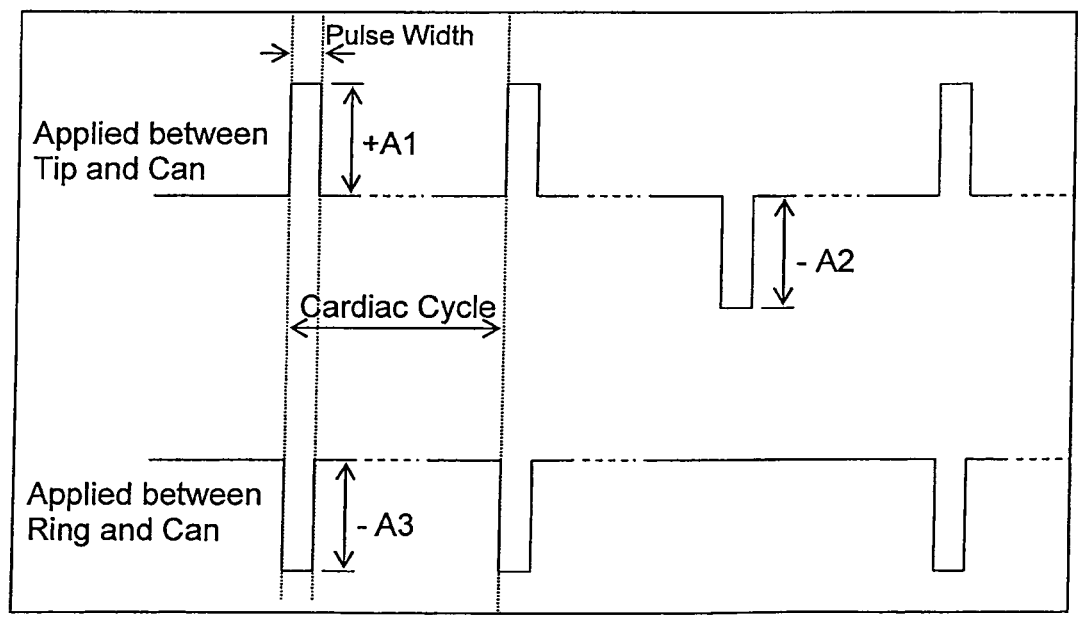

Consistent with these and other example embodiments of the present invention, FIGS. 24A-D depict additional waveform patterns that may be provided by an electronic circuit. For example, FIG. 24A shows pulses A1, A2 and A5, which represent voltages applied to a first electrode (e.g., the voltage differential between the tip and the can), while pulses A3 and A4 represent voltages applied to a second electrode (e.g., the voltage differential between the ring and the can). Control logic in the pacemaker device allows for the individual adjustment of the voltage amplitude of the various pulses and for the adjustment of the pulse width or duration. The specific parameters may be implemented by iteratively changing the waveforms and monitoring the effectiveness of the pulse. For instance, the selection of the ideal waveform may be made by selecting the waveform that produces the smallest QRS width as measured by an ECG. While FIG. 24A depicts the pulse polarity as alternating each beat, it should be apparent from the discussion herein and from FIGS. 24B-C that this is merely one example of a possible pulse modulation scheme.

In a particular embodiment, one or more pulses may be withheld as shown by the lack of a pulse on the ring electrode that corresponds to pulse A5 on the tip. In this sense the ring electrode pulse has effectively been withheld or skipped. In certain embodiments, either or both of the pulses may be withheld. Such withholding of pulses may be periodically implemented (e.g., once per every N pulses, or once every 20 minutes per 24 hours to allow heart to be conditioned by its own intrinsic contraction if the intrinsic heart rate is above a certain acceptable rate, such as 50 beats/minute). In another instance, the withholding may be responsive to feedback from a sensing electrode or ECG input.

It has been reported in literature that a small percentage of conventional RV apical pacing, which has been shown to be detrimental to the cardiac function, provided benefits to the overall patient wellbeing due to the healthy sympathetic and parasympathetic exercises introduced by the sporadic cardiac stress associated with RV pacing. As the pacing disclosed herein (including Xstim pacing) has been shown to resynchronize the LV ventricle, reducing the stress level of the diseased hearts, the withholding of (Xstim) pacing signals periodically or sporadically is useful to improve the overall patient wellbeing.

As discussed herein in connection with various aspects of the methodology useful for implementing the present invention, an example procedure for determining placement of a lead for pacing involves at least one repetition of pacing, sensing and repositioning using at least one lead adapted to deliver a pacing profile. While, not all of the data shown in the various figures was implemented as part of the experimental tests discussed herein, it is believed that the data shown is accurate. In a specific implementation of this procedure, pacing of the heart is accomplished using a lead placed in the right ventricle and near the His bundle. For example, the lead can include two electrodes (and in some instances one) to deliver oppositely charged pulses. Heart functionality associated with the pacing then is monitored. The monitoring can include one or more of the following examples, ECG readings (e.g., QRS width or fractionation), electrical activity of a late activation site in the left ventricle, mechanical contraction of the heart or measurement of the blood flow (e.g., the rate of change in pressure). The lead is repositioned and pacing and monitoring can be repeated.

Once a desired lead placement has been selected, pacing can be implemented in various ways. For instance, DDD (dual chamber) pacing can be implemented with or without a low atrial rate (e.g., around 50 beats per minute) and an AV delay of around one-half of the baseline or intrinsic AV interval. The DDD pacing can also be modified to use a variety of different Xstim pacing profiles, non-Xstim pacing profiles and combinations thereof.

Also according to an embodiment of the present invention, a way to assess improved heart function involves determining placement of a lead for sensing a late activation site in the left ventricle. The lead, which is capable of sensing electrical activity in nearby heart tissue, is advanced through the CS (coronary sinus) until monitoring results from the lead represent activation of a late activating region. The lead can be continuously advanced until activation of a distal electrode on the lead no longer occurs before any other electrode(s) on the lead. At this point, the current lead position can either be maintained or the lead can be slightly retracted.

While not bounded by theory, experimental data provides strong support that the beneficial effects on cardiac function provided by aspects of the present invention are due, at least in part, to His bundle stimulation. The data further supports that, unexpectedly, the His bundle may react more like a nerve than a myocyte with respect to responsiveness to electrical stimulation. This may be due in part to fibrotic encapsulation of the His bundle.

It is possible that the success of Xstim pacing can be attributed in part to the phenomena of anodal break stimulation in tissues with high directional anisotropy. It is also possible the success of Xstim pacing can be attributed in part to a phenomenon sometimes referred to as accommodation. Accommodation is an increase in voltage threshold necessary to produce depolarization of a nerve cell that occurs when the nerve is exposed to a non-zero voltage that is below the threshold voltage.

Embodiments of the present invention are directed to stimulation catheters, systems and methods that employ two or three electrodes and that can be used in connection with the various methods and systems discussed herein. In specific embodiments of the present invention, the most distal two electrodes are located at the tip of the catheter. An optional third electrode can be located in a number of places, such as on the lead body some distance from the first pair or even located between the pairs. The distance from the third electrode and the distal pair ranges from a few millimeters to a few centimeters. The catheter can have a helical fixation structure which can be either a passive (non-electrical) or active (serving as one of the tip electrodes). The catheter can be transvenously placed within the heart. The catheter is arranged such that once affixed to the heart tissue, the two pacing electrodes are in direct electrical contact with the cardiac tissue once. Experimental data suggests that such features can be useful for providing low and stable thresholds during standard pacing. It has also been observed that two pacing electrodes in contact with the wall can be useful in finding a stimulation region in the right ventricle that depolarizes the heart in a manner very similar to the normal activation sequence created by the normal intrinsic (originating in the sinus node) activation propagating through the His-Purkinje system.

Various embodiments can be implemented where the two stimulating electrodes are in direct contact with the heart tissue. Example embodiments are depicted in connection with FIG. 25A. These examples are not intended to exclude other possible implementations accomplishing similar results. For instance, one or more small porous conducting dots may be attached to the ring electrodes to increase the microscopic surface area (effective surface at the reactant level of physical interaction), and the helix electrode may be coated with material(s) to also increase the microscopic surface area. In various implementations, porous and raised portions of the electrode take the form of any number of shapes (e.g., lines, circles, squares or zig-zags). One implementation involves scoring the electrode (e.g., using a laser or etching). Other implementations can include nanostructures (e.g., nanowires and/or nanotubes) that are located on the contact surface of the electrodes. Such nanostructures can provide significant increase in contact surface area. Additionally, certain anti-inflammatory agents (e.g., a steroid) can be administered in connection with the active fixation pacing catheter.

Figure 25A:
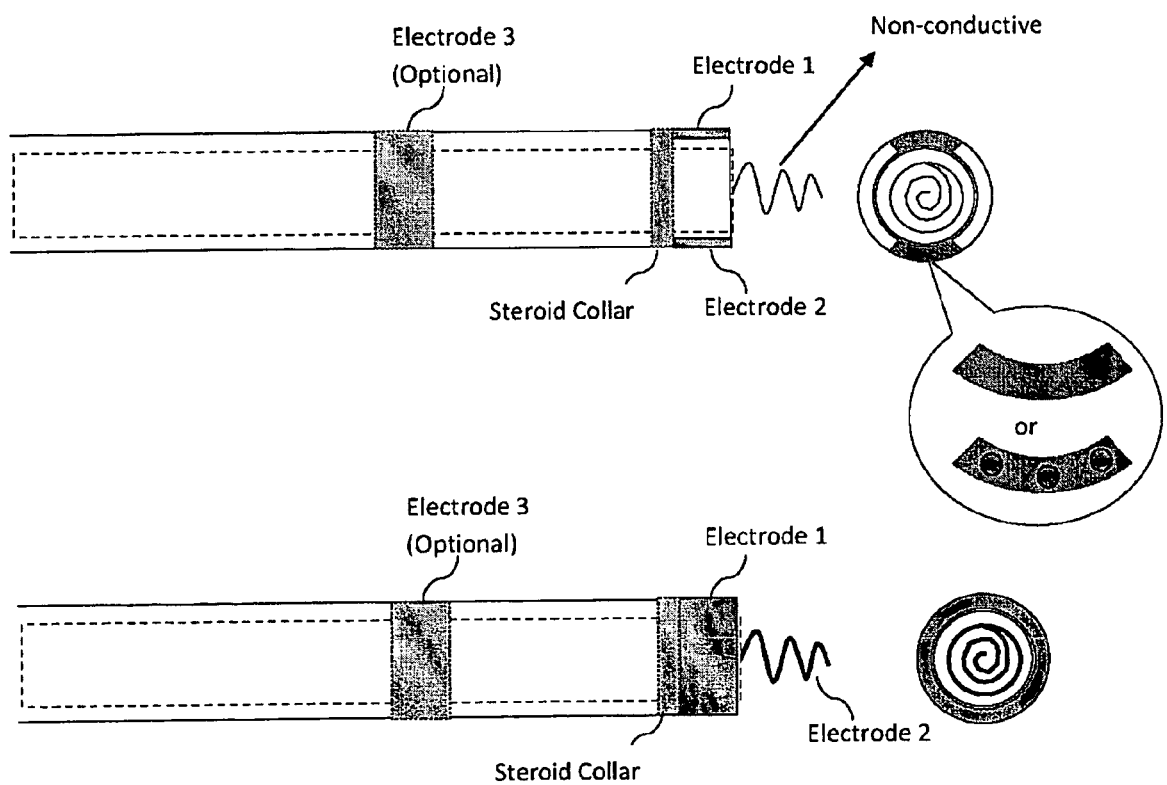
FIGS. 25A and 25B illustrate catheter arrangements useful with the various embodiments discussed herein.
Figure 25B:
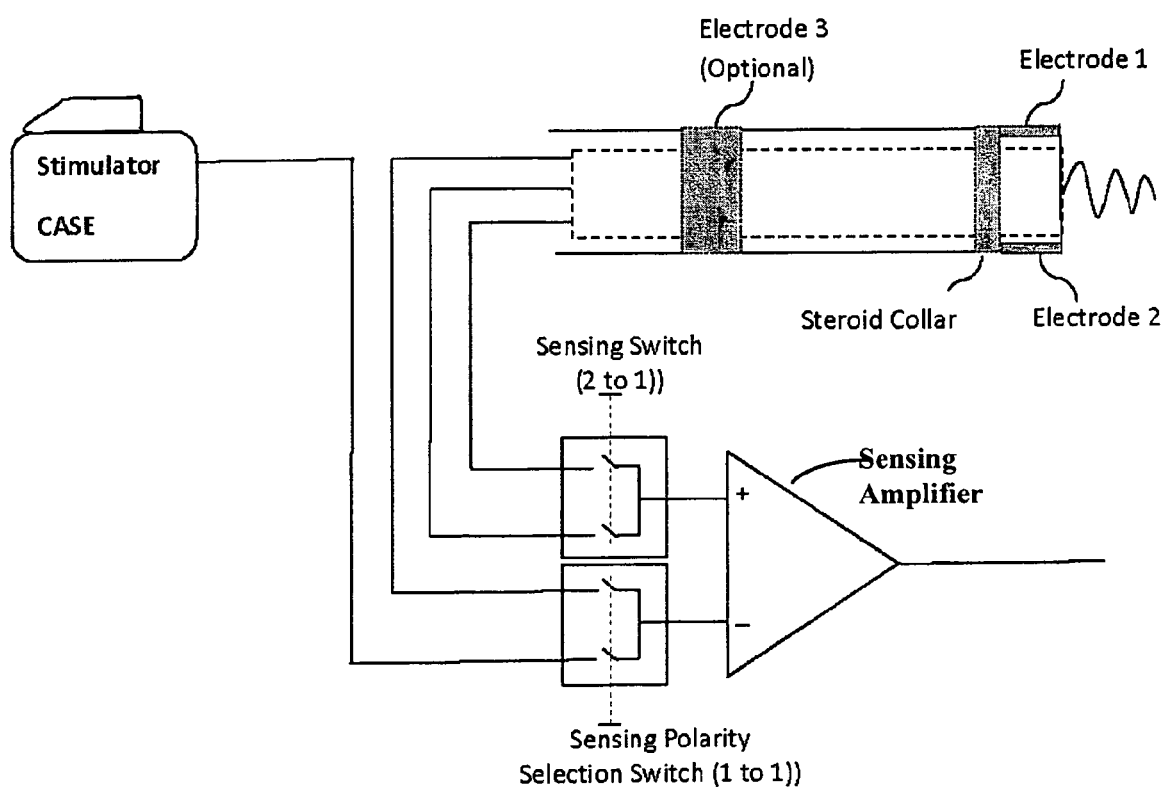

The configuration shown in FIG. 25B can be implemented in connection with methods and devices so as to provide sufficient contact surface area between the cardiac tissue and the electrode(s). Resistance between the electrode and the cardiac tissue can affect signals (e.g., pacing or sensing signals) transmitted between the heart tissue (including the conduction system of the heart) and the electrode. Generally speaking, the resistance of a conductor is inversely proportional to the cross-sectional area of the conductor with respect to the direction of current flow (e.g., R=resistivity*length/ cross-sectional area). Increasing the surface area of the electrode(s) that contacts the heart tissue can be particularly useful for detection of intrinsic cardiac depolarization signals.

The circuit diagram shown in FIG. 25B represents a simple example implementation and various other implementations are possible. One implementation involving the use of such a circuit is as follows. In a detection mode, electrodes 1 and 2 are connected to one input of the sensing amplifier through a sensing switch that will be open during simulation to avoid short circuit but closed whenever sensing is needed. The other input of the sensing amplifier can either connect to the stimulator CASE (e.g., for unipolar sensing) or to the optional electrode 3, if available (e.g., for bipolar sensing).

In a pacing mode, stimulation waveform(s), will be applied to the electrodes 1 and 2. In one application these waveforms are similar to those used with conventional catheters. Other applications employ stimulation waveforms including, but not limited to, an Xstim waveform and/or two simultaneous opposite polarity stimulation pulses with reference to either the CASE or electrode 3 (if available).

Various aspects of the various catheter arrangements can be useful for implementing methods and achieving results discussed herein. For instance, the ability to individually address each electrode can be useful for pace mapping, such as that discussed in connection with FIG. 26A. Other aspects of the catheter arrangements allow for pacing to determine the target location as well subsequent chronic pacing at the determined location.

Figure 26A:
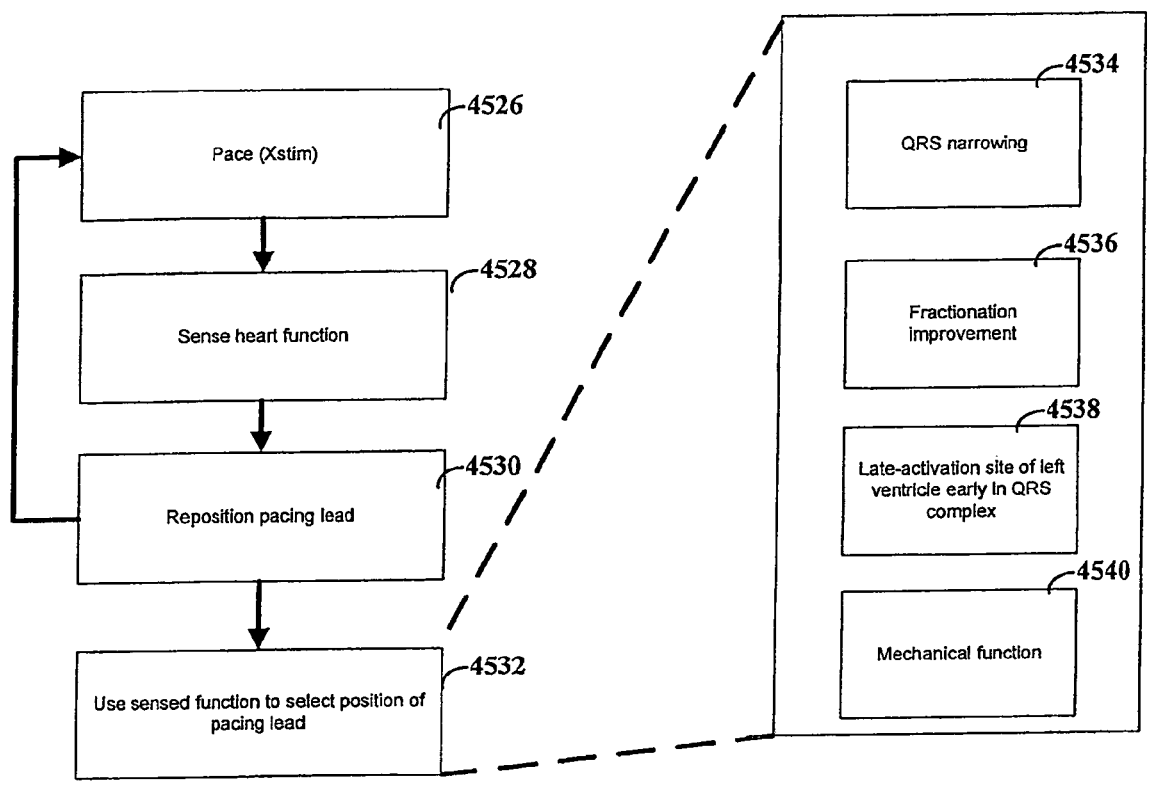
FIGS. 26A, 26B, 26C and 26D illustrate example procedures for determining pacing-lead placement.

FIG. 26A shows an example procedure for determining placement of a lead for pacing according to an embodiment of the present invention. This procedure was implemented to place the pacing lead in connection with the experimental results provided hereafter.

At step 4526, pacing of the heart is accomplished using a lead placed in the right ventricle and near the His bundle. In a specific instance, the lead includes two electrodes used to deliver oppositely charged pulses, such as with Xstim pacing. At step 4528, heart functionality associated with the pacing is monitored. The monitoring can include one or more of the following non-limiting examples, ECG readings (e.g., QRS width or fractionation), electrical activity of a late activation site in the left ventricle, mechanical contraction of the heart or measurement of the blood flow (e.g., the maximum rate of change in left ventricular pressure). In one implementation, the improved heart function can be based upon a comparison of heart function without any pacing. As discussed above, it has been discovered that voltages sufficiently above the capture threshold can lead to improved heart function relative to voltages near the capture threshold. Accordingly, one implementation of pacing uses relatively high voltages (e.g., +/−5V) when pacing to determine lead location. This can be useful to ensure that the improved heart function is seen. When the lead is not yet properly placed, pacing capture can sometimes still be obtained without exhibiting significant improvement in heart function. Thus, the improved heart function can sometimes be an improvement over heart function resulting from use of the pacing lead and pacing profile rather than (or in addition to) the baseline and/or un-paced heart function.

At step 4530, the lead is repositioned and pacing and monitoring steps 4526 and 4528 can be repeated as desired. The results of the monitoring step can be saved and correlated to the corresponding lead positions. At step 4532, the results of the monitoring step 4528 are used to determine the proper placement for the lead. A few examples of the results of the monitoring step are shown by 4534 (QRS narrowing), 4536 (fractionation improvement), 4538 (late activation site earlier) and 4540 (mechanical function improved). The lead can then be moved (back) to the lead position that is selected as a function of the monitoring results.

In another implementation, the steps 4530 and 4532 can be switched so that repositioning of the lead is done after evaluating the results of the monitoring step 4528. In this manner, the lead can be repositioned until satisfactory results are detected. This can be particularly useful for not having to record and recreate lead positions previously paced. Instead, once satisfactory monitor results are found, the current lead placement can be used.

Figure 26B:
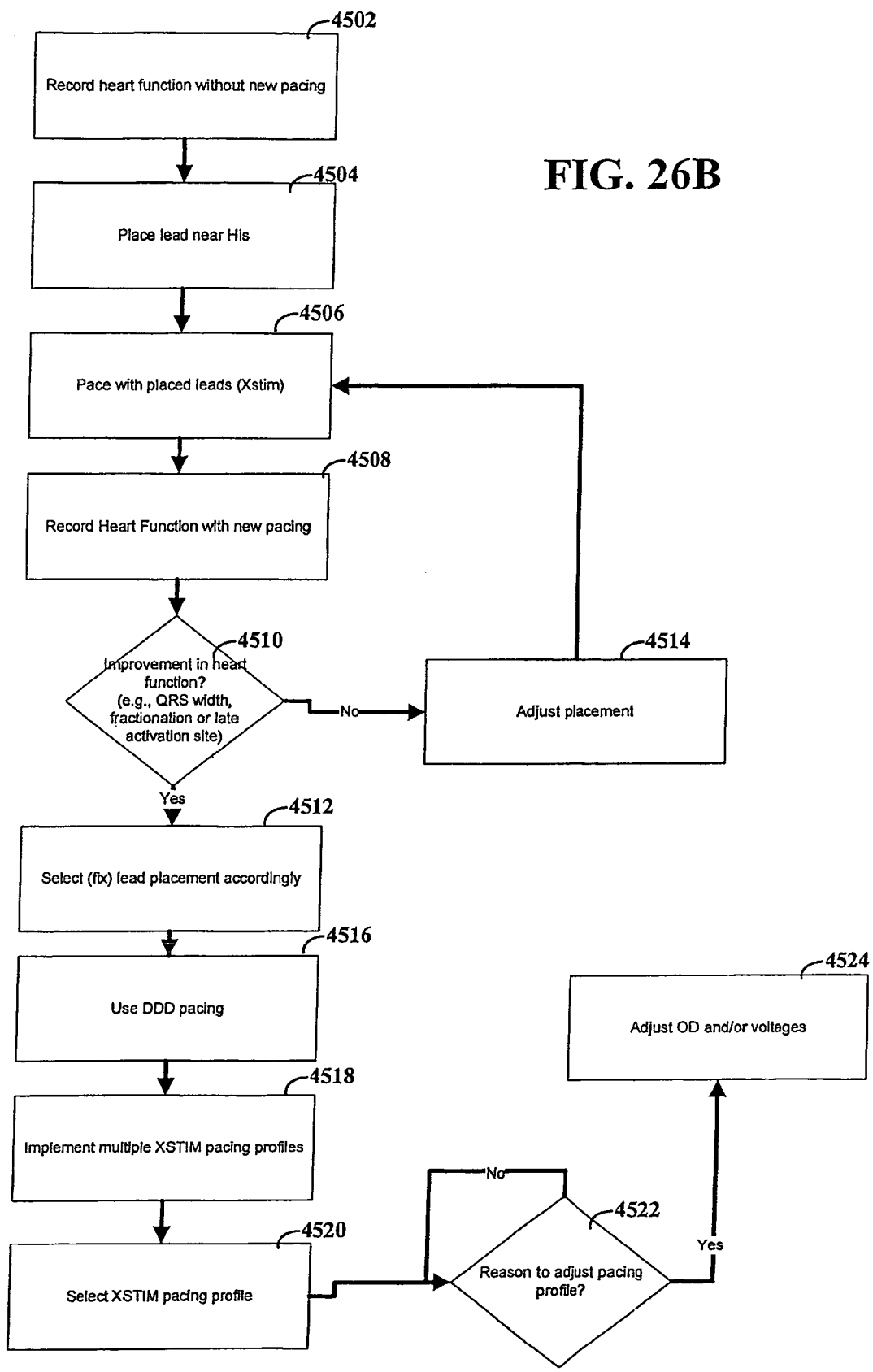

FIG. 26B shows an example procedure for determining placement of a lead for pacing according to an embodiment of the present invention. At step 4502 baseline heart function is recorded (e.g., without Xstim pacing). At step 4504 a lead capable of delivering Xstim pacing is placed near the His bundle (i.e., near the root of the septal leaflet of the tricuspid valve in the right ventricle). At step 4506 Xstim pacing is delivered to the placed lead. In a particular embodiment the Xstim pacing is consistent with the waveforms depicted by and discussed in connection with FIG. 18. At step 4508 the heart function associated with the Xstim pacing is recorded. If it is determined, at step 4510, that Xstim pacing improves heart function (e.g., narrowing of the QRS, less fractionated QRS, improving timing of a late activation site, improved mechanical function or improved pressure function), the placement of the lead can be selected (and fixed) at step 4512. Otherwise, the position of the placed lead can be adjusted at step 4514 and steps 4506-4510 can be repeated as necessary.

In a specific embodiment, the determination step 4510 can implemented using multi-lead ECG readings and a probe placed at a late activation site of the left ventricle (e.g., placing a lead near the posterior lateral wall of the left ventricle via a catheter inserted through the Coronary Sinus).

Once a desired lead placement has been selected, DDD pacing can be implemented as shown in step 4516. In a specific implementation, the DDD pacing is implemented with a low atrial rate (e.g., around 50 beats per minute) and an AV delay of around one-half of the baseline or intrinsic AV interval (to allow for full capture and atrial tracking and ventricular pacing). In an effort to find an acceptable (or optimize) pacing approach, the DDD pacing is modified to use a variety of different Xstim pacing profiles as shown in step 4518. As exemplified at step 4520, one or more of these profiles can be selected from the following non-limiting examples (discussed in terms of a lead with tip and ring electrodes for simplicity), in-phase pulses with positive voltage applied to the tip and negative voltage applied to the ring, in-phase pulses with negative voltage applied to the tip and positive voltage applied to the ring, out-of-phase pulses with opposite polarities applied to respective tip and ring electrodes.

In some instances it may be beneficial to adjust the pacing profile as shown by the determination step 4522. If so determined, the pacing profile can be adjusted in step 4524. For example, pocket stimulation effects, dry pocket or other effects due to chronic stimulation can result in the threshold voltage increasing. It has been discovered that shifting the overlap duration of the pulses (OD) can help compensate for such problems. In another example, the OD can be shifted to allow for lower pacing voltages, even where no dry pocket or other causes are present.

Figure 26C:
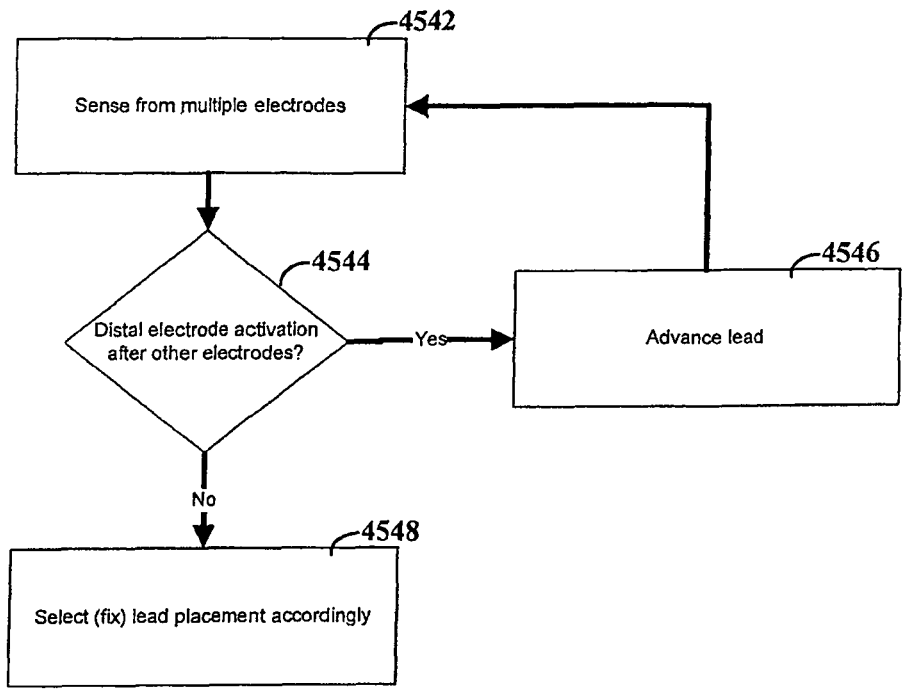

FIG. 26C shows an example procedure for determining placement of a lead for sensing a late activation site in the left ventricle, according to an embodiment of the present invention. As discussed herein, the monitoring of a late activation site of the left ventricle can be useful for placement of pacing lead(s) and/or assessment of pacing effectiveness. The method involves the use of a lead that is capable of sensing electrical activity in nearby heart tissue. The lead is advanced through the coronary sinus until monitoring results from the lead represent activation of a late activating region. In one embodiment, the lead can be advanced to a desired spatial position within the coronary sinus. The lead placement can be determined using a number of different mechanisms, such as fluoroscopy or physical measurements of distance of lead advancements. Each patient, however, may exhibit different morphology and/or electrical conduction/activation. Patients who have conduction abnormalities may exhibit late activation at sites different from patients with normal conduction. Thus, the method depicted by FIG. 26C uses electrical measurements taken from the advancing lead to determine the desired sensing position.

Figure 26D:
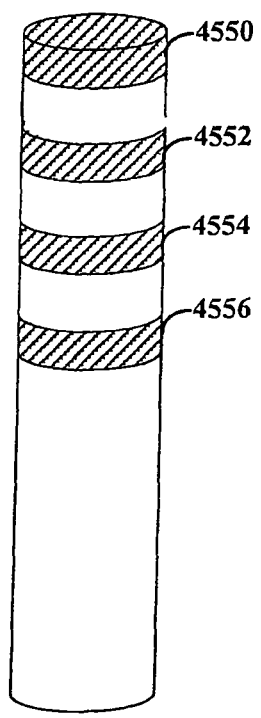

Step 4542 shows that the lead includes multiple sensing electrodes. These sensing electrodes are spatially disparate along the length of the lead. In this manner the most distal electrode represents the electrode that has been advanced the furthest. The remaining electrodes follow. A simplified version of an example lead is shown by lead 4500 (FIG. 26D). The distal sensing electrode 4550 is followed by sensing electrodes 4552, 4554 and 4556.

Once sensing readings are taken from step 4542, a determination is made at step 4544 as to the relationship between the activation times sensed at the sensing electrodes. In particular, if activation of the distal electrode 4550 occurs after activation of the other electrodes, the lead can be advanced further as shown by step 4546. The lead can be continuously advanced until activation of distal electrode 4550 no longer occurs before all of the other electrodes. At this point, the current lead position can either be maintained or the lead can be slightly retracted, as shown by step 4548.

Other implementations are possible, such as using a large number of different sensors. The lead can be advanced a significant distance into the coronary sinus and a particular sensor can be selected (e.g., by selecting a sensor that shows a late activation relative to the other sensors).

In a specific embodiment of the present invention, the absolute amplitude of the voltage presented to one of the electrodes can be less than the absolute amplitude of the voltage presented to the other electrode. This 'unbalanced' pacing profile may provide adequate pacing, while helping to control pacing power.

The power consumption of the pacing device can be an important consideration. While not bounded by theory, it is believed that different pacing profiles can be particularly advantageous to controlling pacing power. For example, during times that the pulses applied to each electrode overlap, the effective voltage seen between the electrodes is believed to be equal to that sum of their amplitudes. During times that the pulses do not overlap, the effective voltage is believed to be about equal to the amplitude of the active electrode. Assuming the voltages of the opposite polarity pulses have equal absolute magnitudes (A), the instantaneous power draw for overlapping pulses is proportional to $4A^2$. The instantaneous power draw for non-overlapping pulses is proportional to $A^2$. For completely overlapping pulses, each having duration T (and thus a total duration of T), the power drawn is then proportional to $4TA^2$. For completely non-overlapping pulses, each having duration T (and thus a total duration of 2T), the power drawn is proportional to $2TA^2$. While it has been observed that non-overlapping pacing profiles may exhibit pacing thresholds that are around 0.5 volts higher than those of overlapping pacing profiles, power savings are still believed to be possible using non-overlapping pulses in place of overlapping pulses.

Figure 27:
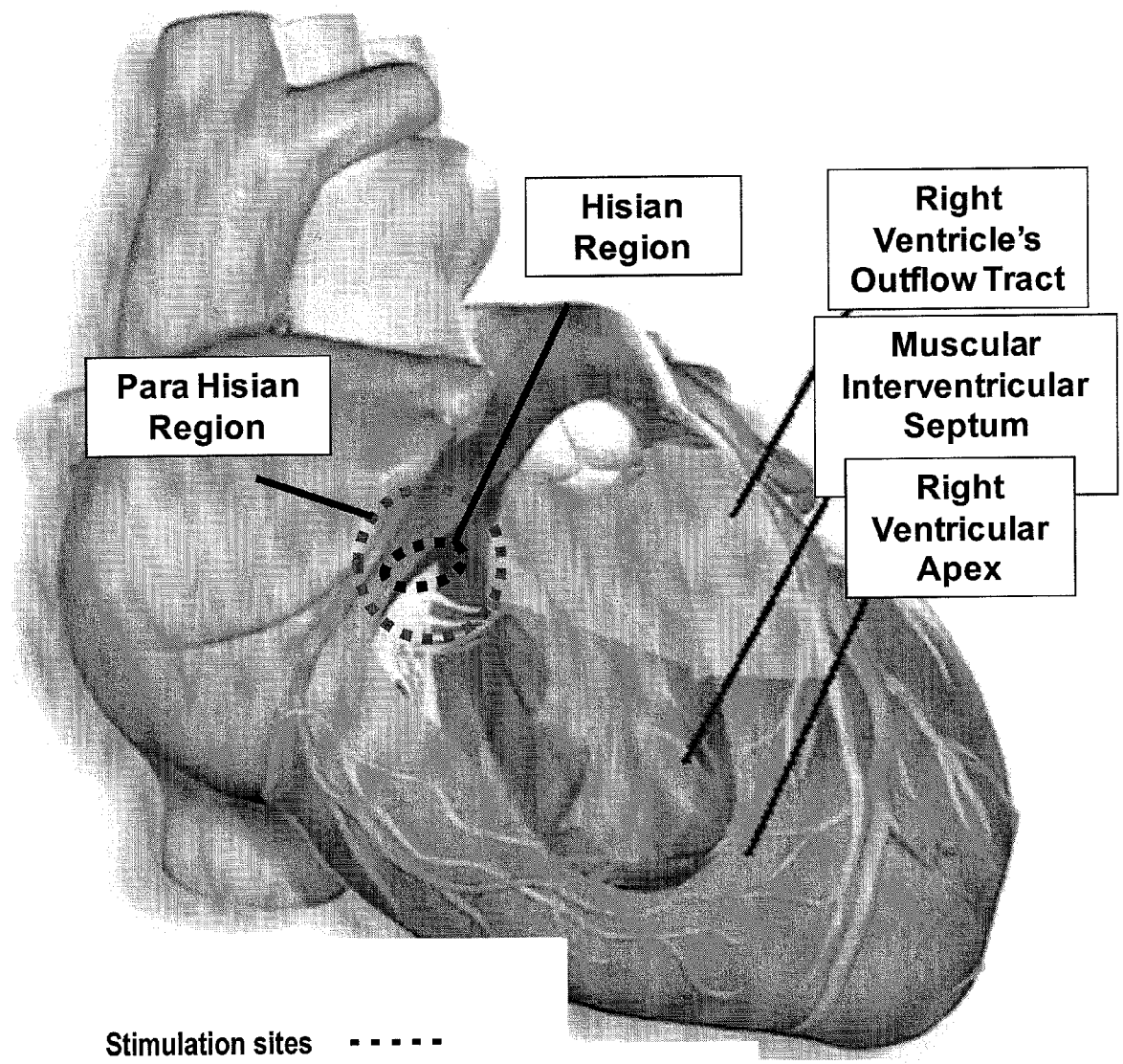
FIG. 27 shows a cross-sectional view of a heart and the Hisian and para-hisian regions, consistent with an embodiment of the present invention.

FIG. 27 shows a cross-sectional view of a heart and the Hisian and para-Hisian regions. In particular, FIG. 27 is a view of the right side of the heart, with the Hisian and para-Hisian pacing areas shown by the dotted lines. These regions represent the general area in which the pacing sites for the experimental data were collected.

Figure 28:
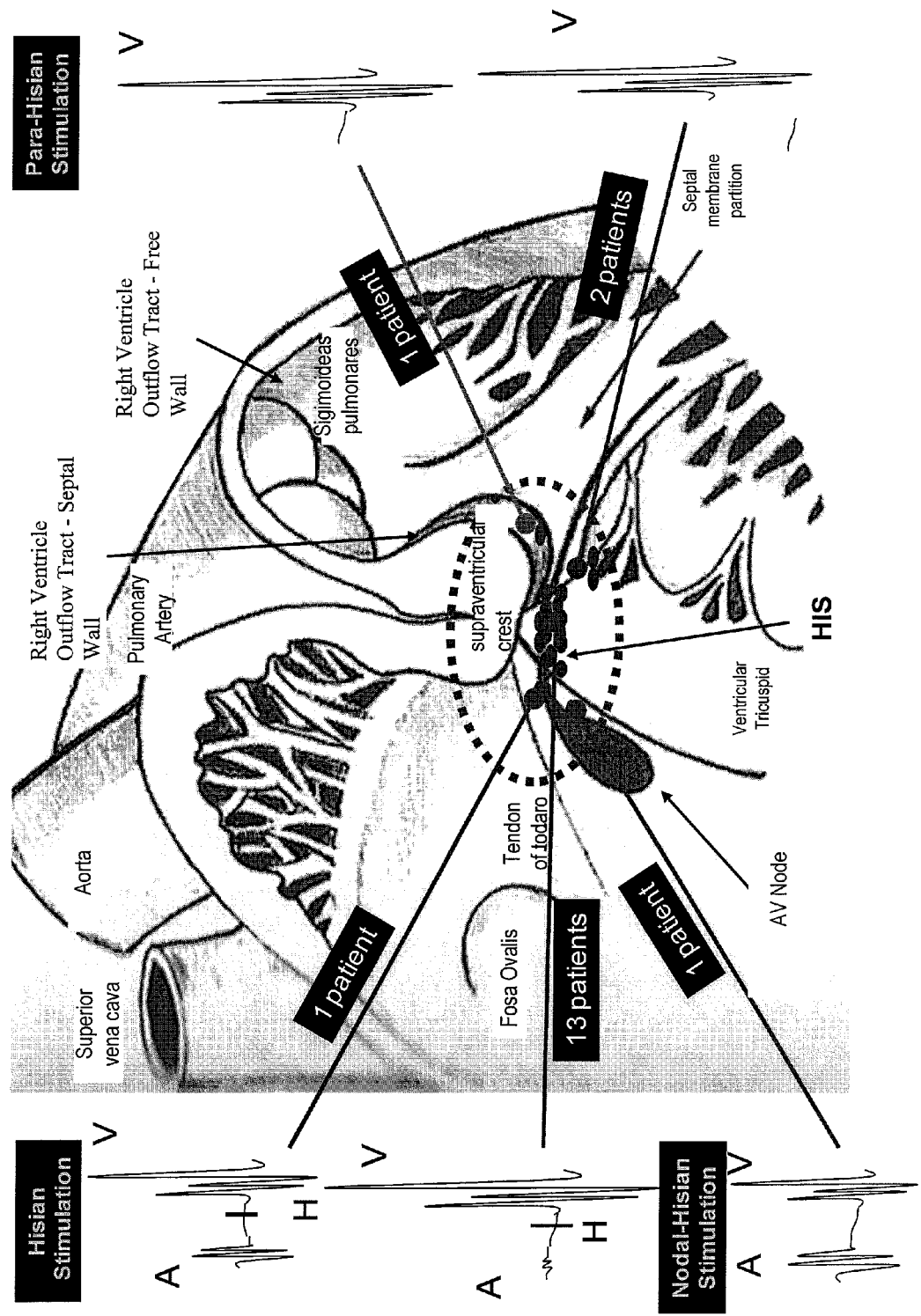
FIG. 28 shows a cross-sectional view of the heart marked with pacing sites.

FIG. 28 shows a cross-sectional view of the heart marked with pacing sites, according to an example embodiment of the present invention. Representative waveforms for different pacing areas are shown along the sides of the figure. The top left waveform represents a pacing site for a single patient and shows significant atrial (A), Hisian and ventricular (V) signals. The middle left waveform represents a pacing site for 13 patients and shows minor atrial signals with relatively strong Hisian and ventricular signals. The bottom left waveform represents a single patient and shows relatively strong atrial and ventricular signals with little Hisian signal. The right two waveforms represent a single patient and two patients, respectively, each with primarily only a ventricular signal.

Figure 29:
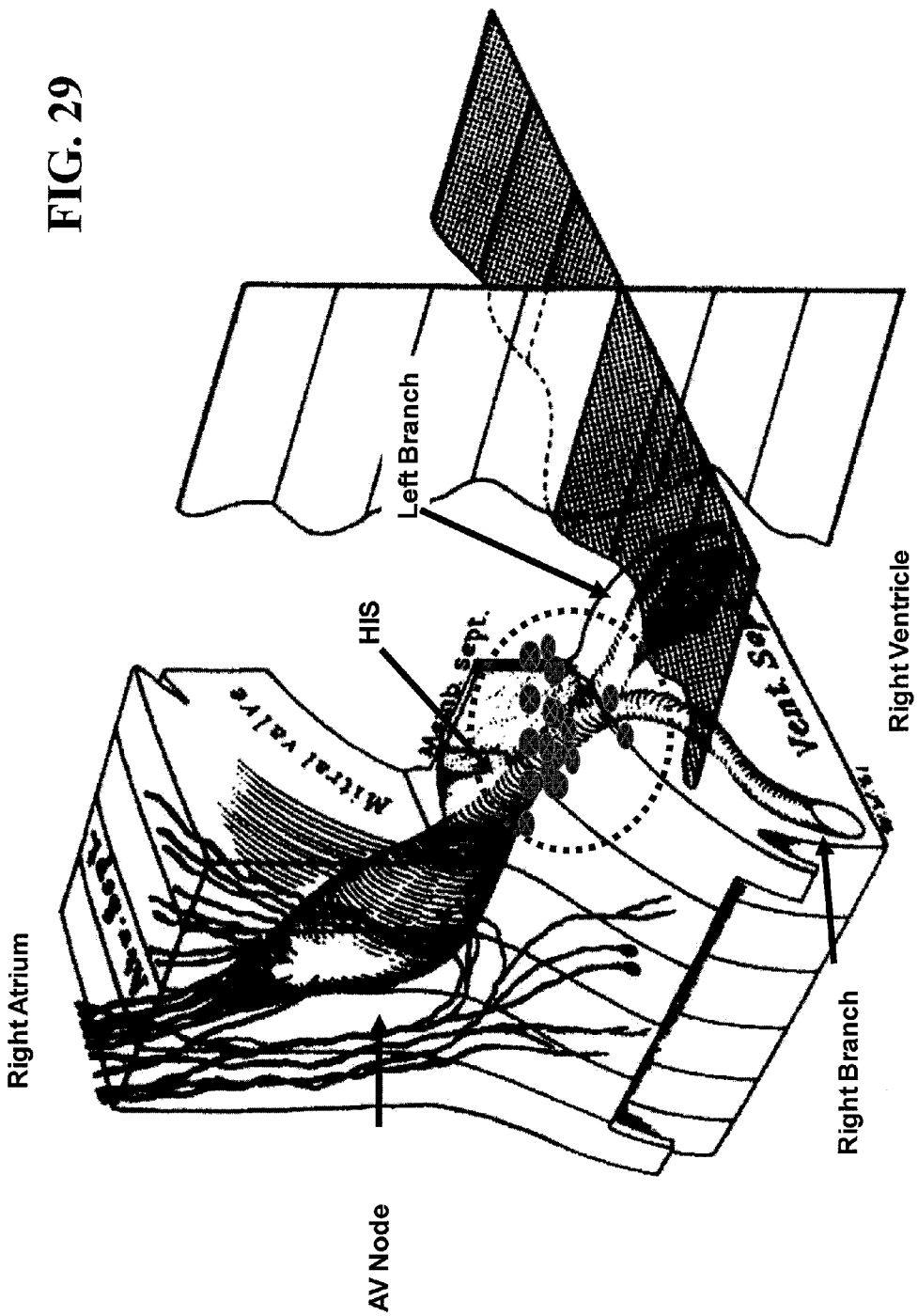
FIG. 29 shows pacing site locations on a 3-D depiction of the union of the AV node, the para-hisian and Hisian regions.

FIG. 29 shows the location of pacing sites on a three-dimensional depiction of the union of the AV node, the para-Hisian and Hisian regions.

Figure 30:
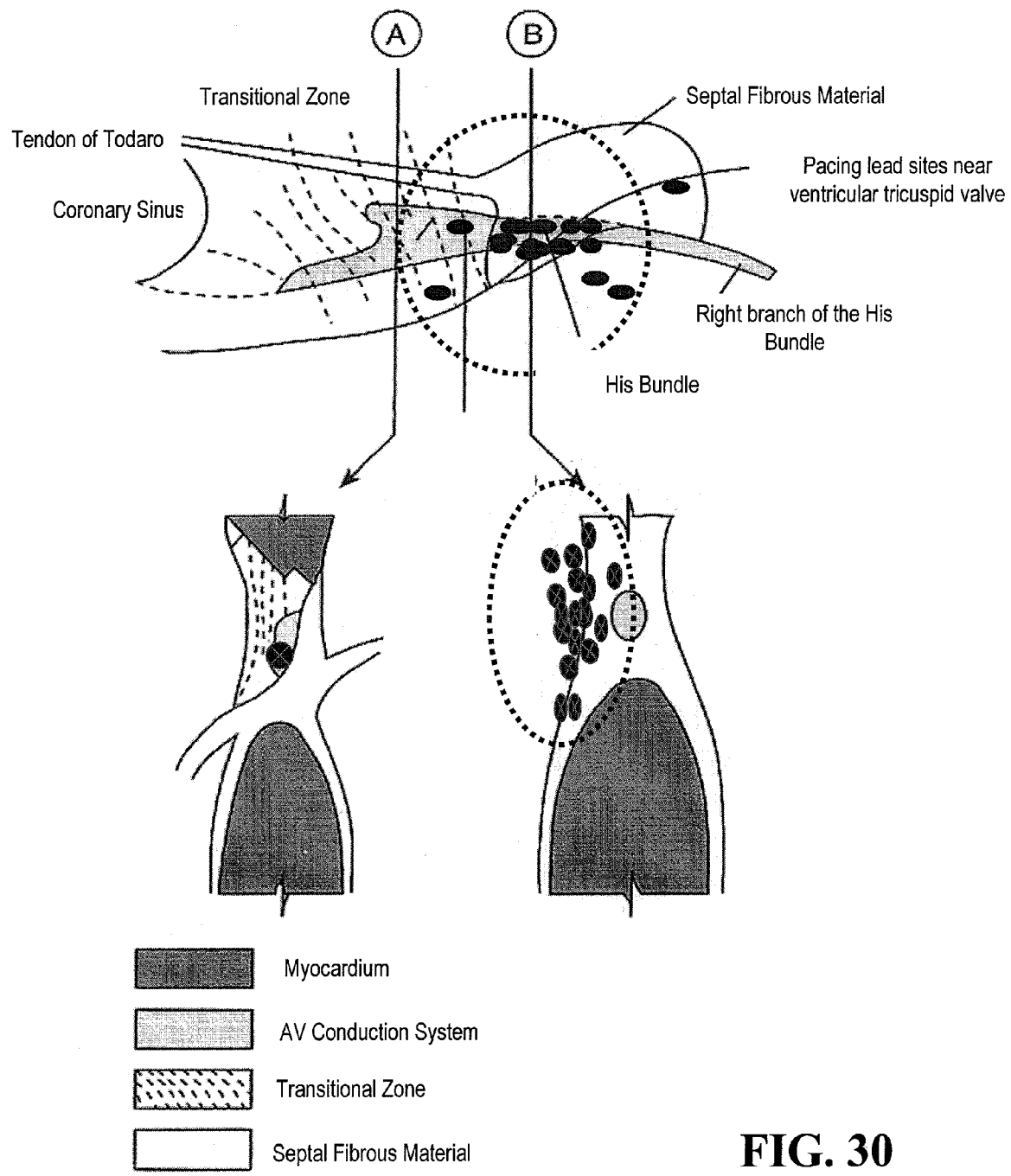
FIG. 30 shows pacing site locations on cross-sectional views of the heart.

FIG. 30 shows the location of pacing sites on several cross-sectional views of the heart. The upper view is a sectional view that includes part of the conduction system that includes the AV node, the His bundle and the right bundle branch. The lower two views show respective perpendicular views taken at respective portions of the conduction system of the upper view.

Figure 31:
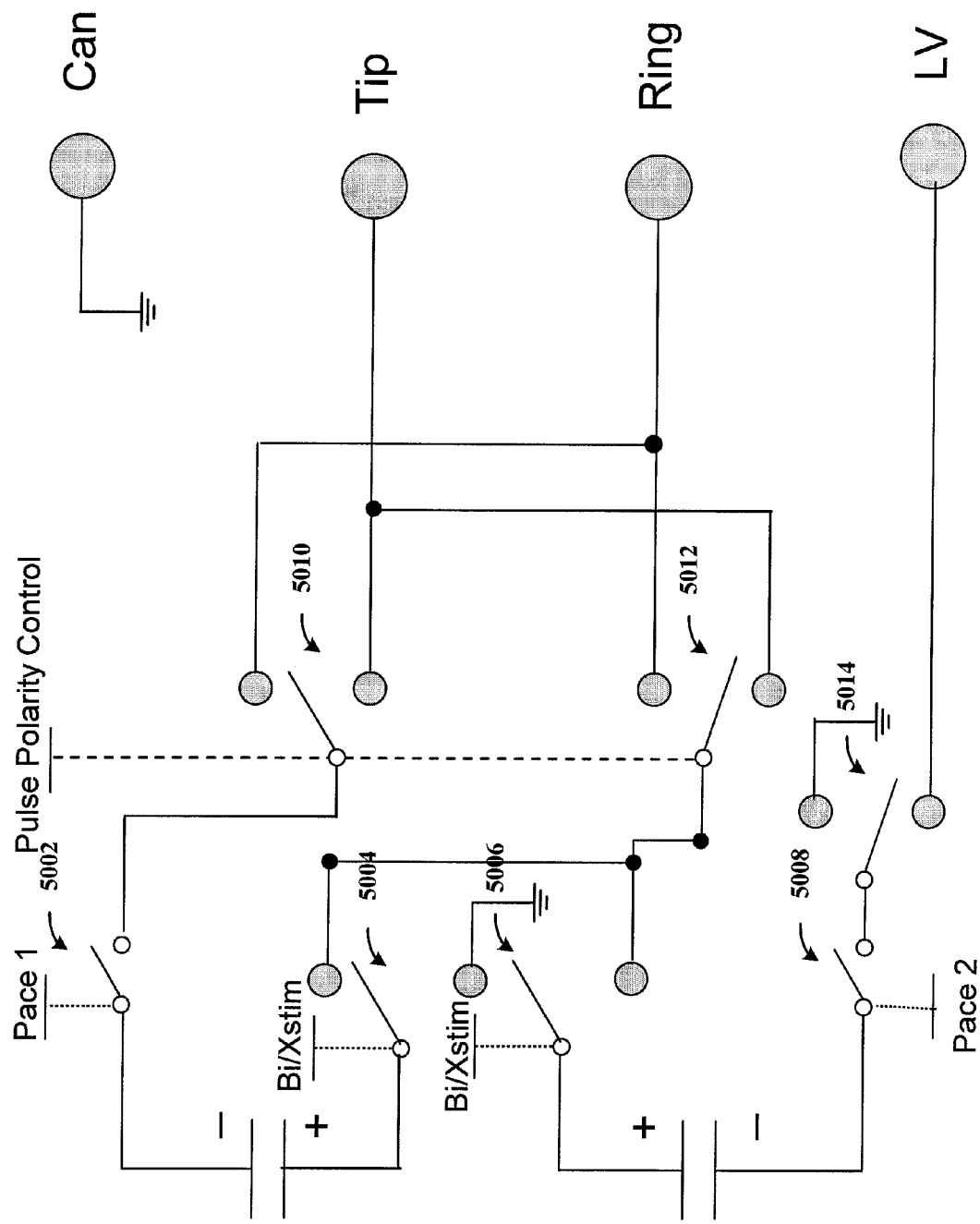
FIG. 31 shows an example circuit for providing various stimulation profiles.

FIG. 31 shows an example circuit for providing various stimulation profiles, according to an example embodiment of the present invention. Switches 5002 and 5008 are enabled to produce a pacing event. Switches 5004, 5006, 5010, 5012 and 5014 are set to provide a variety of pacing profiles. Switches 5004, 5006 and 5014 provide the ability to switch between bi-ventricular pacing and single-ventricle pacing (e.g., Xstim). Switches 5010 and 5012 provide the ability to modify the polarity of the pulses applied to the various electrodes.

In a first configuration, switches 5004, 5006 and 5014 are set for Xstim pacing. Switches 5004 and 5014 are connected to the ground (e.g., to the can or reference electrode). Switch 5006 is connected to switch 5012. In this manner both positive and negative voltages are delivered to the ring and tip electrodes as determined by switches 5010 and 5012. While the term ring and tip are used in connection with the circuit of FIG. 31, the electrodes need not be so limited. For instance, while the tip electrode is closer to the distal end of the lead, the tip electrode need not be located on the distal tip. Moreover, the ring electrode could be something other than ring as various other electrode configurations are possible.

In a second configuration, switches 5104, 5106 and 5114 are set for bi-ventricular pacing. Switch 5104 is connected to switch 5112. Switch 5106 is connected to ground. Switch 5114 is connected the left ventricle lead. In this manner, pacing can be delivered to leads located at both ventricles.

In another configuration, not shown with a figure, a three output channel arrangement to facilitate a BiV pacing profile where the LV is paced with a conventional negative pulse and RV paced with Xstim.

Switches 5110 and 5112 provide the ability to modify the polarity of the voltages seen between the ring and tip electrodes of the right ventricle pacing lead.

As should be apparent from the various discussions herein, the pacing profile can include, for example, variations in voltage levels, pulse durations and phase differences between pulses.

The variations in pacing profiles allow for a number of different applications to be implemented. In one such application, the results of pacing (e.g., QRS width, pressure measurements, synchronicity of contracts and the like) are compared between the different profiles. These results can then be used to select the pacing profile (e.g., Xstim or bi-ventricular) that is to be used for the patient.

In another application, the device includes a sensing function to detect the function of the left ventricle. The sensed function can be used to determine whether the current pacing profile is adequate and/or capturing a contraction of the left ventricle. In a specific instance, Xstim pacing is used while sensing heart function in the left ventricle. When the sensed function shows a potential problem (e.g., no capture, wide QRS or other problems) the pacing profile can be adjusted accordingly. Adjustment of the pacing profile can involve adjustment of the voltage. For instance, when partial or complete lack of capture is detected, the pacing voltage could be increased. Other example variations include a change in the polarity of the ring and tip electrodes or an adjustment of the phase of the applied voltages. In a specific example, when inadequate left ventricular function is detected, the device can be changed to a bi-ventricular pacing profile. In some instances, the device can periodically attempt to implement an Xstim pacing profile. If, during the attempt, adequate left ventricular function is detected, Xstim pacing can be resumed. Otherwise, biventricular pacing can continue to be implemented.

In yet another application, the device senses atrium function. This sensed function can be used, for example, to determine the timing for the ventricular pacing profile. The atrium function can be sensed using an electrode in the atrium, or using sensing near the His bundle (e.g., the Xstim pacing lead). When sensing near the His bundle, the sensed function can be detected using the ring lead, the tip lead and/or a dedicated sensing electrode. In a particular instance, the lead includes a sensing electrode that is closer to the distal end of the lead than the ring and tip electrodes. Generally speaking, such placement would allow the sensing electrode to be located such that the sensed atrium signal would be expected to be stronger (e.g., due to placement closer to the atrium).

Figure 20:
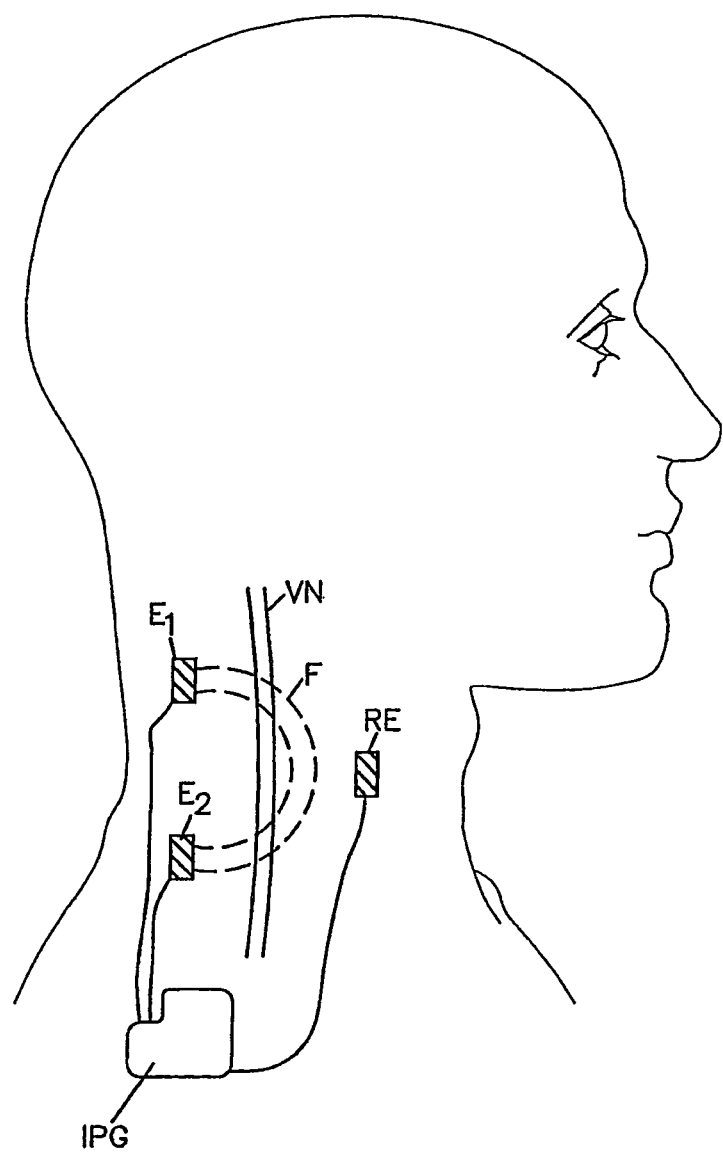
FIG. 20 is a side elevation view of a patient's head and neck showing application of the present invention to applying a pacing signal to a vagus nerve.

Cardiac applications represent a specific embodiment of the invention; however, the present invention is also applicable to other therapies, such as those where high current density spot(s) away from the electrodes are beneficial for stimulating the target including, but not limited to, nerves, muscle, gastric and intestine system, and cortex. For example, U.S. Pat. No. 5,299,569 to Wernicke et al. issued Apr. 5, 1994 (and incorporated herein by reference) is one of a number of patents assigned to Cyberonics, Inc. describing pacing the vagus nerve to treat a wide variety of disorders. Pacing electrodes are applied directly to the vagus nerve in, for example, the neck. Application of an electrode directly to the vagus nerve creates risk of mechanical injury (e.g., pressure necrosis) to the nerve. FIG. 20 illustrates use of the present invention in such application. Electrodes $E_1$, $E_2$ are placed subcutaneously near (transcutaneously or transvenously coupled) but not on the vagus nerve (VN) in the neck. A reference electrode RE is placed subcutaneously (transcutaneously or transvenously coupled) on an opposite side of the nerve VN. The electrodes $E_1$, $E_2$ and RE are connected to a pulse generator IPG. With signals as described above, the resulting field F captures the vagus nerve. The signals may be selected to have amplitude, frequency and other parameters as more fully described in the '569 patent. It will be appreciated that other alternative examples of using the present invention to pace an organ or the nerve will occur to one of ordinary skill in the art with the benefit of the teachings of the present invention.

The skilled artisan will recognize that the various aspects discussed in connection with the present invention can be implemented in a variety of combinations and manners. Moreover, aspects discussed in connection with the various references disclosed and incorporated herein, including those references indicated at the beginning of this document, can be used in combination with aspects of the present invention. In particular to the extent that the references indicated at the beginning of this document include a number of similar figures and related discussions, the skilled artisan would appreciate the interoperability of aspects disclosed therein even for figures not common between documents. These documents provide substantial disclosures throughout which teach aspects that can be used in combination with embodiments of the present invention and these documents are thus incorporated by reference in their entirety. For instance, the U.S. Provisional Patent Application identified by Ser. No. 61/020,511 includes an appendix with figures depicting various pacing electrodes and associated circuitry, and such embodiment(s) can be used in combination with aspects of the present invention.

The various embodiments described above are provided by way of illustration only and should not be construed to limit the invention. Based on the above discussion and illustrations, those skilled in the art will readily recognize that various modifications and changes may be made without strictly following the exemplary embodiments and applications illustrated and described herein. Such modifications and changes do not depart from the true spirit and scope of the present invention.

What is claimed is:

1. A method for delivering electrostimulation pulses to a heart using a catheter, the method comprising:
within a right ventricle of the heart, placing a first electrode facing outward from the distal end of the catheter in physical contact with a septal wall at or near a His Bundle of the heart by attaching the catheter to heart tissue; and
generating at least partially concurrent opposite polarity electrostimulation pulses for delivery at respective electrodes, including at least the first electrode and a second electrode, the electrostimulation pulses sufficient to capture the myocardium of the heart.

2. The method of claim 1, wherein attaching the catheter to heart tissue comprises affixing the catheter to the septal wall using a tine.

3. The method of claim 2, wherein attaching the catheter to heart tissue comprises affixing the catheter to the septal wall using a tine which extends from the distal end of the catheter.

4. The method of claim 1, including extending one or more of the first and second electrodes outward in a longitudinal direction from the distal end of the catheter.

5. The method of claim 4, wherein one of the first or second electrodes comprises a conductive tine configured to extend from the distal end of the catheter, and wherein attaching the catheter to heart tissue comprises affixing the catheter to the septal wall using the conductive tine.

6. The method of claim 5, wherein the conductive tine includes a helical shape.

7. The method of claim 5, wherein the conductive tine includes a coating comprising a material configured to modify the surface of the conductive tine to increase one or more of a porosity or a surface area.

8. The catheter of claim 1, wherein the first and second electrodes are arranged facing laterally outward from the catheter.

9. The method of claim 1, wherein the catheter includes a third electrode located between a distal and a proximal end of the catheter.

10. The method of claim 1, wherein the catheter includes an anti-inflammatory delivery device located near the distal end, and wherein the method comprises administering an anti-inflammatory agent from the delivery device.

11. The method of claim 1, wherein at least one of the electrodes includes a nanostructure.

12. The method of claim 1, wherein at least one of the electrodes includes a scored surface.

13. The method of claim 1, comprising sensing electrical activity of the heart using at least one electrode.

14. The method of claim 1, wherein the method comprises determining a location for attachment to heart tissue to provide increased heart function in response to the electrostimulation pulses including:
    delivering the electrostimulation pulses to a candidate location;
    in response, detecting one or more of QRS width narrowing, an electrogram fractionation improvement, an earlier activation of a late activation site, or an improved mechanical function of the heart; and
    attaching the catheter to the heart tissue at the candidate location.

15. The method of claim 1, comprising monitoring a function of the heart and in response, adjusting one or more parameters of the electrostimulation pulses.

16. The method of claim 15, wherein adjusting the electrostimulation pulses comprises shifting an overlap duration of the concurrent electrostimulation pulses.

* * * * *